United States Patent
Stevenson et al.

(10) Patent No.: US 10,828,498 B2
(45) Date of Patent: Nov. 10, 2020

(54) AIMD RF SWITCH TO CONNECT AN ICD DEFIBRILLATION ELECTRODE CONDUCTOR EITHER TO A FILTER CAPACITOR OR TO AN RF SOURCE CONFIGURED TO DETECT A DEFECTIVE IMPLANTED LEAD

(71) Applicant: Greatbatch Ltd., Clarence, NY (US)

(72) Inventors: Robert A. Stevenson, Canyon Country, CA (US); Keith W. Seitz, Clarence Center, NY (US); Jason Woods, Carson City, NV (US); Christine A. Frysz, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 16/854,138

(22) Filed: Apr. 21, 2020

(65) Prior Publication Data

US 2020/0246625 A1    Aug. 6, 2020

Related U.S. Application Data

(63) Continuation-in-part of application No. 16/414,996, filed on May 17, 2019, now Pat. No. 10,625,084.
(Continued)

(51) Int. Cl.
*A61N 1/375* (2006.01)
*A61N 1/39* (2006.01)
(Continued)

(52) U.S. Cl.
CPC ......... *A61N 1/3754* (2013.01); *A61N 1/3956* (2013.01); *A61N 1/362* (2013.01); *A61N 1/36053* (2013.01)

(58) Field of Classification Search
CPC .... A61N 1/3754; A61N 1/3956; A61N 1/362; A61N 1/36053
See application file for complete search history.

(56) References Cited

U.S. PATENT DOCUMENTS 4,424,551 A    1/1984   Stevenson et al.
5,333,095 A    7/1994   Stevenson et al.
(Continued)

OTHER PUBLICATIONS

John Camm, Editor-in-Chief, European Pacing, Arrhythmias and Cardiac Electrophysiology, Sep. 1, 2009, 1238-1239.
(Continued)

*Primary Examiner* — Mark Bockelman
(74) *Attorney, Agent, or Firm* — Michael F. Scalise

(57) ABSTRACT

An enhanced RF switchable filtered feedthrough for real-time identification of the electrical and physical integrity of an implanted AIMD lead includes a DOUBLE POLE RF switch disposed on the device side. Additionally, the RF switchable filtered feedthrough can optionally include transient voltage suppressors (TVS) and an MRI mode. In an embodiment, a DOUBLE POLE RF switch selectively disconnects EMI filter capacitors so that an RF test/interrogation signal is sent from the AIMD down into an implanted lead(s). The reflected RF signal is then analyzed to assess implanted lead integrity including lead body anomalies, lead insulation defects, and/or lead conductor defects. The Double Pole switch is configured to be controlled by an AIMD control signal to switch between FIRST and SECOND THROW positions. In the FIRST THROW position a conductive leadwire hermetically sealed to and disposed through an insulator is electrically connected to a filter capacitor, which is then electrically connected to the ferrule of a hermetic feedthrough of an AIMD. In the FIRST THROW position, EMI energy imparted to a body fluid side implanted lead can be diverted to the housing of the AIMD.
(Continued)

In the SECOND THROW position the conductive leadwire is electrically connected to an RF source disposed on the device side of the housing of the AIMD. While in the SECOND THROW position, a reflective return signal from the RF source is measured and analyzed to determine if the implanted AIMD lead exhibits any life-threatening performance issues, such as lead body anomalies, lead insulation defects or changes, or even defective, fractured or dislodged lead conductors. In another embodiment, a SINGLE POLE RF switch is configured to disconnect filter capacitors during the delivery of a high-voltage cardioversion shock from an implantable cardioverter defibrillator. Dis-connection of the filter capacitor either reduces or eliminates filter capacitor pulse inrush currents, which allows for the use of standard low-voltage filter capacitors instead of larger and more expensive high-voltage pulse rated filter capacitors. Disconnection of the filter capacitor also allows for an RF interrogation pulse to be applied to the implanted lead in real-time (for example, pre-set intervals throughout the day).

33 Claims, 38 Drawing Sheets

Related U.S. Application Data

(60) Provisional application No. 62/673,398, filed on May 18, 2018.

(51) Int. Cl.
  *A61N 1/362* (2006.01)
  *A61N 1/36* (2006.01)

(56) References Cited

U.S. PATENT DOCUMENTS

| | | | |
|---|---|---|---|
| 5,896,267 A | 4/1999 | Hittman et al. | |
| 5,905,627 A | 5/1999 | Brendel et al. | |
| 5,959,829 A | 9/1999 | Stevenson et al. | |
| 5,973,906 A | 10/1999 | Stevenson et al. | |
| 6,275,369 B1 | 8/2001 | Stevenson et al. | |
| 6,529,103 B1 | 3/2003 | Brendel et al. | |
| 6,765,779 B2 | 7/2004 | Stevenson et al. | |
| 6,888,715 B2 | 5/2005 | Stevenson et al. | |
| 7,038,900 B2 | 5/2006 | Stevenson et al. | |
| 8,352,033 B2 | 1/2013 | Kroll | |
| 8,700,156 B2 | 4/2014 | Kroll | |
| 8,812,103 B2 | 8/2014 | Kroll et al. | |
| 8,825,158 B2 | 9/2014 | Swerdlow | |
| 9,272,150 B2 | 3/2016 | Kroll et al. | |
| 9,427,577 B2 | 8/2016 | Kroll et al. | |
| 9,486,624 B2 | 11/2016 | Swerdlow | |
| 9,492,659 B2 | 11/2016 | Brendel et al. | |
| 9,636,500 B2 | 5/2017 | Swerdlow et al. | |
| 9,675,799 B2 | 6/2017 | Kroll et al. | |
| 9,757,558 B2 | 9/2017 | Stevenson et al. | |
| 9,814,876 B2 | 11/2017 | Swerdlow | |
| 9,821,156 B2 | 11/2017 | Kroll et al. | |
| 9,827,416 B2 | 11/2017 | Swerdlow | |
| 10,625,084 B2 * | 4/2020 | Stevenson | H01G 4/35 |
| 2004/0235549 A1 | 11/2004 | Struble et al. | |
| 2007/0123949 A1 | 5/2007 | Dabney et al. | |
| 2009/0163980 A1 | 6/2009 | Stevenson | |
| 2009/0322632 A1 | 12/2009 | Milosevic | |
| 2010/0191236 A1 | 7/2010 | Johnson et al. | |
| 2014/0168917 A1 | 6/2014 | Marzano et al. | |
| 2015/0217111 A1 | 8/2015 | Stevenson et al. | |
| 2016/0301369 A1 | 10/2016 | Heaney et al. | |

OTHER PUBLICATIONS

Extended European Search Report, Application No. 19154697.7, dated Jun. 4, 2019.

* cited by examiner

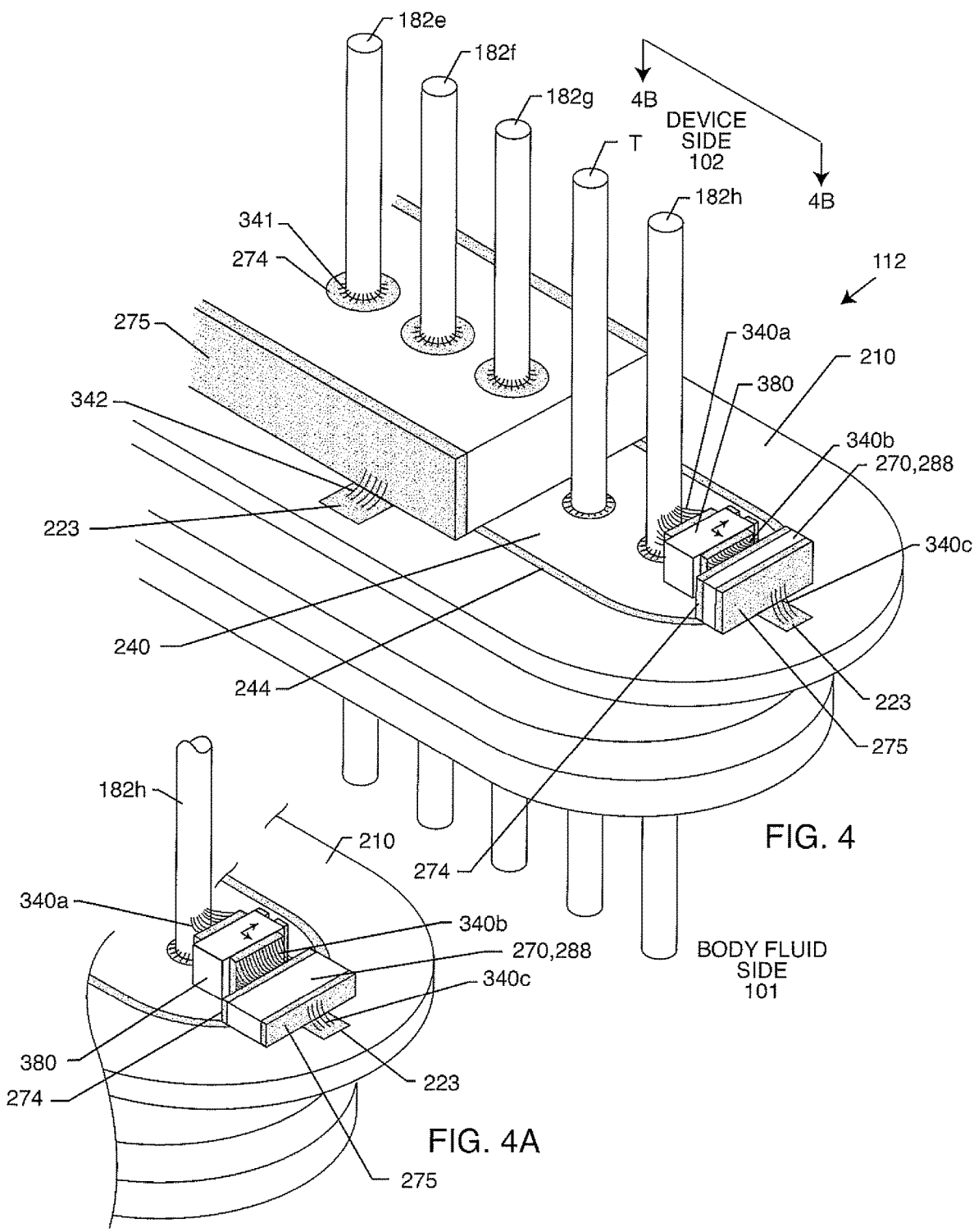

$$i_c = C = \frac{dv}{dt} \approx C\frac{\Delta v}{\Delta t} = \frac{(1500\ picofarads\ )(1300\ volts)}{75\ nanoseconds} = 26\ amps$$

THE HAYE'S CRITERIA

TABLE 1. DEFINITION OF THE THREE CLASSES OF CLINICALLY SIGNIFICANT INTERFERENCE WITH PACEMAKER FUNCTION.*

Class I

Interference associated with the following symptoms: presyncope, syncope, dizziness, shortness of breath
Transient ventricular inhibition for 3 seconds or more
Transient atrial inhibition for 3 seconds or more in a patient with a pacing mode of AAI or AAIR
Persistent ventricular inhibition
Persistent atrial inhibition in a patient with a pacing mode of AAI or AAIR
Any change in programmed settings
Secondary events of supraventricular or ventricular arrhythmias Class II†

Transient (intermittent) ventricular inhibition for more than 2 seconds but less than 3 seconds
Transient (intermittent) atrial inhibition for more than 2 seconds but less than 3 seconds in a patient with a pacing mode of AAI or AAIR
Transient (constant) ventricular inhibition
Transient (constant) atrial inhibition in a patient with a pacing mode of AAI or AAIR
Any type of interference and the presence of palpitations
Persistent interference of the following types: undersensing, tracking, cross-talk or safety pacing, rate-adaptive sensor-driven pacing, atrial noise-reversion mode, ventricular noise-reversion mode, atrial inhibition, asynchronous pacing, mode switching
Any of the following secondary events: pacemaker-mediated tachycardia, rate-drop response, rate-adaptive pacing Class III Any other type of interference
Any other secondary events

*AAI denotes atrial pacing, atrial sensing, inhibition response; and AAIR atrial pacing, atrial sensing, inhibition response, rate-adaptive.

†Intermittent transient interference lasted less than 50 percent of the duration of exposure to the telephone, and constant transient interference lasted for at least 50 percent of the period of exposure.

FIG. 20

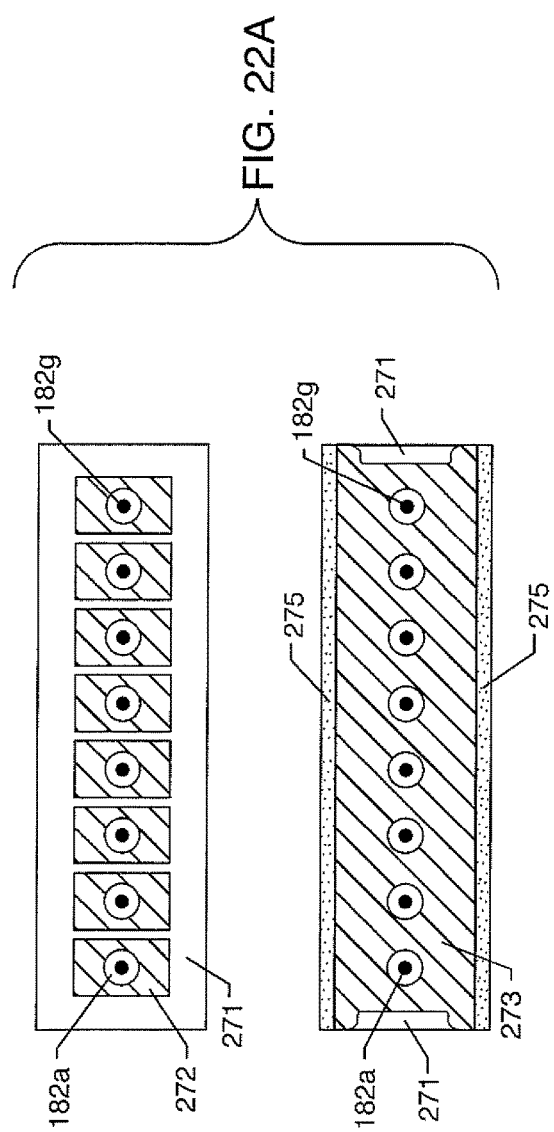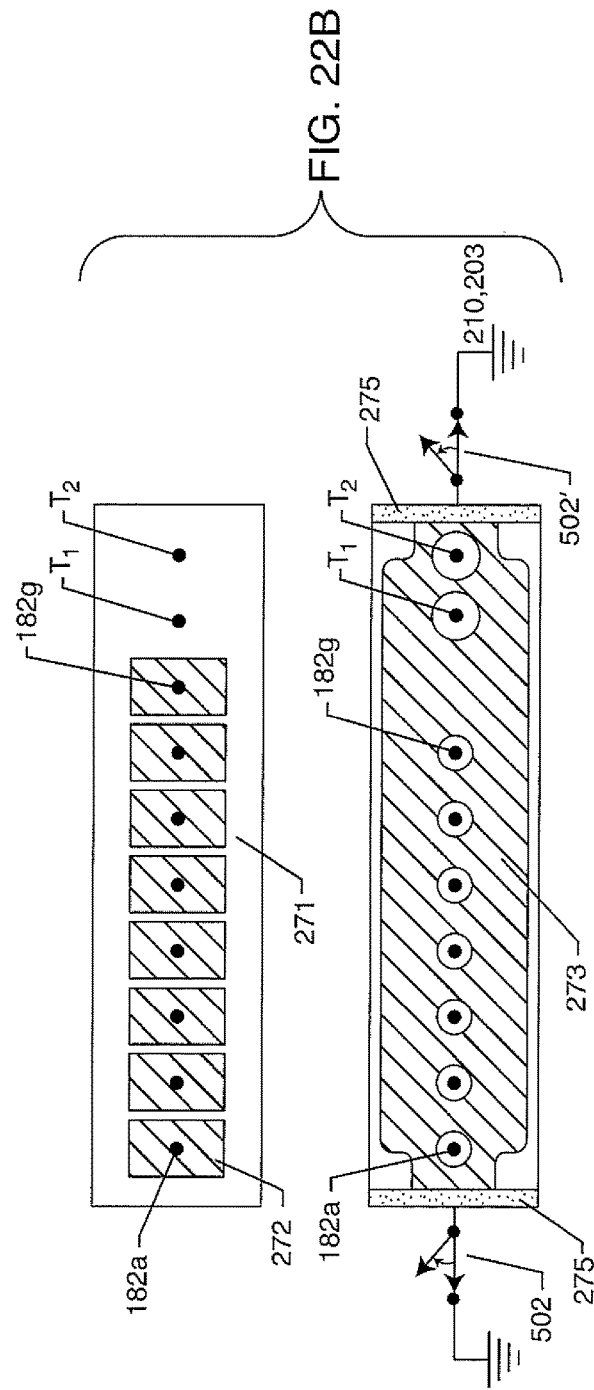

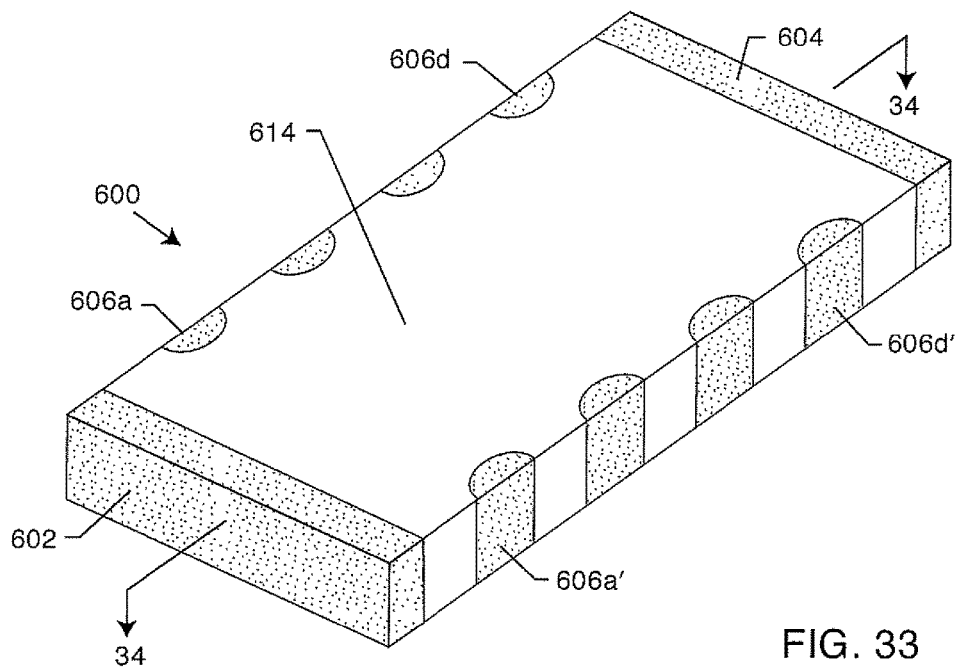
FIG. 33
PRIOR ART
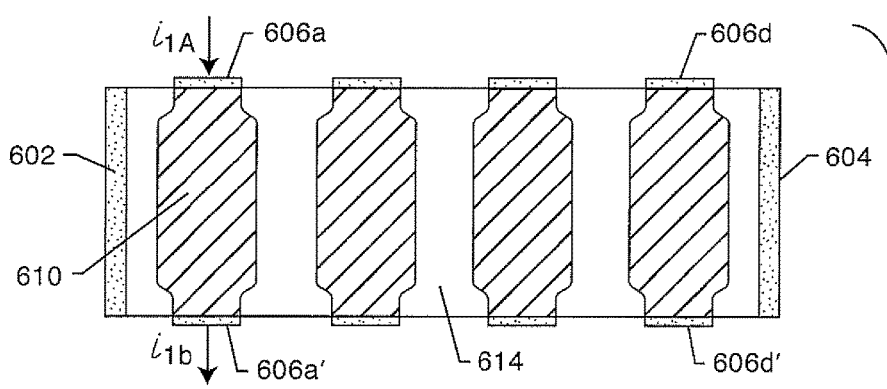
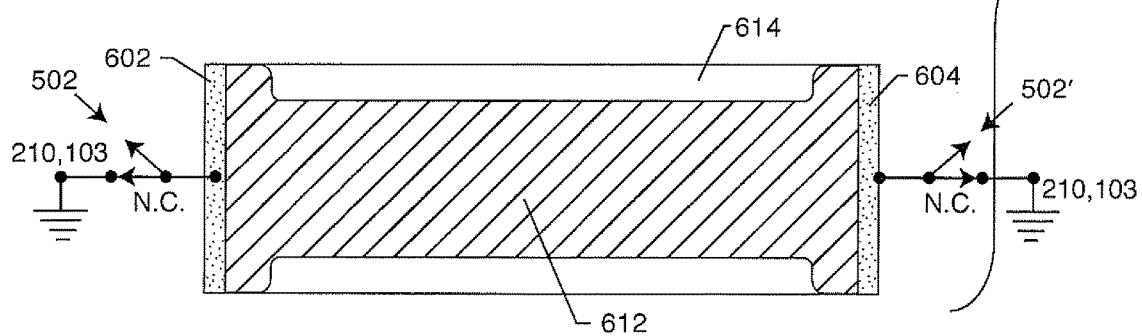
FIG. 34

X2Y

AIMD RF SWITCH TO CONNECT AN ICD DEFIBRILLATION ELECTRODE CONDUCTOR EITHER TO A FILTER CAPACITOR OR TO AN RF SOURCE CONFIGURED TO DETECT A DEFECTIVE IMPLANTED LEAD

CROSS-REFERENCE TO RELATED APPLICATIONS

This non-provisional patent application is a continuation-in-part of U.S. patent application Ser. No. 16/414,996, filed on May 17, 2019, now U.S. Pat. No. 10,625,084, which claims priority to U.S. provisional application Ser. No. 62/673,398, filed on May 18, 2018, the contents of which are fully incorporated herein with these references.

FIELD OF THE INVENTION

The present invention generally relates to EMI filtered feedthroughs for AIMDs. More particularly, the present invention relates to a filtered feedthrough comprising a novel switch utilizing a filter capacitor such that the switch can be temporarily used for implanted lead RF signal interrogation while the implanted lead is still capable of filtering EMI and delivering electrical therapy, such as implantable cardioverter defibrillator (ICD) high-voltage cardioversion shock delivery. The RF switch(es) can alternatively be used to disconnect filter capacitors during delivery of an ICD high-voltage (HV) shock pulse thereby enabling the use of smaller and less expensive commercially available low-voltage filter capacitors (in particular, reverse geometry MLCCs).

BACKGROUND OF THE INVENTION

Patents and patent applications to Charles Swerdlow and/or Mark Kroll (herein, including U.S. Pat. Nos. 9,827, 416; 9,821,156; 9,814,876; 9,675,799; 9,636,500; 9,486, 624; 9,427,577; 9,272,150; 8,825,158; 8,812,103; 8,700,156 and 8,352,033; U.S. patent application Ser. Nos. 15/810,324; 15/080,343; 15/344,864; 14/224,281 and 14/203,688; PCT Application Nos. PCT/US13/43386; PCT/US13/72957 and PCT/US15/22435; Provisional Applications Nos. 60/999, 041; 61/236,586; 61/689,189; 61/733,713; 61/817,667; 61/834,540; 61/841,107; 62/231,087 and 62/283,104; Foreign Patent Application Ser. Nos. EP2928547A1; EP2859364AI and EP2854702A1; and their related families are fully incorporated herein by these references. These patents are hereinafter referred to as the Swerdlow and Kroll patents.

Additional prior art patents that are also fully incorporated by these references include U.S. Pat. Nos. 4,424,551; 5,333, 095; 5,896,267; 5,905,627; 5,959,829; 5,973,906; 6,275, 369; 6,529,103; 6,765,779; 6,888,715; 7,038,900; 9,492,659 and 9,757,558.

Referring to the '156 and '150 patents, the primary inventive concept was to introduce an RF signal down the lead conductor of the shocking electrode(s) to determine if the insulation or the lead conductor has been compromised such as by abrasion, a cut, a break, and the like. The '156 and '150 patents disclose that if the shocking electrode migrates too close to the lead conductor or if the insulation on the lead conductor is compromised so that the conductor is exposed to body fluids, during a high-voltage shock a large amount of the energy is undesirably dissipated in the wrong area. Consequently, a portion of the high-voltage shock is not available to cardiovert the heart, which can lead to death due to ventricular fibrillation.

Inventors Swerdlow and Kroll have conceived of using an RF source and a reflective return signal known as the $S_{1,1}$ to diagnose implanted AIMD lead anomalies, such as insulation failures. In network analysis and in using network analyzers, the $S_{1,1}$ signal is known as the reflection signal. By analyzing the reflection signal, one can determine whether the lead body, lead insulation or the high-voltage shocking conductor(s) of an implanted AIMD lead has compromised performance. Such compromised performance can result from one or more of the following: undesirable electrode migration toward the edge of the lead body, undesirable migration of the lead distal tip away from the therapy delivery target, damaged lead insulation, lead abrasion, an inter-lumen insulation defect, compromised lead insulation, a fractured lead conductor, or a damaged lead conductor. Any one of these undesirable lead-related anomalies can cause adverse therapy delivery events, whether such anomalies occur alone or in combination with each other. For example, damaged lead insulation can reduce the insulation resistance of an implanted lead, which can then adversely affect cardioversion shocking energy such that the delivered shock therapy is reduced (less effective) or even completely lost (which is life-threatening to a patient). In addition, damaged/reduced lead insulation or damaged lead conductors can create noise thereby confusing ICD sensing circuits, which can then result in inappropriate HV shock delivery to ICD patients. Swerdlow and Kroll spent a great deal of time discussing and trying to figure out how to build an EMI filter that would protect the shocking lead, for example, the SVC lead pin #10, from undesirable EMI signals while at the same time allowing an interrogation RF source to pass through said shocking lead. Typically, the RF source that does the $S_{1,1}$ interrogation would be on the order of 125 MHz to 500 MHz or greater. It is not currently possible to inject an RF test signal to an implanted lead in the presence of passive RF filter capacitors which are essential to protect the AIMD from EMI a patient encounters in their daily living environment (such as from a cellular phone). Moreover, design of a passive multistage bandpass or notch filter(s) is not practical due to AIMD space and size limitations. In addition, the frequencies of the EMI signals involved are spaced too close to the frequency of the $S_{1,1}$ test signal. Active electronic filters would also not work as they become non-linear in the presence of high amplitude signals, such as from cellular phones or Tetra radios. For example, Tetra radios are being introduced into the marketplace that operate at approximately 150 MHz (to as high as 435 MHz). As such, the inventors conceived of an RF switch to temporarily disconnect the EMI filter capacitor(s) for a brief period of time so that an $S_{1,1}$ RF test signal (aka "The RF Interrogation Signal) can be injected to interrogate the integrity of an implanted AIMD lead.

Furthermore, indications for MRI of AIMD patients have grown considerably in recent years. Hence, MRI compatible active implantable medical devices (known as MRI conditional devices) have become very important. Such AIMDs are MRI conditionally approved by the FDA, the conditions of which MRI may be conducted being defined by the device manufacturer. Furthermore, an AIMD, particularly an ICD or a pacemaker in today's marketplace, needs to be MRI conditionally approved for both 1.5 Tesla and 3 Tesla MRI scanners. The RF frequency of 1.5 Tesla scanners is 64 MHz and for 3 Tesla scanners is 128 MHz. Since these RF frequencies are relatively close to the RF interrogation $S_{1,1}$ signal, building a filter having a notch ranging from 150 MHz to 435 MHz that is not mistaken for a Tesla scanner frequency is difficult.

The inventors of the present invention first discussed with Swerdlow and Kroll the possibility of using multi-element low pass notch filters or passive bandpass filters to create a very sharp cutoff frequency. The inventors analyzed a passive component 7-POLE Butterworth filter utilizing discrete capacitors and inductors. The inventors also considered and investigated 5-POLE to 8-POLE Tchebycheff filter designs. These types of filters are capable of providing a relatively sharp cutoff frequency, however, a filter small enough to fit inside an AIMD with a cutoff frequency sharp enough to attenuate a 128 MHz MRI signal while passing a 125 MHz $S_{1,1}$ interrogation signal 381 is not practical. Another example is attenuating a 500 MHz interrogation signal $S_{1,1}$ signal 381 while passing a 450 MHz Tetra radio signal. No matter what high frequency band one chooses for the interrogation signal 381, there is an EMI emitter(s) in an adjacent frequency band that is too close in frequency for multi-stage notch filters or bandpass filters to be practical. The high number of elements required for these sharp cutoff notch or bandpass filters becomes too complicated and physically much too large to fit inside an AIMD housing. It is difficult enough to fit a single element capacitive EMI filter inside an AIMD housing, much less a notch or bandpass filter with 5 to 7 discrete inductor and capacitor elements (for an ICD, at least one such filter is needed for the SVC and the RV terminal pins).

Another problem is that the capacitive elements of the Butterworth and Tchebycheff filter ceramic capacitor-type designs have an aging rate. Even if it were possible to have a sharp enough cutoff to separate 128 MHz MRI signal from 125 MHz signals, over time, due to capacitor aging, the Butterworth or Tchebycheff filter characteristic curves would change and their drift might lead then to overlap with the frequency that is intended to be cutoff. In other words, the use of sharp cutoff or notch filters is simply not practical.

Accordingly, the inventors of the present inventions have conceived of a novel RF switch that in the normal operating mode is configured to switch the desired conductor pin directly to a filter capacitor, for example a two-terminal MLCC chip capacitor, which is in turn connected to a ferrule ground. In this way, a high degree of EMI filtering is provided to a shocking electrode conductor through the RF switch to the passive EMI filter. In another embodiment, the inventors have conceived that the RF switch(es) of the present invention can partially or completely disconnect the filter capacitor(s) of the AIMD high-voltage circuits just prior to and during delivery of an ICD HV shock. Such dis-connection in ICD high-voltage (HV) shock circuits either reduces (by half) or eliminates the filter capacitor pulse inrush current $i_c$ entirely, which allows the use of commercially available and cost-effective low-voltage filter capacitors instead of larger and more expensive high-voltage pulse-rated filter capacitors.

SUMMARY OF THE INVENTION

Disclosed herein are embodiments of an RF switchable filtered feedthrough for real-time identification of the electrical and physical integrity of an implanted AIMD lead. The RF switchable filtered feedthrough includes an RF switch disposed on the device side, which may optionally include transient voltage suppressors (TVS) and/or an MRI mode. In an exemplary embodiment, a switching POLE is configured to be controlled by an AIMD control signal to switch between FIRST and SECOND THROW positions. In the FIRST THROW position a conductive leadwire hermetically sealed to and disposed through an insulator is electrically connected to a filter capacitor, which is then electrically connected to the ferrule of the hermetic feedthrough of the AIMD. In the FIRST THROW position, EMI energy imparted to a body fluid side implanted lead can be diverted to the housing of the AIMD. In the SECOND THROW position the conductive leadwire is electrically connected to an RF source disposed on the device side of the housing of the AIMD. While in the SECOND THROW position, a reflective return signal from the RF source is measured and analyzed to determine if the implanted AIMD lead exhibits any life-threatening performance issues. The RF switchable filtered feedthrough thereby provides real-time (programmed) identification of implanted AIMD lead-related integrity issues, such as, but not limited to: 1) lead body anomalies; 2) lead insulation defects or changes; 3) defective, fractured or damaged lead conductors; 4) lead dislodgment or migration; 5) lead inter-lumen insulation issues; wherein said implanted AIMD lead-related integrity issues occur either alone or in combinations thereof. In another embodiment, a SINGLE POLE-SINGLE THROW (SPDT) RF SWITCH, or alternatively a SINGLE POLE-DOUBLE THROW (SPDT) RF switch is configured to disconnect filter capacitors during the delivery of a high voltage cardioversion shock from an implantable cardioverter defibrillator. In certain embodiments, multi-POLE switches may be used such as a DOUBLE POLE-DOUBLE THROW (DPDT or nP-nT). In other words, the RF switches of the present invention may comprise any number of POLES or THROWS. Such dis-connection in bipolar high-voltage (HV) shock circuits either reduces (by half) or eliminates the filter capacitor pulse inrush current $i_c$, which allows the use of commercially available and cost-effective low-voltage filter capacitors instead of larger and more expensive high-voltage pulse-rated filter capacitors. In this embodiment, during an ICD pulse, the lead would not be interrogated by the RF signal 381.

Alternatively, when the ICD is not about to deliver an HV cardioversion shock, disconnecting the filter capacitor(s) also allows a Swerdlow and Kroll RF interrogation pulse 381 to be applied to the implanted lead in real-time to assess lead integrity (for example, at pre-set intervals such as multiple times throughout a day or a week, etc.).

In an exemplary embodiment of the present invention, an RF switchable filter feedthrough 112 of an active implantable medical device (AIMD, 100) comprises: a) an electrically conductive ferrule 210 configured to hermetically seal an opening 104 of a housing 103 of the AIMD, the ferrule configured to separate a body fluid side 101 opposite a device side 102, the ferrule including a ferrule opening 212 extending between and to the body fluid side and the device side, wherein, when the ferrule is attached to the opening of the housing of the AIMD the body fluid side resides outside the AIMD housing and device side resides inside the AIMD housing; b) an insulator 240 hermetically sealing the ferrule opening, the insulator configured to separate the body fluid side and the device side; c) a first conductive pathway 181, 182 hermetically sealed to and disposed through the insulator between the body fluid side and the device side, the first conductive pathway being in non-electrically conductive relation with the ferrule; d) an RF switch 380 disposed on the device side, the RF switch comprising: i) a first electrical connection 383 electrically connected to the first conductive pathway; ii) a second electrical connection 386 electrically connected to a first filter capacitor 270; iii) a third electrical connection 385 configured to be electrically connected to an RF source 381 disposed on the device side of the housing of the AIMD; iv) a fourth electrical connection 384 configured to be electrically connected to an AIMD control signal 382 disposed on the device side of the housing of the AIMD; and v) a switching POLE 399 configured to be controlled by the AIMD control signal to switch between a first THROW position and a second THROW position, wherein the switching POLE in the first THROW position electrically connects the first electrical connection with the second electrical connection wherein the third electrical connection is not electrically connected to the first electrical connection, and wherein the switching POLE in the second THROW position electrically connects the first electrical connection to the third electrical connection wherein the second electrical connection is not electrically connected to the first electrical connection; e) wherein the first filter capacitor is disposed on the device side, the first filter capacitor comprising at least one active electrode plate 272 disposed parallel and spaced from at least one ground electrode plate 273, wherein the at least one active and ground electrode plates are disposed within a capacitor dielectric 271; and f) wherein the at least one ground electrode plate of the first filter capacitor is electrically connected to the ferrule and/or housing of the AIMD.

In other exemplary embodiments, the first conductive pathway may be configured to be connected to a high-voltage shocking lead 150 disposed on the body fluid side. The AIMD may be an active implantable cardioverter defibrillator (ICD).

The first filter capacitor may be a two-terminal MLCC chip capacitor 288 comprising an active capacitor metallization 274 electrically connected to an at least one active electrode plate and in non-electrically conductive relation with an at least one ground electrode plate, and a ground capacitor metallization 275 electrically connected to an at least one ground electrode plate and in non-electrically conductive relation with an at least one active electrode plate. The first filter capacitor may also comprise a feedthrough capacitor 270, 284, a flat-thru (or flat-through) capacitor 614 or an X2Y attenuator 800. In all cases, there is at least one capacitor ground metallization 275 and at least one capacitor active metallization 274.

A second conductive pathway 181, 182 may be hermetically sealed to and disposed through the insulator between the body fluid side and the device side, the second conductive pathway being in non-electrically conductive relation with the ferrule. A second filter capacitor 270 may be disposed on the device side, the second filter capacitor comprising at least one active electrode plate 272 disposed parallel and spaced from at least one ground electrode plate 273, wherein the at least one active and ground electrode plates are disposed within a capacitor dielectric 271. The second conductive pathway may be electrically connected to the at least one active electrode plate of the second filter capacitor, and wherein the at least one ground electrode plate of the second filter capacitor is electrically connected to the ferrule. The second filter capacitor may be a feedthrough capacitor 284. Alternatively, the second filter capacitor may be a two-terminal MLCC chip capacitor 288.

The first filter capacitor and RF switch may be disposed upon a circuit board 387, the circuit board disposed on the device side.

The RF switch may be a SINGLE-POLE DOUBLE-THROW switch or a DOUBLE-POLE DOUBLE-THROW switch.

The RF Switch may have any number of poles or throws, that is n-POLES or n-THROWS.

As shown in FIG. 3A, the RF switch may comprise a fifth electrical connection 397 electrically connected to at least one of the ferrule and an AIMD housing thereby providing a switch ground.

As shown in FIG. 3B, the RF switch may comprise a fifth electrical connection 400 electrically connected to an AIMD control signal thereby providing a second electrical connection to an AIMD control signal.

As shown in FIG. 3C, the RF switch may comprise a fifth electrical connection 400 electrically connected to the AIMD control signal thereby providing a second electrical connection to the AIMD control signal, and a sixth electrical connection 401 electrically connected to the RF source thereby providing a second electrical connection to the RF source, and a seventh electrical connection 397 electrically connected to at least one of the ferrule and/or the AIMD housing thereby providing a switch ground.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 4 is an isometric view of the embodiment of FIG. 3 showing that the filter capacitor is grounded to a ferrule gold pocket-pad.

FIG. 4A is a portion of the isometric view of FIG. 4 showing the capacitor in a different mounting configuration.

FIG. 20 is Table 1 taken from the Haye's publication, which provides the Haye's EMI Class I, II and III criteria.

FIG. 22A illustrates the active and ground electrode plates of the filter capacitor of FIG. 22. The ground capacitor metallizations (terminations) are illustrated on the long ends of the rectangular capacitor. In this embodiment, the RF switches are positioned to accommodate grounding to the long-end ground capacitor metallizations.

FIG. 22B is an embodiment illustrating alternative active and ground electrode plate sizes for the filter capacitor of FIG. 22. Also illustrated are ground capacitor metallizations (terminations) on the short ends of the rectangular capacitor. In this embodiment, the RF switches are positioned to accommodate grounding to the short-end ground capacitor metallizations.

FIG. 33 is an isometric view of a quad polar flat-thru capacitor.

FIG. 34 illustrates the active and ground electrode plates of the flat-thru capacitor of FIG. 33.

DETAILED DESCRIPTION OF THE PREFERRED EMBODIMENTS

Figure 1:
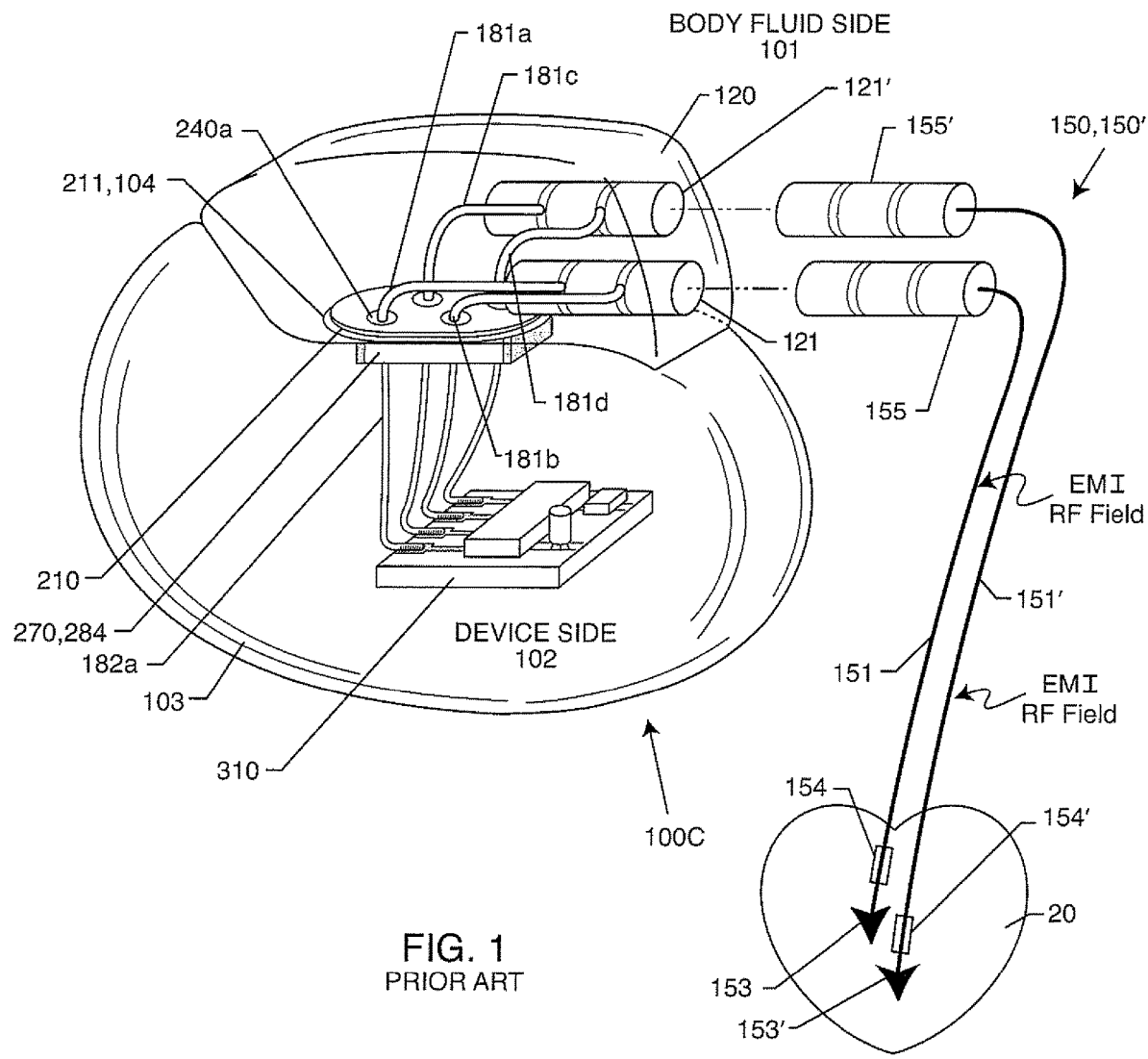
FIG. 1 is a prior art representation of a cardiac pacemaker connected to a heart of a patient.

FIG. 1 is a perspective view of an active implantable medical device (AIMD) known as a cardiac pacemaker 100C. The present invention is exemplary of implantable cardioverter defibrillators; however, the inventions of the present application apply in general to all the AIMDs of FIG. 41, including cardiac pacemakers, neurostimulators and the like.

Referring once again to FIG. 1, it is noted that cardioverter defibrillators and cardiac pacemakers have a lot in common. For example, one can see that the pacemaker 100C has a header block 120, which is typically made of a plastic material such as Tecothane™. The area of the header block is not hermetically sealed. There is a ferrule 210 and, in this case, four insulators 240a through 240d, which are hermetically sealed to the ferrule. The four insulators have four corresponding conductive pathways, which are illustrated in FIG. 1 as leadwires 181a through 181d. A hermetic feedthrough is defined herein as having one or more feedthrough conductive pathways, wherein the one or more feedthrough conductive pathways are selected from the group consisting of a terminal pin, a pin, a leadwire, a lead wire, a two-part pin, a lead conductor, a sintered paste-filled via, a co-sintered via, a co-sintered via with one or more metallic inserts, or combinations thereof. Additionally, a hermetic feedthrough typically comprises an electrically conductive ferrule comprising a ferrule opening extending to a ferrule body fluid side opposite a ferrule device side and an insulator residing in the ferrule opening where a gold braze hermetically seals the insulator to the ferrule. Typically, the ferrule is made of titanium and is laser welded 211 into the metallic housing 103 of the AIMD. The metallic housing 103 of a cardiac pacemaker is also typically of titanium. These conductive pathways on the device side of the hermetic feedthrough can terminate in AIMD ribbon cables, AIMD circuit boards, AIMD leadwires, AIMD thermal-sonic or ultrasonically bonded flat ribbons and the like. In other words, there are many ways to bring conductive pathways through hermetic terminals and route them through EMI filters or EMI filter circuit board and there are numerous ways to connect EMI filter circuit boards or feedthrough capacitors to AIMD electronic circuits.

The figures of the present application illustrate a ferrule, however, it is contemplated that any of the ferrules 210 could be eliminated, instead having an insulator 240 hermetically sealed directly to an opening of the AIMD housing (the opening of the AIMD housing 103 may be custom-formed to receive any insulator shape and/or design).

The insulators 240 of the hermetic feedthrough of the present application are shown hermetically sealed using a gold braze. In general, when the insulator is a ceramic, to hermetically seal the insulator to a metal, such as a ferrule 210 or a conductive pathway, using a braze material, one or more sputter layers are applied to the insulator surfaces to which the metal is to adhere in order to facilitate wetting of said braze material. In some embodiments, a first sputter layer is applied to the insulator surface, which is an adhesion layer. A second layer is applied over the adhesion layer, which is a wetting layer. In some embodiments, a single layer which has both adhesion and wetting properties is applied. For simplicity, the sputter layers are not shown in any of the figures herein. In general, hermetic seals of AIMD feedthroughs comprise a helium leak rate of at least $1 \times 10^{-7}$ std cc He/sec. Some embodiments comprise a glass hermetic seal or a glass-ceramic hermetic seal instead of a ceramic hermetic seal. The glass hermetic seal is typically a fused glass matched seal or a fused glass compression seal. The glass-ceramic seal may either be a brazed hermetic seal or a fused glass-ceramic hermetic seal. The glass or glass-ceramic seals may also be hermetically sealed directly to the ferrule 210 or the AIMD housing 103 of the AIMD.

The circuit board 310 of FIG. 1 is just a diagrammatic representation of an AIMD active electronics circuit board 310, which may contain many electronic components, including microprocessors, application specific integrated circuits (ASICs) and the like. Leadwires 182a through 182d are generally contiguous with leadwires 181a through 181d. In other words, the general element number 181 refers to the body fluid side portion of the leadwires 181a through 181d and 182 refers to the device side portion of the leadwires 182a through 182d. The device side is inside the AIMD housing 103 while the body fluid side is external of the AIMD housing 103. In FIG. 1, the body fluid side is generally labelled as 101, whereas the device side is generally labelled as 102.

Importantly, the AIMD housing 103 forms an electromagnetic shield thereby protecting sensitive electronic circuits on the circuit board 310 from direct penetration of external electromagnetic fields, also known as electromagnetic interference or EMI. Shown in FIG. 1, electromagnetic interference EMI can couple directly to the implanted leads 150, 150' which for a pacemaker, are generally routed transvenously along conductors 151, 151' to distal tip electrodes 153, 153' and distal ring electrodes 154, 154' that are disposed inside of the human heart 20. Typical cardiac pacemakers have one or more female connector ports 121, 121' formed in the header block into which proximal plugs 155, 155' are connected (inserted or plugged). For cardiac pacemaker and ICD applications, having removable plugs is very important as the leadwires 150, 150' and their associated electrodes 153, 153' and 154, 154' are typically implanted for many years (20 years or more). However, the pacemaker 100C has an internal primary battery and depending on whether it's providing constant pacing support or intermittent pacing support, it has a lifetime varying from 4 years to 8-12 years. In other words, AIMDs, also known as devices, go through what's known as device change outs much more frequently than the leads. On the device side, shown is a filter 270 that is an externally grounded feedthrough capacitor 284.

Figure 2:
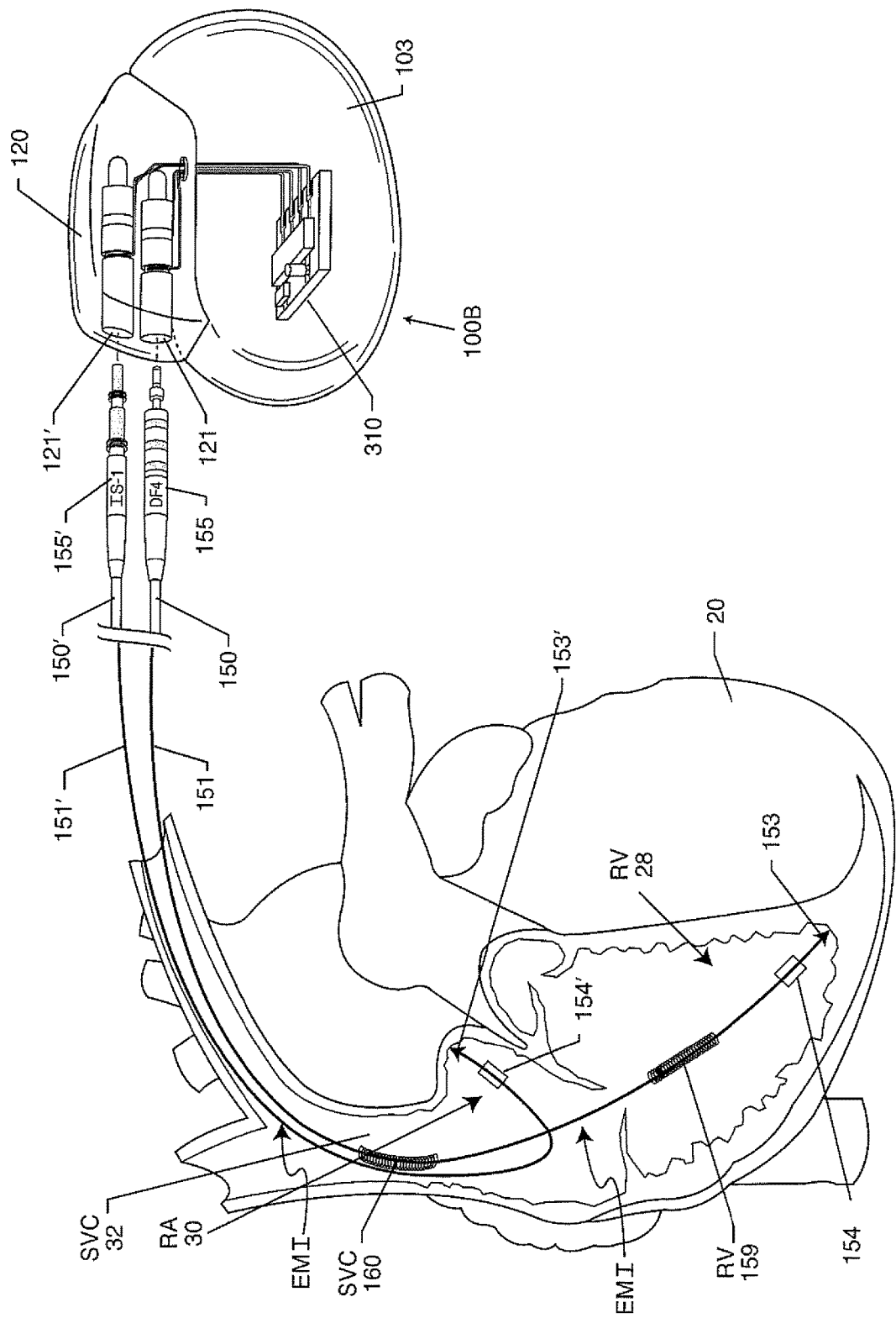
FIG. 2 is another prior art representation of an implantable cardioverter defibrillator connected to the heart of a patient.

FIG. 2 illustrates a sectional view of a human heart 20 and an AIMD known as an implantable cardioverter defibrillator 100B. In this case, the implantable cardioverter defibrillator or ICD is shown with a DF4 leadwire 150 routed to the right ventricle of the heart and the right atrium. In the industry, this is known as a dual-chambered device. Referring to the human heart 20 of FIG. 2, one can see that there are low-voltage electrodes 153 and 154 implanted into the right ventricle. These are known as tip and ring electrodes. There is also an IS-1 leadwire 150', which is a bipolar low-voltage lead that is routed into the right atrium 30, thereby providing pace and sense electrodes directly in the right atrium 30 (153' is the tip electrode and 154' is the ring electrode). The DF4 connector provides two high-voltage shocking circuits that run to a high-voltage shock electrode in the Superior Vena Cava (SVC) labeled as element 160. There is a second shocking electrode in the right ventricle (RV) labelled 159. It is not always the case that there are two shock electrodes because the ICD housing 103 can also be configured to be a shocking electrode, meaning that shocking vectors may be between the RV and the SVC or between either of the RV or the SVC and the AIMD housing. The shocking vectors are very important to properly cardiovert the heart in case it's having a dangerous ventricular arrhythmia, otherwise known as ventricular fibrillation. Ventricular fibrillation is immediately life-threatening and, as is commonly known from movies, is corrected when one has seen the external shocking paddles applied to a patient's chest. The ICD of FIG. 2 does the same thing but provides the high-voltage shocks internally to the heart. As illustrated in FIG. 2, EMI can also couple to these implanted leads through antenna action. In this case, the EMI can disrupt the proper operation of the pacemaker, but also could fool the ICD into thinking there was a dangerous ventricular arrhythmia, causing it to deliver what's known in the industry as an inappropriate high-voltage cardioversion shock. High-voltage cardioversion shocks are very painful to the patient and are highly undesirable.

Referring now back to FIG. 1, attention is drawn to the feedthrough EMI filter capacitor 270, 284, which is mounted adjacent to the ferrule 210 of the hermetic feedthrough. Feedthrough filter capacitors are well known in the prior art and are very effective at diverting undesirable EMI at the point of ingress into the AIMD housing 103 to the ferrule and, in turn, to the AIMD housing 103. The AIMD housing 103 forms a Faraday shield cage and becomes a system ground. Accordingly, these unwanted EMI signals are diverted to the AIMD shield housing 103 such that the EMI cannot interfere with sensitive electronic components on an AIMD circuit board 310.

Figure 3:
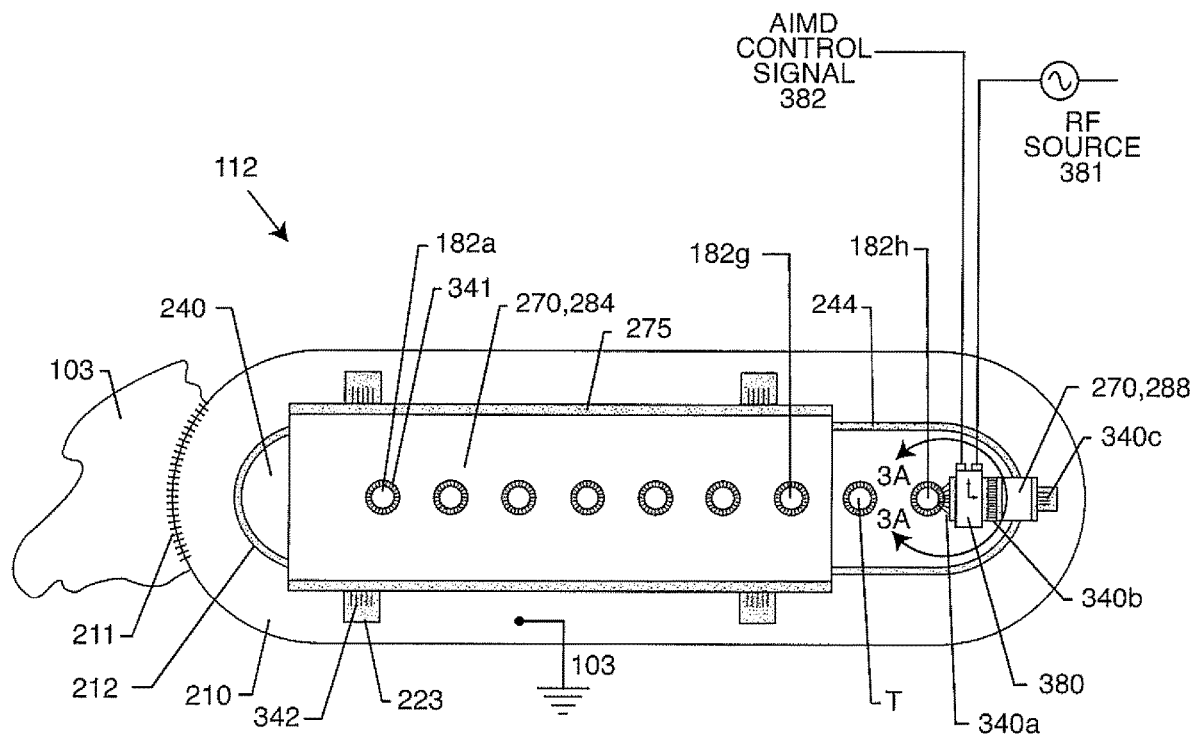
FIG. 3 is a top view of a novel embodiment of the present invention showing a switch disposed on the device side connected to a two-terminal MLCC chip capacitor.

FIG. 3 illustrates a top view of the device side of an AIMD hermetic feedthrough attached to an AIMD housing 103. Illustrated is a 7-POLE feedthrough filter capacitor 270, 284. The feedthrough filter capacitor is disposed over and/or adjacent to at least one of the ferrule 210 and the insulator 240 of the hermetic feedthrough. The insulator 240 is generally of either a ceramic (for example, alumina), a glass-ceramic or a glass seal, the insulator being hermetically sealed to the ferrule and the leadwires of the hermetic feedthrough. In the prior art, the feedthrough filter capacitor 270, 284 of FIG. 3 also encompasses a terminal pin 182*h*, which in this case, is a right ventricle high-voltage shocking lead. However, as previously disclosed, it is highly desirable to be able to test the right ventricle high-voltage shocking lead 182*h* and its associated electrodes with an RF source 381 (in other words, an RF test signal). By using an RF source 381 and measuring the reflective return signal known as $S_{1,1}$, inventors Swerdlow and Kroll teach that one can determine whether this critically important implanted lead is compromised, damaged or defective, for example, that the lead insulation is degraded, damaged, shorted and/or has defects. Compromised, damage or defective leads are very difficult to detect because this particular shocking coil is not always in direct contact with myocardial tissue. For example, the shocking coil 160 is literally floating in the blood pool in the Superior Vena Cava. Sometimes the shocking coil 160 (FIG. 2) is overgrown by what is called tissue encapsulation, but not always. Therefore, it is very hard to know in advance what the condition of the shocking coil 160 is until one tries to deliver a high-voltage shock, which means it might fail depending on the lead conductor's integrity.

As disclosed throughout the present application, the RF source 381 is used to dynamically analyze the electrical and physical integrity of implanted AIMD leads, particularly high-voltage shocking leads of an implantable cardioverter defibrillator (ICD). A reflective return signal $S_{1,1}$ from the RF source is measured and analyzed to identify electrical characteristics of the implanted AIMD lead, for example, identification of lead body anomalies, lead insulation defects or damage, inter-lumen insulation changes, lead conductor defects or damage and the like. The Swerdlow and Kroll patents, incorporated herein by reference, explain the RF interrogation signal and how it is used to analyze implanted lead defects. It is the RF switchable filtered feedthrough of the present invention that enables real-time assessment in an AIMD patient of the electrical and physical integrity of implanted AIMD leads. Such dynamic assessment of implanted AIMD lead integrity (enabled by the RF switchable filtered feedthrough of the present invention) provides programmable identification of impaired or damaged implanted AIMD leads, including implanted AIMD lead anomalies, lead body insulation defects or changes, and even defective, fractured or dislodged lead conductors. The RF switch(es) of the present invention can be programmed such that the AIMD can inject the RF lead interrogation signal $S_{1,1}$ at regular intervals, for example, hourly, daily or weekly and the like. Furthermore, such real-time identification of implanted lead integrity performance issues and/or failures are identified before a catastrophic patient event occurs as such issues and/or failures can cause therapy delivery malfunctions that can result in patient death. Before the RF switchable filtered feedthrough of the present invention, interrogating an implantable lead with the RF interrogation signal of Swerdlow and Kroll was only possible during AIMD change out (that is, change out of the pulse generator or the generator of the AIMD). This generator "change out" typically occurs every 5 to 7 years when the AIMD battery is depleted and the old AIMD is surgically removed and unplugged from the implanted AIMD leads (ref. ISO Standards, IS-1, DF-1 and DF4). At this time, once the AIMD generator is removed and the implanted lead proximal end connectors are left hanging out of the patient's pectoral pocket so that an external RF test signal generator can be connected for lead integrity interrogation. By removing the AIMD generator (which also removes the EMI filters of the AIMD), the RF test signal of the external RF test signal generator can then be injected into the proximal end of the implanted lead(s) hanging out of the pocket of the patient. It is noted that RF lead interrogation of an implanted AIMD system (implanted AIMD leads plugged into a generator) is not possible because the EMI filters within the AIMD attenuate the RF test signal, hence, there is no return signal to analyze implanted AIMD lead integrity. As a result, therefore, such testing of implanted AIMD leads only during generator changeout is not nearly frequent enough to timely identify damage or defect as an implanted AIMD lead can become damaged or defective at any time. Should, for example, the insulation of a patient's implanted high-voltage superior vena cava (SVC) shocking lead became damaged or defective approximately two years after implantation, and if this patient suffers a dangerous cardiac arrythmia such as ventricular fibrillation before the damage or defect can be identified, them the undetected reduction in the insulation resistance of the lead can cause a significant amount of the cardioversion shock energy to divert, which can be dangerous for the patient. A diversion of significant shock energy can result in a substantially degraded defibrillation shock vector that would not restore the heart to sinus rhythm. Not restoring the heart to sinus rhythm can cause death. Additionally, lead-related damage or defects can cause the ICD to fail to detect (sense) a dangerous arrythmia altogether. In either case, lack of timely identification of lead-related damage or defect can immediately be life-threatening to the patient. These and other issues are resolved by the RF switchable filtered feedthrough of the present invention, which allows RF interrogation of the implanted AIMD lead in real time.

FIG. 3 illustrates a novel way to provide both EMI filtering by an EMI filter capacitor and selective disconnection of the EMI filter from an AIMD circuit so that a connection can be made to an RF source 381 internal of the AIMD in order to make routine programmed integrity checks of an implanted SVC high-voltage shocking lead. As previously disclosed, Swerdlow and Kroll in their patents incorporated fully herein by reference teach how to use the RF signal, however, do not teach nor suggest any disclosure of how to also provide EMI protection for an AIMD system and its implanted lead. In other words, how to dynamically provide EMI protection to the RV shocking coils leadwire 182h during the lifetime of a generator of an AIMD system. A leadwire 182h can allow EMI to enter into the inside of an AIMD housing 103 in which one gets the highly undesirable effect known to EMI engineers as the "genie-in-the-bottle". What "genie-in-the-bottle" means is that once undesirable EMI energy is inside the AIMD housing, the EMI energy can cross-couple through either antenna action, mutual capacitance or mutual inductance to other circuits, such as sensitive sense circuits, which could disrupt the proper operation of either the pacemaker sensing circuits of the ICD, or worst yet, the high-voltage shocking circuits of the ICD.

Referring back to FIG. 3, illustrated is a novel RF switch 380. In the normal operating position, the RF switch 380 is connected to a filter capacitor 270, which in this embodiment is a two-terminal MLCC chip capacitor 288. Importantly, the two-terminal MLCC chip capacitor 288 is located very close to the RF switch and very close to the RV leadwire 182h, such that there is minimal undesirable inductance in the circuit. In other words, this allows the two-terminal MLCC chip capacitor 288 to be a very effective EMI filter. It is understood to those skilled in the art that the filter capacitor 270, 288 illustrated in FIG. 3 could be a two-terminal MLCC chip capacitor (multilayer ceramic capacitor), stacked tantalum, a two-terminal X2Y attenuator or any other two-terminal capacitor technology. It is understood that the physical locations of the RF switch 380 and the filter capacitor 270, 288 may be reversed (swapped) in position with no significant change of circuit function. These components may be swapped because the RF switch 380 and the filter capacitor 270, 288 are in a series circuit between the active terminal pin 182h and the ferrule 210, which is part of the system ground 103. In addition, the filter capacitor 270, 288 can be swapped because it presents a low impedance to the high frequency RF test signal 381, which means that the RF test signal is not significantly attenuated as it passes through the capacitor 270, 288 to the RF switch as shown in FIGS. 3A-3C or from the RF switch as shown in FIG. 3D.

In some embodiments, three-terminal feedthrough capacitors or the two-terminal MLCC capacitors (or X2Y attenuators or flat-thru capacitors) of the present invention would be designed for high power MRI applications and have a dielectric constant (k) of either less than 1,000 or less than 200. AIMD primary filter capacitors having a dielectric constant less than 200 are disclosed in U.S. Pat. Nos. 9,764,129 and 9,014,808, the contents of which are fully incorporated herein by reference. AIMD primary filter capacitors having a dielectric constant less than 1,000 are disclosed in U.S. Pat. No. 9,757,558, the contents of which are fully incorporated herein by reference. In another embodiment, the dielectric constant is 500, plus or minus 50. In yet another embodiment, the dielectric constant is 500, plus or minus 100.

Referring again to FIG. 3, one can see that there is a control signal 382 that comes from an AIMD circuit or internal circuit board such that the AIMD control signal can disconnect the RF switch from being in electrical contact with the two-terminal MLCC chip capacitor 270, 288, either at a pre-set interval or upon command, and connect the RF switch to an internal RF source 381. As previously disclosed, dis-connection of the filter capacitor is done for the purpose of testing the electrical integrity of an implanted AND lead. Importantly, testing of the implanted AIMD lead by the RF source 381 is generally for a period of a few milliseconds, but less than 1 second, so that during lead integrity testing there is very little chance of an EMI signal disrupting the internal AIMD electronic circuitry (see The Hayes Criteria FIG. 19).

Figure 3A:
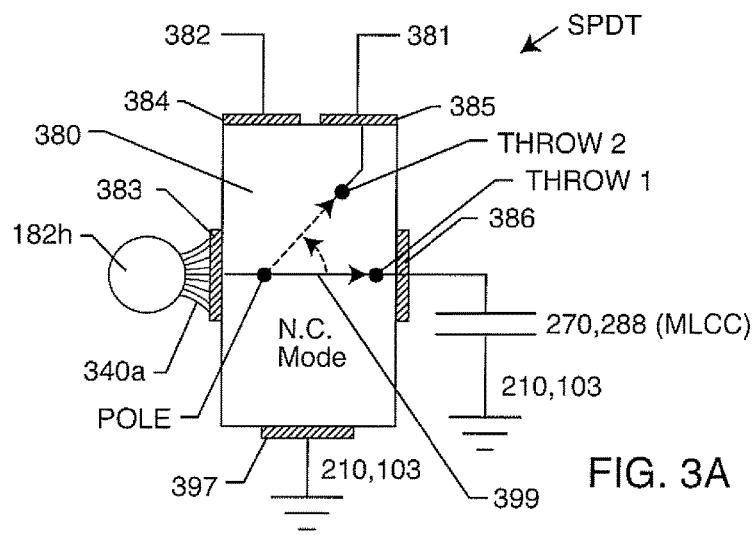
FIG. 3A is an enlarged view of the novel switch of FIG. 3.
Figure 3B:
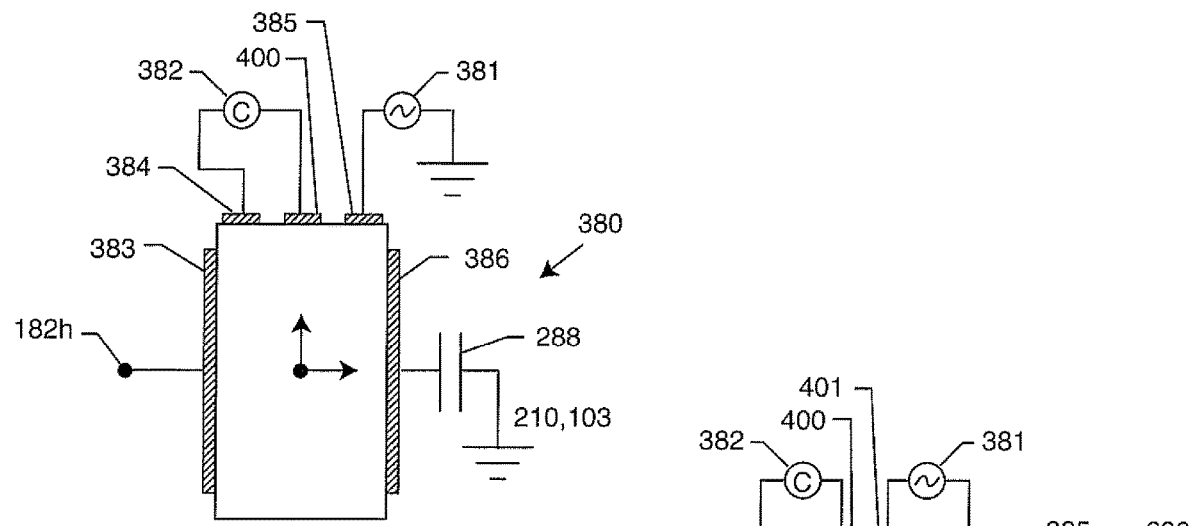
FIG. 3B is a view similar to FIG. 3A showing another embodiment of the novel RF switch.
Figure 3C:
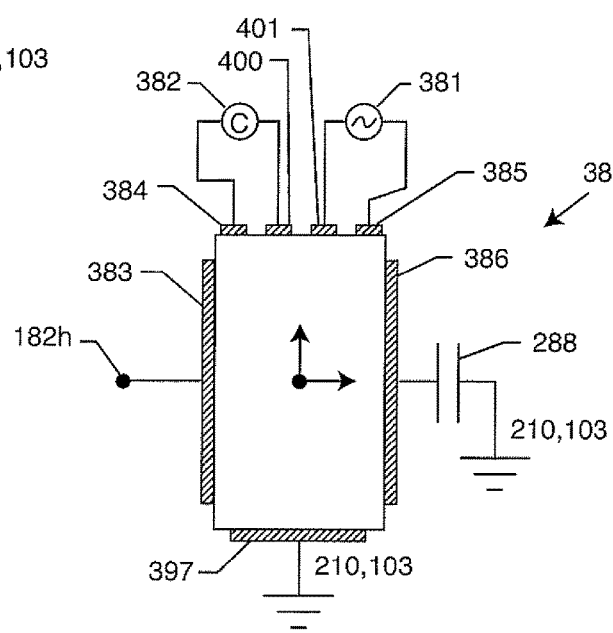
FIG. 3C is a view similar to FIG. 3A showing yet another embodiment of the novel RF switch.
Figure 3D:
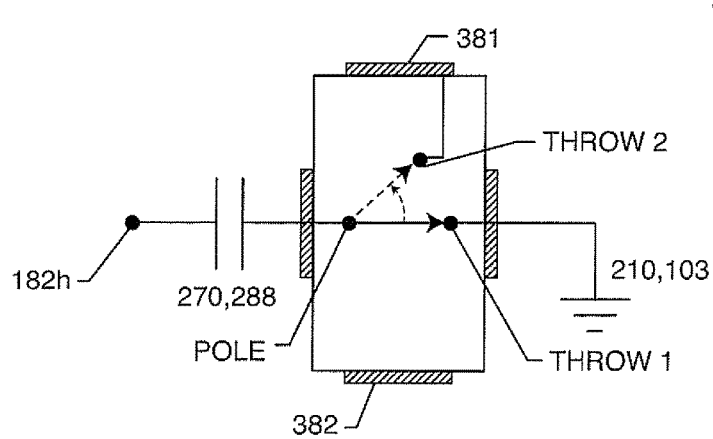
FIG. 3D is a view similar to FIG. 3A except that the RF switch has been moved to the ground side of the filter capacitor, which does not change circuit function.

FIG. 3A, which is an enlarged view taken from section 3A-3A of FIG. 3, shows the normally closed (N.C.) position of the RF switch 380. In this case, there is a switch POLE 399 with an arrow head. The switch POLE 399 of switch 380 is electrically connected to termination pad 383 and through electrical connection material 340a to the leadwire 182h. The N.C. position of the switch POLE 399 is shown as THROW 1. Once the RF switch 380 receives a control signal 382, internal circuits within the RF switch (not shown) direct the switch to move from its N.C. position THROW 1 to the dashed-line position indicated as THROW 2. Switching (toggling) from the THROW 1 position to the THROW 2 position disconnects the filter capacitor 270, 288 and, at the same time, electrically connects the leadwire 182h to the RF source 381 test signal circuit. To those skilled in the art, and in the vernacular of electronic switches, the RF switch 380 of FIG. 3A is known as a SINGLE-POLE DOUBLE-THROW (SPDT) switch.

Referring once again to FIG. 3A, with the RF switch 380 in the N.C. position THROW 1, if one attempts to inject an RF source 381 into the AIMD system, the RF test signal 381 would be diverted (filtered) by the filter capacitor 270, 288 to ground, that is the ferrule 210 attached to the AIMD housing 103 and/or an internal AIMD circuit board ground trace. In other words, the RF test signal 381 is not able to reach an implanted AIMD lead to test its integrity because the RF test signal 381 if filtered by the capacitor, so there is no useful $S_{1,1}$ return signal. The present invention solves this problem by disconnecting the filter capacitor 270, 288 while the RF test signal 381 is being delivered. At all other times (that is, when the RF switch is in the normally closed position), the filter capacitor 270, 288 is connected through the RF switch 380 to leadwire 182h to provide its vital EMI filtering function.

As shown in FIG. 3A, it is appreciated by those skilled in the art that RF switch 380 may include a termination 397, which is attached to a system ground, thereby providing a switch ground. The system ground comprises the ferrule, the AIMD housing and/or an AIMD internal circuit board ground trace.

FIG. 3B is an alternative embodiment of the RF switch 380 that includes a termination 400 electrically connected to the AIMD control signal providing a second electrical connection to the AIMD control signal 382, which is controlled on the circuit board inside the AIMD housing.

FIG. 3C is another embodiment of the RF switch 380 that includes the termination 400 of FIG. 3B and a termination 401 electrically connected to the RF source providing a second electrical connection to the RF source 381, which is controlled on the circuit board inside the AIMD housing. Additionally, illustrated is a termination 397 attached to a system ground thereby providing a switch ground, the system ground being the ferrule, the AIMD housing and/or an AIMD internal circuit board ground trace.

FIG. 3D is a schematic of the RF switch of FIG. 3A, however, FIG. 3D shows that the RF switch 380 and the filter capacitor 270, 288 are reversed (the positions of the RF switch and the filter capacitor are swapped). It is appreciated that the physical positions of the RF switches (390 or 502) and the filter capacitors 270, 288 may be reversed in various embodiments of the present invention.

All modern ICDs have at least one active electronics internal circuit board and/or at least one microprocessor or ASIC. In general, microprocessors are programmable, and are also reprogrammable, using what is known in the industry as an external programmer. It is the purpose of the RF telemetry pin T of an ICD to connect to an antenna in the header block 120 (not shown) of the device so that the ICD can communicate with an external programmer. In the present invention, the RF switch 380 is switched from its N.C. position connected to the filter capacitor 270, 288 to a position connected to the RF source 381 in response to a control signal received from ICD electronic circuits, which can be from an ICD internal circuit board. The control signal could be a DC bias, a digital signal or a low frequency AC signal. The RF switch control circuitry can be programmed or pre-set such that the control signal is sent at regular intervals (such as once or twice a day) to check the integrity of a lead conductor connected to the shocking coils of an ICD. Alternatively, the RF switch control circuitry could be programmed with an external programmer to perform a lead integrity test at other intervals (either more or less frequently). An additional optional feature is an "on demand control send signal", which allows an integrity test signal to be sent using an external programmer. For example, a healthcare provider can us an external programmer to perform a real-time lead integrity test "on demand" such as during a patient visit or when a patient presents to an emergency room.

It is understood that at the same time that the control signal is sent, the RF test signal as taught by Swerdlow and Kroll would also be activated. It will be appreciated that the present invention is also applicable to the older style close-coupled wanded telemetry devices; that is, where a magnetic coil (aka the hockey puck) is placed upon the patient's chest immediately over the ICD header block having a magnetic coil within. This older type of wanded telemetry is effective but has a much lower data transfer rate than the newer RF telemetry systems.

FIG. 4 is an enlarged view of the embodiment of FIG. 3. FIG. 4 illustrates the RF switch 380 attached to the two-terminal MLCC chip capacitor 270, 288. The two-terminal MLCC chip capacitor 270, 288 is electrically connected to a gold bond pocket-pad 223 using an electrical connection material 340c. The gold bond pocket-pad 223 comprises gold disposed within a ferrule pocket that is separate from the gold braze 244 forming the hermetic seal between the ferrule 210 and the insulator 240. One can also see an electrical connection material 340a electrically connecting the leadwire 182h to the RF switch 380. Additionally, there is an electrical connection material 340b electrically connecting the RF switch 380 and the active capacitor metallization 274 of the two-terminal MLCC chip capacitor 270, 288. For simplicity, the control wires connected to the RF source 381 and the control 382 of FIG. 4 (and FIG. 4A) are not shown.

FIG. 4A is similar to FIG. 4, except in this embodiment the two-terminal MLCC chip capacitor is flipped and is lying flat-side or flat-face down against the insulator and/or ferrule of the hermetic feedthrough. The two-terminal MLCC chip capacitors of both FIGS. 4 and 4A are metallized and configured such that they have very low resistance. Referring to FIG. 4A, the active capacitor metallization 274 of the filter capacitor is attached directly to the RF switch 380. The ground capacitor metallization 275 of the filter capacitor is electrically connected to a gold bond pad 223 using an electrical connection material 340c as shown. It is understood that oxide-resistant electrical ground connections include electrical connections to a pocket-pad of the ferrule, a metal addition to the ferrule, a gold braze of a hermetic feedthrough, a ground terminal pin laser welded or gold brazed to the ferrule, an oxide-resistant metal layer or area applied on a ferrule, or an ECA stripe overlaid atop an oxide-resistant metal layer or area of the ferrule. Gold pocket-pads and metal additions that provide an oxide-resistant ground connection for the filter capacitor 270, 288 are more fully disclosed in U.S. Patent Pub. No. 2018/0236244, the contents of which are fully incorporated herein by this reference. ECA stripes are disclosed in U.S. provisional application 62/979,600, the contents of which are fully incorporated herein by this reference.

Figure 4B:
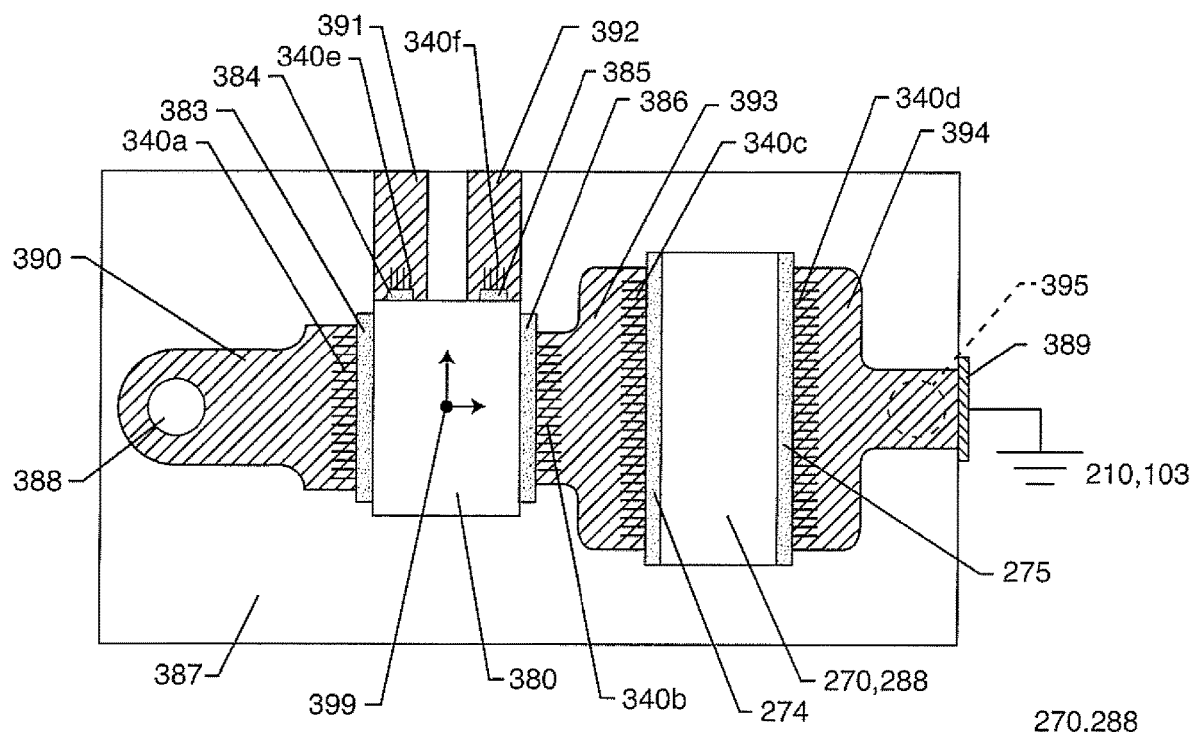
FIG. 4B is a view generally taken from FIG. 4 showing an embodiment of the RF switch and the filter capacitor mounted on a small circuit board.
Figure 4C:
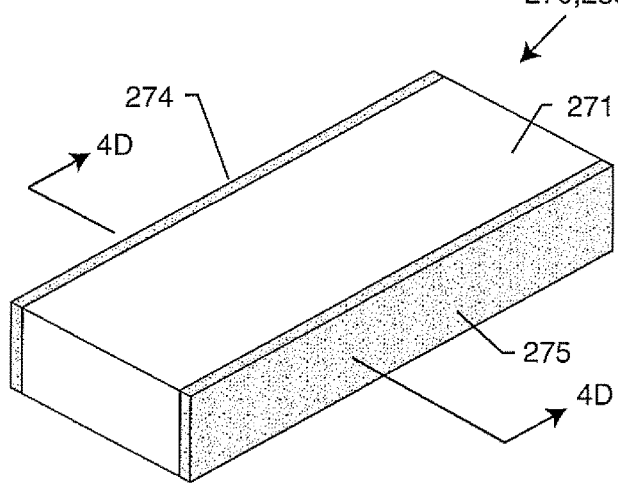
FIG. 4C is an isometric view of a reverse geometry two-terminal MLCC chip capacitor.

Referring once again to FIG. 4A, the two-terminal MLCC chip capacitor 270, 288 is laid down flat on its side. In the art, this two-terminal MLCC chip capacitor is known as a reverse geometry MLCC chip capacitor or a reverse geometry two-terminal MLCC chip capacitor because the active capacitor metallization 274 and ground capacitor metallization 275 are disposed along the long sides of the filter capacitor. Other prior art MLCC chip capacitors are typically metallized on their short ends, which provides two problems if used as shown herein. The first problem is that providing the metallization on the short ends means that the capacitor has a much higher internal inductance than a reverse geometry filter capacitor and, therefore, makes a poorer EMI filter at very high frequencies. Also, because of its narrow geometry, a reverse geometry two-terminal MLCC chip capacitor, as illustrated in FIGS. 4A through 4C, fits much better into the tight space between terminal pin 182h and the ferrule 210. However, reverse geometry filter capacitors (almost by definition) cannot be rated for very high voltages like ICD pulse voltages. This is because the active and ground capacitor metallizations (terminations) 274 and 275 (see FIG. 4C) are physically relatively much closer to each other, which results in the enhanced risk of high-voltage flashover or arcing. High-voltage flashover or arcing can be partially (but not entirely) mitigated by a conformal coating or an overcoat layer or blob of epoxy, which would at least partially relax the high voltage fields. It will be appreciated that conformal coatings of various insulative materials can be applied to any of the embodiments disclosed and illustrated herein. A very important and enabling embodiment of the present invention, which will be further disclosed later, is a strategic placement of RF switches such that a high-voltage ICD pulse is completely disconnected from the filter capacitors. This dis-connection particularly enables the reverse geometry filter capacitor embodiment of FIG. 4C.

Referring back to FIGS. 4 through 4G, the two-terminal MLCC chip capacitors 270, 288 are all reverse geometry two-terminal MLCC chip capacitors. It is noted that FIGS. 4 and 4E illustrate the reverse geometry two-terminal MLCC chip capacitor in a tombstone position. The tombstone position means that the electrode plates are disposed perpendicular to the device side surfaces of the insulator and/or ferrule. In this manner, the capacitor resembles the mounting of a tombstone, thus explaining the tombstone naming description.

It will also be appreciated that filter capacitors 284,600, 800 may be used in combination with the RF switch 380,502 to provide high frequency EMI filtering instead of or in addition to the two-terminal MLCC chip capacitors 270, 288. Exemplary alternate filter capacitors include three-terminal feedthrough capacitors, X2Y attenuators and flat-thru capacitors. Flat-thru capacitors 600 are more fully disclosed in U.S. Pat. No. 8,422,195, the contents of which are herein fully incorporated by this reference.

FIG. 4B illustrates that the RF switch 380 and two-terminal MLCC chip capacitor 270, 288 of FIGS. 4 and 4A could be first mounted on a circuit board 387. The circuit board 387 has circuit traces and lands disposed on its surface. Alternatively, the circuit traces could be disposed inside of a multilayer board. Via hole 388 is designed to be electrically connected to terminal pin 182*h*. The RF switch 380 is shown electrically connected using an electrical connection material 340*a* to the circuit trace land 390 of the circuit board. The RF switch 380 is also electrically connected to another circuit trace land 393, again, with electrical connection material 340*b*. Electrical connection material 340*c* connects land 393 to active capacitor metallization 274 of the two-terminal MLCC chip capacitor 270, 288. There is also another circuit trace 394, which is the ground circuit trace to which the ground termination 275 of the two-terminal MLCC chip capacitor is electrically connected with electrical connection material 340*d*. The ground circuit trace or land 394 is electrically connected to a circuit board edge metallization 389. This circuit board edge metallization is then connected to either a gold braze 244 or a gold pocket-pad 223 as previously illustrated in FIGS. 4 and 4A.

Referring once again to FIG. 4B, an optional ground electrical connection would be a via hole 395. In this case, an edge metallization on the circuit board 389 is not required. Via hole 395 is spatially oriented over either the gold braze 244 that forms the hermetic seal between the insulator 240 and the ferrule 210 or, it is disposed over an oxide-resistant gold pocket-pad 223. Via hole 395 is filled with an electrical connection material such as a thermal-setting conductive adhesive, a solder, and the like. Those skilled in the art will appreciate that instead of via holes 388 and 395, solid filled vias in the circuit board could be attached using BGA bumps, anisotropic conductive films or the like.

Referring back to FIG. 4B, the RF switch 380 has a location for a control wire 384 that is attached through electrical connection material 340*e* to a circuit board trace or land 391. There is also an electrical connection 340*f* to circuit trace 392, which would be for the RF test signal. Wires (not shown for simplicity) would connect from these lands 391 and 392 to, for example, an AIMD circuit board, which provides the control signal and the RF test signal. Electrical connection material 340*f* connects the RF source termination 385 to land 392.

FIG. 4C is an isometric view of a two-terminal MLCC chip capacitor 288.

Figure 4D:
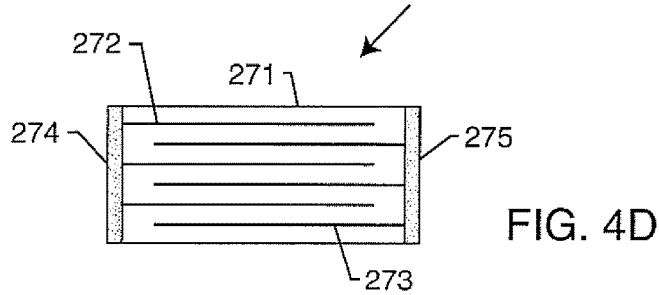
FIG. 4D is a sectional view taken along lines 4D-4D of FIG. 4C showing the internal electrodes of a filter capacitor.
Figure 4E:
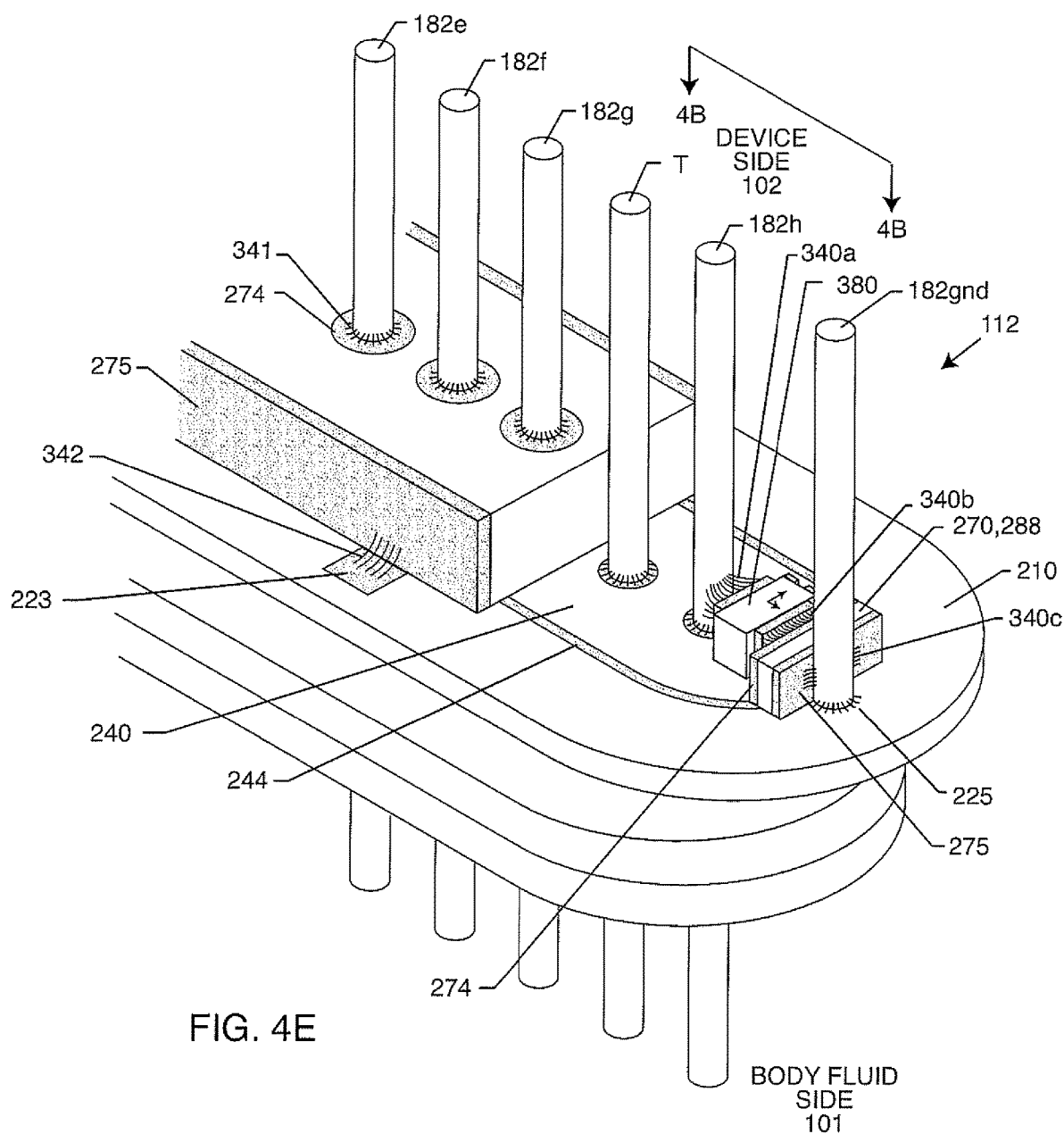
FIG. 4E is a perspective view similar to FIG. 4, except the filter capacitor is grounded to an oxide-resistant ground terminal pin attached to the ferrule of a hermetic feedthrough.

FIG. 4D is a sectional view taken along lines 4D-4D of FIG. 4C. The filter capacitor 288 has at least one active electrode plate 272 disposed in a capacitive relationship with at least one ground electrode plate 273. The electrode plates 272 and 273 are disposed within a capacitor dielectric 271. An active capacitor metallization 274 disposed on one side of the capacitor is electrically connected to the at least one active electrode plate 272. Similarly, a ground capacitor metallization 275 disposed on another side of the capacitor is electrically connected to the at least one ground electrode plate 273. It is understood by those skilled in the art that what is considered the active and ground sides is how the MLCC chip capacitor is mounted when in use, as the capacitor can be flipped around and work just the same. The at least one ground electrode plate 273 and the at least one active electrode plate 272 are interleaved (sandwiched) in a capacitive relationship.

FIG. 4E is similar to FIG. 4, except that the two-terminal MLCC capacitor 270, 288 is grounded to an oxide-resistant ground terminal pin 182*gnd* as shown. This ground terminal pin is either laser welded 225 directly to the ferrule 210 or gold brazed 225' into a hole of the ferrule 210. The ground capacitor termination is electrically connected to the ground terminal pin using an electrical connection material 340*c* such as a solder or thermal setting conductive adhesive. This ground terminal pin may be conveniently routed to an AIMD electronic circuit board (not shown), thereby providing an AIMD housing ground to the circuit board. Implantable cardioverter defibrillators (ICDs) can use what is known in the industry as a "hot-can" approach. This means that the AIMD housing 103 can be used as a high-voltage shock electrode. Thereby, the circuit board could divert a high-voltage biphasic pulse to the ground terminal pin, which results in a hot-can. With this approach, the opposite polarity of the high-voltage biphasic pulse can be applied to terminal pin 182*h* with the pulse return through 182*gnd*.

Figure 4F:
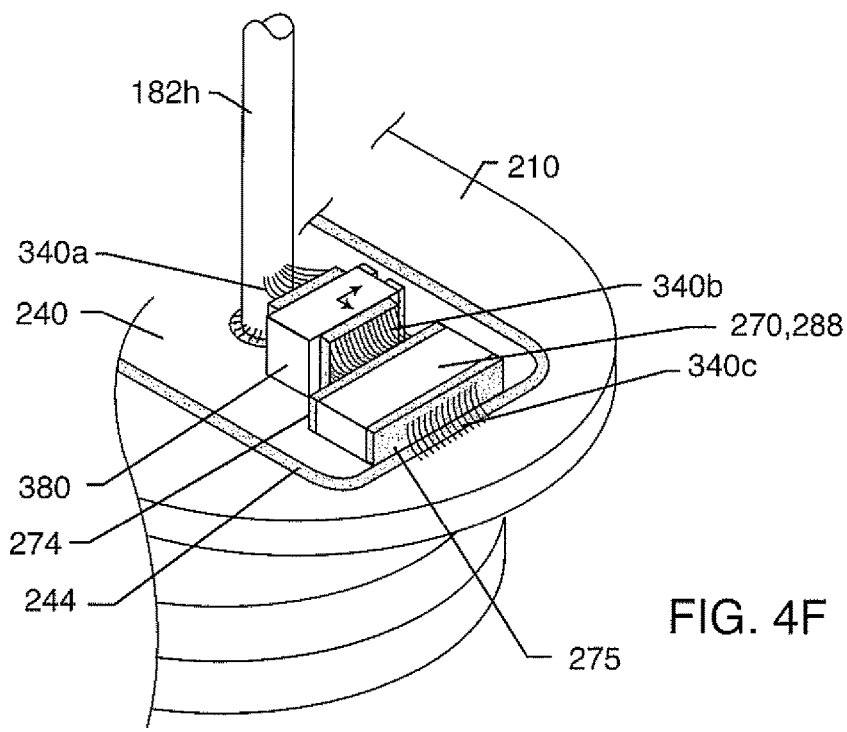
FIG. 4F is a portion of the isometric view of FIG. 4E, showing that the filter capacitor is grounded to an oxide-resistant gold braze hermetically sealing the insulator and the ferrule.

FIG. 4F is also similar to FIG. 4, illustrating yet another embodiment for grounding the filter capacitor 270, 288 to the oxide-resistant gold braze hermetically sealing the ferrule and the insulator. In this case, the electrical connection material 340*c* is between the capacitor ground metallization (or termination) and the gold braze 244 of the hermetic seal between the hermetic seal insulator 240 and the ferrule 210.

Figure 4G:
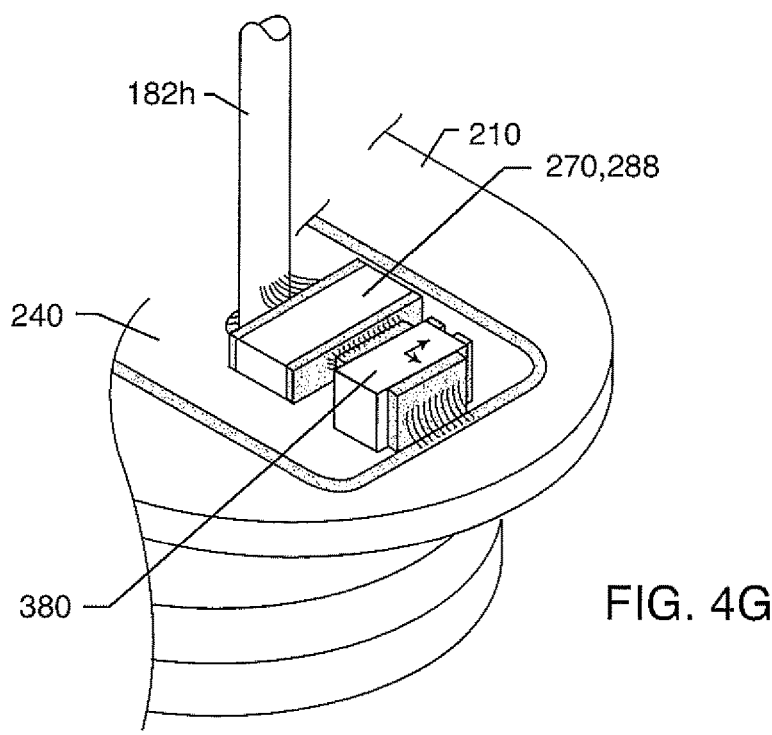
FIG. 4G is similar to FIG. 4F except that the positions of the RF switch and the filter capacitor have been reversed, which does not affect circuit performance.

FIG. 4G is the same as FIG. 4F except that the locations of the RF switch 380 and the filter capacitor 270, 288 are physically reversed (swapped in location). Physically reversing the locations of the RF switch 380 and the filter capacitor 270, 288 does not change or affect the RF switch circuit function.

Figure 5:
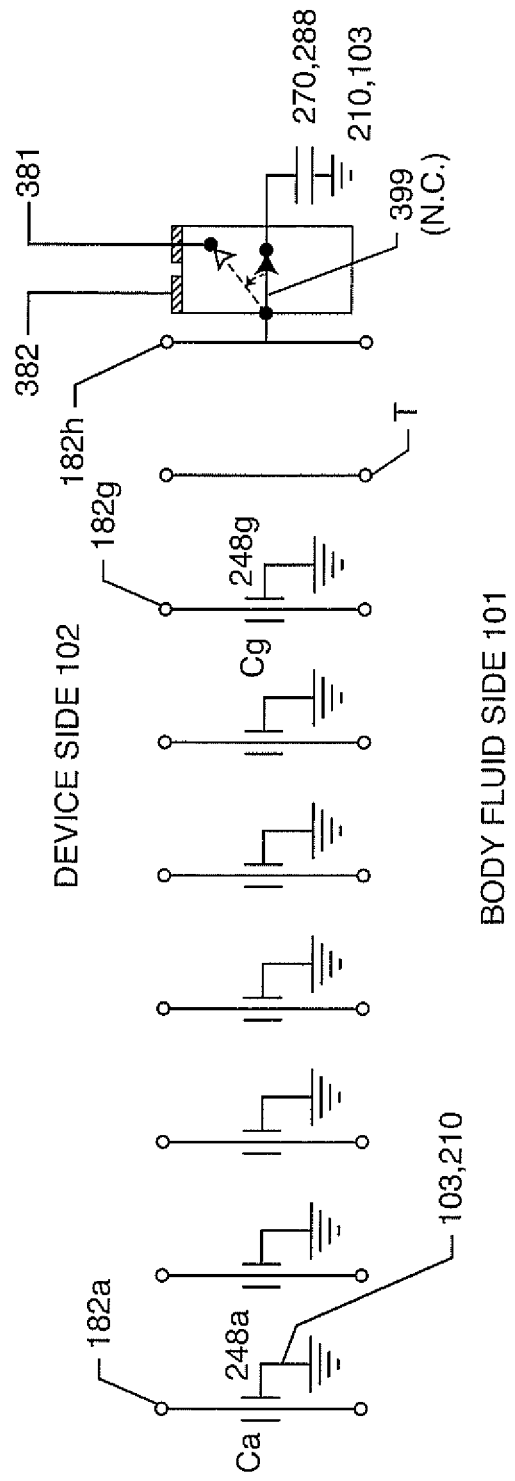
FIG. 5 is an electrical schematic of FIG. 4.

FIG. 5 is an electrical schematic of the filtered hermetic terminals and RF switches previously illustrated in FIGS. 3 and 4. The RF telemetry pin T is not filtered. Terminal pins

182a through 182g are filtered as they pass through the filter capacitor 270, 288. Importantly, FIG. 5 shows the schematic for terminal pin 182h, which is a high-voltage shocking lead that is connected to the RF switch and in turn, to the filtered capacitor 270, 288. Control wire 382 is indicated as well as the RF signal source wire 381.

Referring once again to FIGS. 4, 4A, 4B, 4E, 4F and 4G, the AIMD ASIC control signal 382 disconnects the filter capacitor 270, 288 from the RF switch 380 and, instead, connects the RF switch to the RF interrogation signal. In an embodiment, the RF switch 380 of the present invention does not necessarily have to be associated with a Swerdlow and Kroll RF implanted lead interrogation signal. In this embodiment, the AIMD is programmed such that the AIMD electronic circuits (ASIC electronics) send a control signal 382 to disconnect the RF switch(es) from the filter capacitors upon detection of a dangerous cardiac arrhythmia and then to deliver a high-voltage shock pulse to correct the arrhythmia (see disclosure and teachings herein regarding series capacitance when a common ground plane or electrode is also not disconnected). An advantage of this embodiment is that the filter capacitor 270, 288 is not fully exposed to the high-voltage therapy delivery pulse, therefore, a low-voltage filter capacitor can be used. Furthermore, a low-voltage filter capacitor 270, 288 also does not have to be pulse current rated as dis-connection removes the need. This means the capacitor could be much smaller in size and much less expensive. In summary, an embodiment of the present invention is to disconnect the filter capacitor 270, 288 during ICD pulse delivery.

As will be explained and shown in various other embodiments, it is also desirable to use RF switches to: 1) disconnect the HV SVC and RV filter capacitors 270, 288 from system ground 210, 103 and; 2) at the same time, also disconnect these HV SVC and RV filter capacitors 270, 288 from any common ground electrode or circuit board ground plate(s) 396 in order to eliminate HV pin to pin series capacitance. It is noted that, when the filter capacitors are disconnected from common ground and also from each other (through any common ground connection), then these filter capacitors are not exposed at all to the ICD high voltage shock of an ICD pulse and are also not exposed at all to capacitor ICD pulse inrush currents. Consequently, disconnection of the filter capacitors enables the use of common low-voltage capacitors that do not need to be rated for pulse inrush currents at all.

Figure 6:
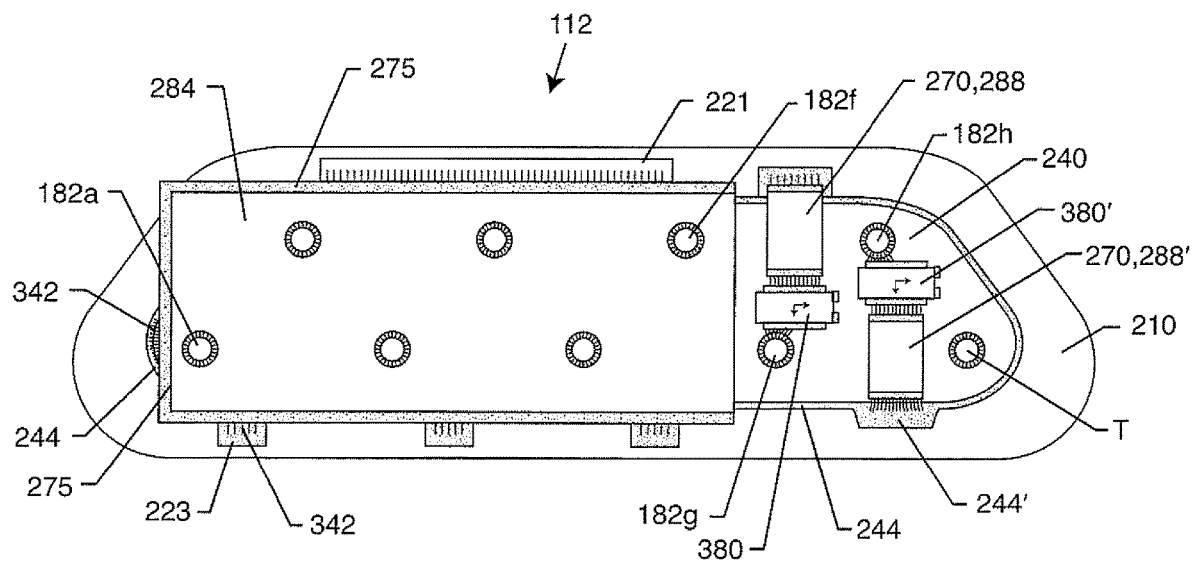
FIG. 6 is an embodiment of the present invention showing two novel RF switches and two two-terminal MLCC chip capacitors of the present invention. The RF switches disconnect the two-terminal MLCC chip capacitors from common ground and also disconnect the series common ground circuit between the two two-terminal MLCC chip capacitors.
Figure 6A:
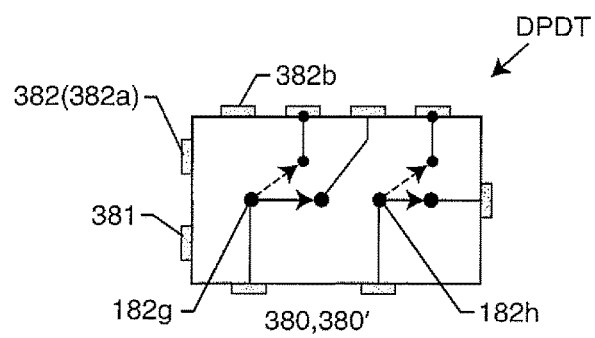
FIG. 6A is an enlarged view of a DOUBLE-POLE DOUBLE-THROW RF switch that can be used in lieu of the two RF switches of FIG. 6.

FIG. 6 is similar to FIGS. 3 and 4, except in this case, there are two RF switches 380 and 380'. There are also two two-terminal MLCC chip capacitors 270, 288 and 270, 288'. In the configuration shown in FIG. 6, this would be in the case where there are shocking electrodes disposed in two locations of the heart, such as the Superior Vena Cava (SCV) 32. So, in this example, leadwire 182g could be connected to the right ventricle 28 shocking coil 159 and leadwire 182h could be electrically connected to the SVC shocking coil 160, which is located above the right atrium 30. It will be appreciated that in FIG. 6, with some minor dimensional adjustments, the RF switch 380 and 380' can be combined into a single RF switch, which is known in the industry as a DOUBLE-POLE DOUBLE-THROW (DPDT) RF switch. A DOUBLE-POLE DOUBLE-THROW RF switch is schematically illustrated in FIG. 6A. The advantage of integrating both switches into a single module is that only one control wire and one other RF source wire 382 is needed to throw both switches simultaneously. While FIG. 6 shows two shocking coil leads, it is appreciated that the present invention can be used with any number of shocking leads.

Referring once again to FIG. 6, it is appreciated that the two two-terminal MLCC chip capacitors 288 and 288' could be integrated into a single monolithic structure.

Referring again to FIG. 6A, it will be appreciated throughout this invention that the RF switch 380 (SPDT, DPDT and other multiple POLE switches) have to be either grounded or provided with two control wires 382a and 382b, such that the control signal and RF source are properly biased.

Referring back to FIGS. 4, 4A, 4B, 4E, 4F and 4G, in this case, there is only one high-voltage shocking lead 182h, which can be directed to either a right ventricle shocking electrode or a superior vena cava shocking electrode.

Referring now to FIG. 6, illustrated are two high-voltage shocking leads 182g and 182h, which is typical for a superior vena cava (SVC) shocking electrode and a right ventricular (RV) shocking electrode. In an embodiment, the RF switches 380 and 380' disconnect both of the filter capacitors 270, 288 that are associated with the two high-voltage shocking circuits 182g and 182h, which is defined herein as "complete capacitor dis-connection". As previously disclosed, by disconnecting both of the filter capacitors from the high-voltage shock circuit and from common ground 210, neither of these high-voltage shock circuit filter capacitors are subjected to the high-voltage therapy delivery pulse, therefore do not need to be high-voltage pulse-rated capacitors. In other words, when the AIMD electronics (ASIC electronics) are programmed to send a control signal 382 to open the switches 380 during an ICD pulse, much smaller and less expensive filter capacitors 270, 288 and 270, 288' can be used. Disconnecting the filter capacitors 270, 288 completely, meaning from both system ground 210, 103 and from each other, form another embodiment which allows the Swerdlow and Kroll lead integrity control signal 381 to be injected. These are separate embodiments which involve ASIC programming as it would not be desirable to deliver a high voltage ICD shock at the same time that an implanted lead(s) was being interrogated by the RF test signal 381.

Figure 7:
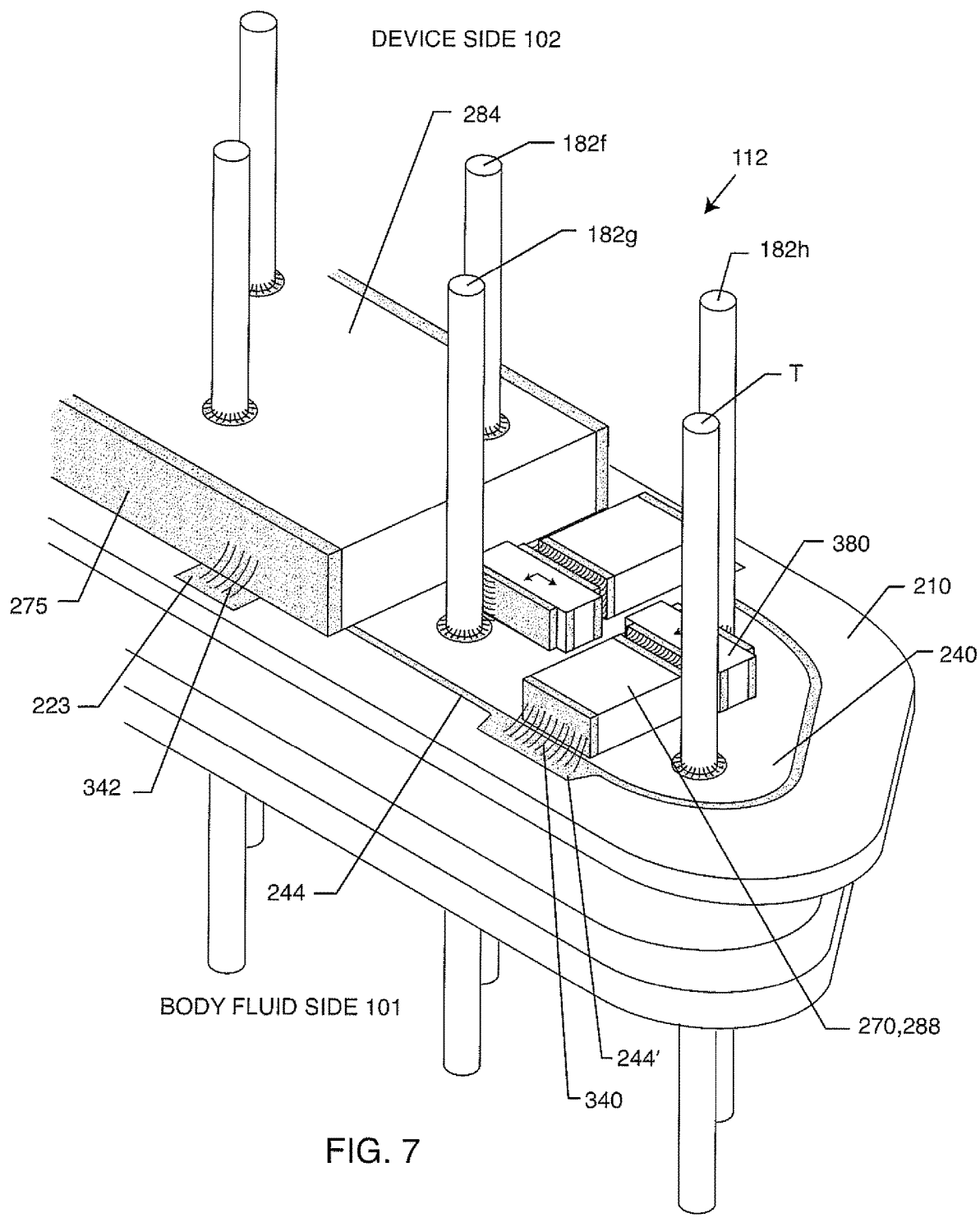
FIG. 7 is an isometric view of the embodiment of FIG. 6.

FIG. 7 is an isometric view of the structure illustrated in FIG. 6. In this embodiment, rather than using a gold pocket-pad, the gold braze hermetic seal 244 has been extended out at location area 244'. This location area 244' can be a thin layer of gold braze that facilitates the use of an electrically conductive material 340 for attachment.

Referring back to FIG. 6, one can see that a metal addition 221 has been laser welded to the ferrule 210. The metal addition 221 is of a material that is different from the ferrule and helps provide an oxide-resistant material for electrical attachment. Also shown in FIG. 6 is that the outside ground capacitor metallization 275 is disposed on the left-hand side of the capacitor 284, which allows yet another electrical connection to the gold braze 244 hermetically sealing the insulator to the ferrule thereby providing a lower inductance connection and improving filter performance. For more information regarding metal additions connected to a ferrule, one is referred to U.S. Pat. No. 9,931,514, the contents of which are fully incorporated herein by this reference.

Figure 8:
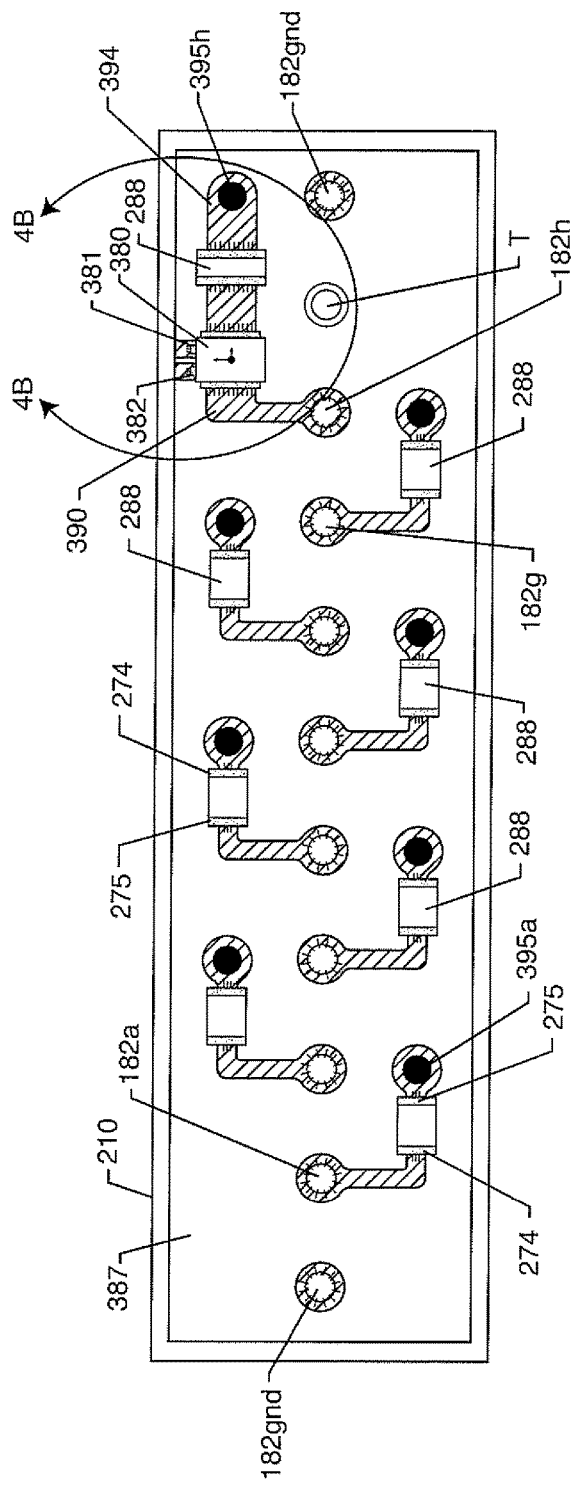
FIG. 8 is a top view similar to FIGS. 3, 4B and 6 but showing another embodiment of a circuit board having the novel RF switch of the present invention and a plurality of two-terminal MLCC chip capacitors disposed thereon to filter EMI.
Figure 8A:
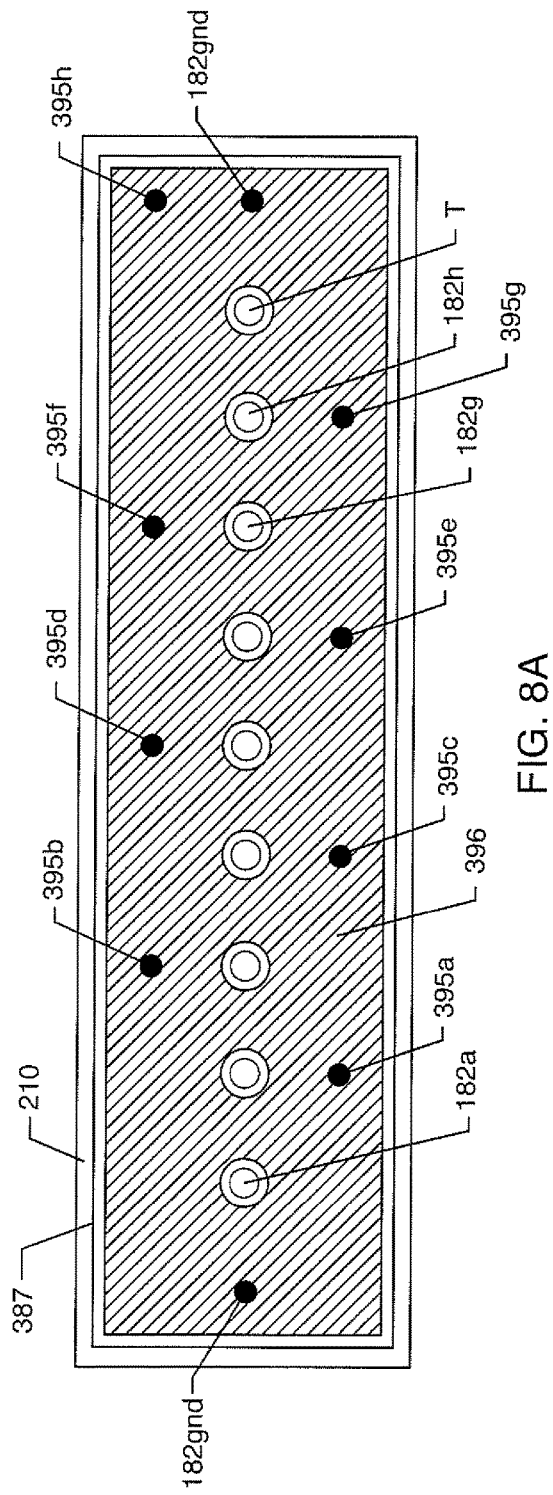
FIG. 8A is a top view of a ground electrode plate disposed within or on the circuit board of FIG. 8, the ground electrode plate grounding the plurality of two-terminal MLCC chip capacitors and the RF switch to the ferrule of the hermetic feedthrough.

FIG. 8 illustrates another embodiment of the present invention comprising a circuit board 387 supporting a plurality of two-terminal MLCC chip capacitors 288. The circuit board may be disposed on at least one of the insulator or the ferrule of the device side of the hermetic feedthrough as shown. Alternatively, the circuit board may be disposed spaced away from the insulator or the ferrule of the device side of the hermetic feedthrough. It is understood, therefore, that the circuit board may be disposed on, adjacent, near, or even far from the insulator or the ferrule of the device side of the hermetic feedthrough. Regardless, in all cases, the circuit board is disposed inside the AIMD housing. In this embodiment, the feedthrough filter capacitor 270, 284 has been eliminated. Instead, two-terminal MLCC chip capacitors 288 are disposed adjacent to each of the active leadwires 182a through 182g. The active capacitor metallization 274 of each of the two-terminal MLCC chip capacitors 288 is electrically connected through a circuit trace and via hole to the respective leadwires 182a through 182g. It is understood by those skilled in the art that the circuit traces are optional. Instead, the two-terminal MLCC chip capacitors 288 can be rotated such that they make direct contact with their respective leadwire 182a and ground via hole 395. The ground capacitor metallization 275 of the two-terminal MLCC chip capacitors is electrically connected to a ground via hole 395, which may be a metallized through-fill or a conductive material filled via hole. These ground via holes 395 are connected to at least one internal circuit board ground plate 396, which is best illustrated in FIG. 8A. The ground plate, in this case, is grounded through two ground pins 182gnd that are either gold brazed or laser welded to the ferrule 210. It will be appreciated that one, two or even "n" number of ground pins 182gnd can be used such that the ground plate has minimal inductance. As shown, the ground plate 396 has minimal inductance along its length. This is important to ensure that each of the filters 288 has proper high-frequency performance (insertion loss).

For more information regarding circuit board ferrule ground pins, one is referred to U.S. Pat. No. 8,195,295 (in particular FIG. 83), the contents of which are fully incorporated herein by this reference. In accordance with the teachings of U.S. Pat. No. 8,195,295, the circuit board ground plate or ground trace may be: (1) edge grounded to the insulator or ferrule gold braze as shown in FIGS. 54-56; (2) grounded through a via hole to the hermetic seal gold braze as shown in FIGS. 88-93; (3) grounded through a closed via hole to the hermetic seal gold braze as shown in FIG. 94; (4) grounded to a pin laser welded to the ferrule as shown in FIG. 95; (5) grounded to a pin which is gold brazed to the ferrule as shown in FIG. 96; (6) attached to a ferrule projection as shown in FIG. 97; or (7) grounded via a grounding ring as taught in FIGS. 101 and 102.

Referring once again to FIG. 8, it is noted that the two-terminal MLCC chip capacitors 288 associated with terminal pins 182a through 182g are terminated on their short ends as regular geometry two-terminal MLCC chip capacitors. According to the present invention, however, it is understood that the two-terminal MLCC chip capacitors 288 are preferably reverse geometry filter capacitors (see FIG. 4C) as shown for the filter capacitor 288 that is associated with terminal pin 182h that is terminated on their long ends and also as illustrated in FIG. 4A. Referring once again to FIG. 8 the two-terminal MLCC chip capacitor 288 that is associated with the RF switch 380 (182h) is shown having a reverse geometry. For more information on reverse geometry filter capacitors and other two-terminal MLCC chip capacitor mounting techniques, one is referred to FIGS. 22-24 of U.S. Pat. No. 8,195,295 where FIG. 24 shows a reverse geometry two-terminal MLCC chip capacitor with very low inductance $L_3$. The circuit traces of the circuit board of FIG. 8 have been drawn relatively long for simplicity, but it is appreciated that the circuit traces 390,393, 394 should be as short as possible to minimize undesirable inductance. Undesirable series inductance degrades filter performance at very high frequencies, such as cellular telephone frequencies.

In general, reverse geometry MLCC capacitors (FIG. 4C) have much lower parasitic conductance and therefore, provide superior EMI filtering at high frequencies.

FIG. 8A shows an internal ground plate of the circuit board of FIG. 8. It is understood that the internal ground plate of FIG. 8A could comprise a plurality of ground plates or even be an external ground plate or circuit trace. In a preferred embodiment the internal ground plate is disposed between at least one of the insulator 240 and/or the ferrule 210. The purpose of the ground plate(s) is to shield the RF opening created by insulator 240 thereby preventing direct penetration of radiated electromagnetic interference into the interior of the ICD. These ground plate principles are more clearly taught in U.S. Pat. No. 8,192,295.

Referring now back to FIGS. 8 and 8A, it is apparent that the RF telemetry pin T is not associated with a filter capacitor (RF telemetry pins cannot be filtered or else they would not function properly). Now referring to leadwire 182h of FIG. 8, the RF switch 380 of the present invention is electrically connected to the two-terminal MLCC chip capacitor 288, which in turn is connected to the ground plate 396, in this embodiment, through a circuit trace. This portion of the circuit board 387 has already been disclosed in more detail with reference to FIG. 4B.

Referring once again to FIG. 8, shown is the device side of a conductive pathway 182h. As previously disclosed, this conductive pathway may comprise a terminal pin 181, 182 that is hermetically sealed and passes through the insulator of the hermetic feedthrough in non-conductive relation with the ferrule. Terminal pin 181, 182 can alternatively comprise a two-part pin as disclosed in U.S. Pat. No. 10,272,252, the contents of which are fully incorporated herein by this reference. The conductive pathway of FIG. 8 can also comprise a co-sintered paste-filled via (see FIG. 36 herein). Co-sintered paste-filled vias are disclosed in U.S. Pat. Nos. 8,653,384; 8,938,309; 9,233,253; 9,352,150; 9,889,306; 9,993,650; 10,249,415; and 10,500,402, the contents of which are fully incorporated herein by these references. Alternative methods of providing an oxide-free ground electrical connection to the ferrule are disclosed in U.S. Pat. Nos. 6,765,779; 6,765,780; 9,931,514; and 10,350,421, the contents of which are also fully incorporated herein by these references.

Referring once again to FIG. 8, for an ICD application, terminal pins 182a through 182g are low-voltage active terminal pins for sensing and pacing while terminal pin 182h is a high-voltage active terminal pin, meaning that the high-voltage active terminal pin 182h is connectable to at least one body fluid side defibrillation electrode (which can also sense). One high-voltage active terminal pin 182h is shown for simplicity but it is appreciated that there can be a plurality of high-voltage active terminal pins. The plurality of high-voltage active terminal pins may comprise, for example, at least two high-voltage active terminal pins as shown in FIG. 2, that is, one high-voltage active terminal pin for electrical connection to a right ventricle (RV) defibrillation electrode 159 and a second high-voltage active terminal pin for electrically connecting to a superior vena cava (SVC) shocking electrode 160.

As previously disclosed, it is an advantage to completely or at least partially disconnect the high-voltage filter capacitor 288 associated with terminal pin 182h during delivery of an ICD shock. Complete dis-connection means that the filter capacitor 288 is not exposed to high-voltage shock pulses or capacitor inrush currents $i_c$ which therefore allows optional use of low-voltage common (not pulse-rated) filter capacitors, which are typically smaller in size and are also more commonly available.

Figure 9:
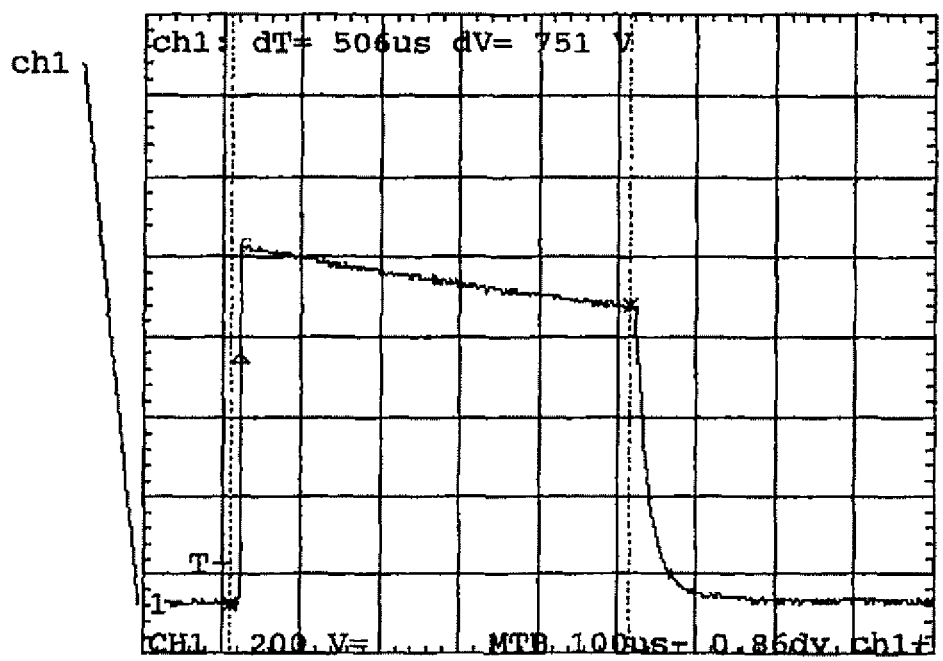
FIG. 9 is an oscilloscope screen capture of an ICD monophasic shock voltage waveform into a resistive load during high-voltage therapy delivery.

FIG. 9 is an oscilloscope screen capture of an HV defibrillation shock waveform into a resistive load during ICD therapy delivery. The resistive load on the ICD in-vivo is characteristic of the resistance of the heart myocardial tissue (around 500 ohms) to the cardiac stimulation pulse. As FIG. 9 illustrates, the delta voltage dV is equal to 751 volts. Modern ICDs deliver defibrillation shock voltages at even higher voltages, such as from 750 volts to on the order of 1 kilovolt. However, when a filter capacitor, such as the two-terminal MLCC chip capacitor 288 of FIG. 8, is added to the ICD HV output circuit, how the circuitry functions changes. These filter capacitors may include feedthrough filter capacitors 270, 284 (three-terminal devices) or MLCC capacitors 288 (two-terminal devices). X2Y attenuators 800 (FIG. 35) or flat-thru capacitors 600 (FIG. 30) may also be used for the filter capacitor 270, 284, 288 as previously disclosed in U.S. Pat. Nos. 8,195,295; 8,095,224; 8,321,032; 8,437,865; 8,433,410; 8,483,840; 8,670,841; 8,712,544; 8,716,895; 8,868,189; 8,918,189; 8,996,126; 9,031,670; 9,071,221; 9,463,329; 9,895,534; 10,016,595; 10,016,596; 10,080,889; 10,099,051; and 10,124,164; and U.S. patent application Ser. Nos. 16/364,953; 16/385,338; 16/435,600; 16/452,785; and Ser. No. 16/809,676; the contents of which are herein fully incorporated by these references. The filter capacitors 270, 284, 288, 600, 800 generally compromise monolithic ceramic construction but may also comprise stacked film, tantalum, aluminum electrolytic, and any other type of capacitor technology.

The capacitance values of AIMD filter capacitors 270, 284, 288, 600, 800 generally range from tens or hundreds of picofarads up to thousands of picofarads. Common values for primary AIMD filters range from 400 picofarads up to 10,000 picofarads. Average values for ICD filter capacitors range from about 1200 picofarads to 1800 picofarads. Filter capacitance values also vary due to manufacturing tolerances and/or because of capacitor aging (ceramic capacitors have an aging rate in which the capacitance value drops over time). For comparative and/or representative purposes, the calculations herein use an exemplary filter capacitance value of 1500 picofarads.

Further regarding AIMD filter capacitors, it is noted that, before the ICD can deliver high-voltage shock therapy, the ICD must first charge the filter two-terminal MLCC chip capacitor 288, which is initially in an uncharged state. As such, the circuit changes from an idealized resistive load of the ICD HV defibrillation shock waveform to that of an uncharged capacitor. It is well known to electrical engineers that one cannot change the voltage on a capacitor instantaneously.

Additionally, there is parasitic resistance and inductance in the circuits of the ICD between the ICD high-voltage electronic circuit and the filter two-terminal MLCC chip capacitor 288. Importantly, this parasitic inductance appears in series between the high-voltage source (ICD high energy storage capacitor) and the filter capacitor. When one solves the second order differential loop equation for this R-L-C circuit and incorporates the R-L-C circuit's initial conditions with the initially uncharged filter capacitor, the result is an exponentially decaying sinusoidal voltage that appears across said filter capacitor such as the two-terminal MLCC chip capacitor 288. There are two initial conditions necessary to solve the second order differential equation. The first initial condition follows the design principle that the voltage across the two-terminal MLCC chip capacitor 288 cannot be changed instantly wherein Vc(0−)=Vc(0+)=0 volts. The second initial condition is that one cannot instantly change the current through the parasitic inductance (L), wherein $I_L(0-)=I_L(0+)=0$. Solving the second order differential equation results in a voltage across the filter two-terminal MLCC chip capacitor 288 that overshoots, or, in a term of art, "rings up" and then sinusoidally exponentially decays.

Figure 10:
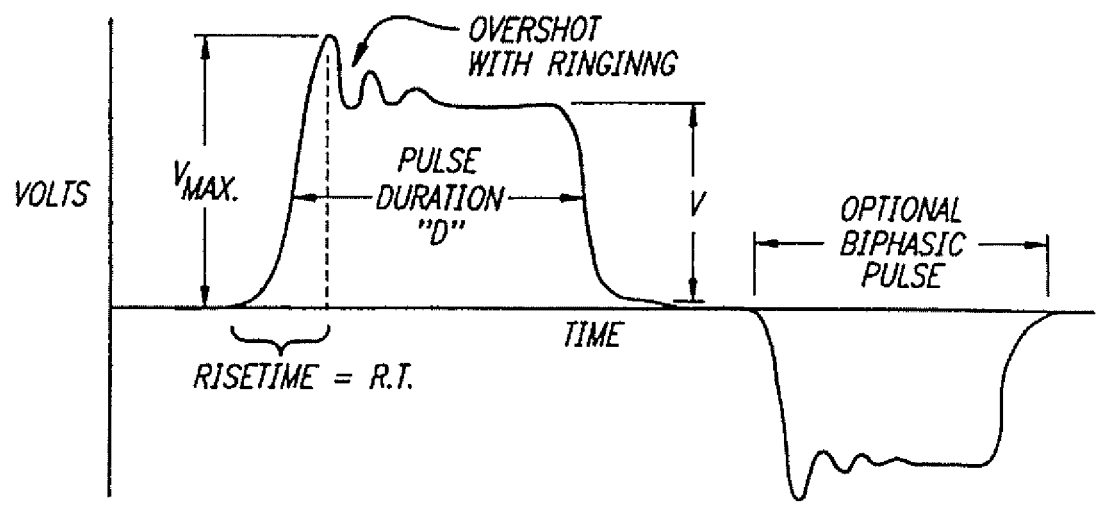
FIG. 10 is a calculated/computed graph of the voltage vs. time of a biphasic ICD shock pulse including overshoot and ringing characterizing the load across an initially uncharged EMI filter capacitor.

FIG. 10 illustrates the ICD high-voltage pulse across the filter two-terminal MLCC chip capacitor 288 with overshoot and ringing. This occurs right after the initial rise time of the HV pulse and causes the voltage to increase significantly as measured right at the filter two-terminal MLCC chip capacitor 288. Also shown is an optional biphasic pulse, which is of negative polarity. It has been found that these biphasic pulses are more efficient than just a monophasic shock in cardioverting an arrhythmic heart. Referring once again to FIG. 10, of great interest is the VMAX and the risetime R.T. from the point of view of the filter two-terminal MLCC chip capacitor 288 inrush current $i_c$.

Figures 11, 12:
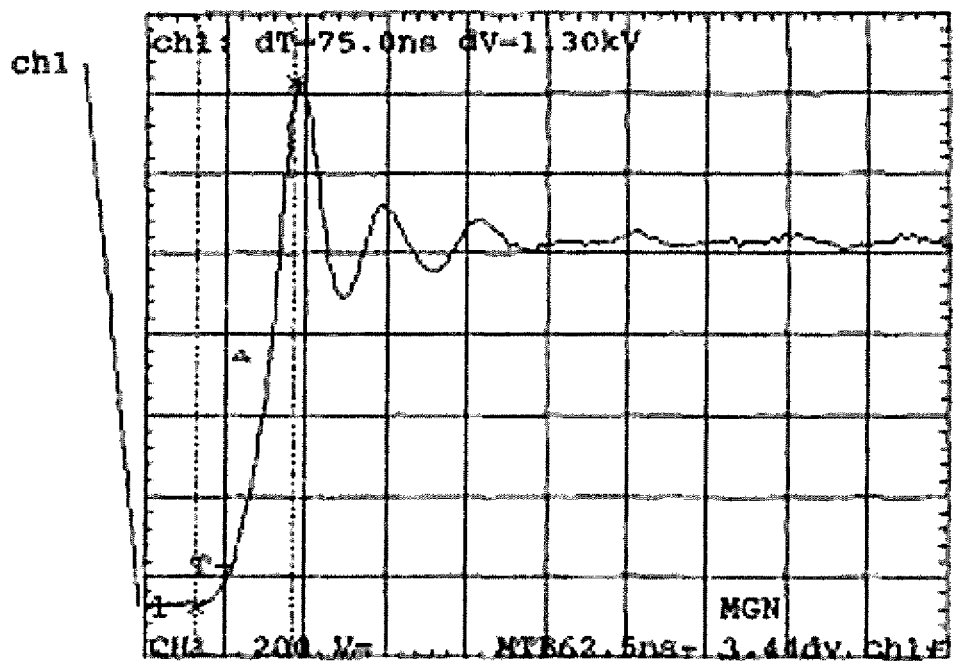
FIG. 11 is an oscilloscope screen capture of the voltage waveform of the leading edge of an ICD pulse measured across an initially uncharged EMI filter capacitor.
FIG. 12 is the differential equation for computing the EMI filter capacitor peak inrush current $i_c$ based on the delta voltage (dV or dv) and the rise time (dT or dt)) measured from the leading edge of the ICD pulse waveform of FIG. 11.

FIG. 11 is a screen shot taken with a special high-voltage fast risetime oscilloscope probe that shows the voltage measured directly across the filter two-terminal MLCC chip capacitor 288. FIG. 11 shows that the initial risetime of the HV pulse, that is delta time dT (or dt), is 75 nanoseconds with a delta voltage dV of 1.3 kilovolts.

FIG. 12 gives the differential equation for the inrush current $i_c$ that blasts into the filter two-terminal MLCC chip capacitor 288. Using the equation of FIG. 12, this means that a 1500 picofarad filter capacitor (which is nominal) is subject to an initial inrush current $i_c$ of 26 amps. Referring once again to FIG. 8, in particular to high-voltage active terminal pin 182h, this inrush current $i_c$ of 26 amps must also pass through the RF switch 380 in the normally closed (N.C.) position, which is also known as the normal operating position of the switch 380. Importantly, the RF switch 380 must be capable of conducting this initial inrush current $i_c$ of 26 amps without the RF switch itself becoming damaged. The inventors have done years of design work and experienced a significant learning curve on how to design filter capacitors, such as the two-terminal MLCC chip capacitor 288, to handle the inrush current $I_c$, particularly during the leading edge of an ICD therapy pulse. The design principles herein are equally applicable to feedthrough filter capacitors 270, 284 or X2Y attenuators 800, or flat-thru capacitors 600. For example, to properly handle inrush current $i_c$, filter capacitors can use a dual electrode plate design as disclosed in U.S. Pat. No. 5,978,204, the contents of which are fully incorporated herein by this reference. Dual electrode plates are an important design principle for making sure that the filter capacitors 288, 270, 284, 600, 800 can withstand an ICD charging current and voltage. In addition, electrode rheology, electrode conductivity and electrode melting point are also very important design principles so that the filter capacitors 288, 270, 284, 600, 800 can handle the ICD pulse inrush current without the filter capacitors themselves failing.

Referring once again to FIG. 8, it is noted that the two-terminal MLCC chip capacitors 288 associated with low-voltage active terminal pins 182a through 182g are accordingly a low-voltage filter capacitor design. Additionally, the two-terminal MLCC chip capacitor 288 associated with the high-voltage active terminal pins 182h are a much higher voltage pulse rating and preferably comprise dual electrode plate design. Accordingly, the high-voltage two-terminal MLCC chip capacitor is typically physically larger than the other two-terminal low-voltage MLCC chip capacitors (for simplicity, the MLCCs herein are illustrated having about the same relative size). Further regarding the filter capacitor of FIG. 8, the two-terminal MLCC chip capacitor 288 associated with the high-voltage active terminal pin 182h, is a reverse geometry two-terminal MLCC chip capacitor (see FIG. 4C), meaning that the electrical terminations are along the long sides of said reverse geometry two-terminal MLCC chip capacitor (FIG. 4C). Disposing the electrical terminations along the long sides of the filter capacitor is important to reduce the internal inductance of said filter capacitor. In an embodiment, all of the two-terminal MLCC chip capacitors shown in FIG. 8 are replaced by reverse geometry two-terminal MLCC chip capacitors (except for filter capacitor 288, which is already a reverse geometry filter capacitor), thereby reducing internal inductance thus providing superior high frequency filtering performance. Reverse geometry MLCC chip capacitors (FIG. 4C) are disclosed in FIG. 24 of U.S. Pat. No. 8,195,295 previously incorporated herein. As previously disclosed, a downside of reverse geometry MLCC chip capacitors (FIG. 4C) is a greatly reduced high-voltage flashover between opposite polarity terminations 274 and 275a. Referring once again to FIG. 8, for the high-voltage circuit comprising the high-voltage active terminal pin 182h (as noted, additional high-voltage poles can be added), a conformal coating or an epoxy could be placed over the RF switch and the filter two-terminal MLCC chip capacitor 288 to prevent high-voltage arcs or flashovers across the surface of the chip component or between the terminal pins. For simplicity, such a conformal coating or epoxy is not shown. Consideration of the magnitude of the ICD inrush current $i_c$ into the two-terminal MLCC chip capacitor 288 is required to properly identify and select an RF switch. Furthermore, the selection of any RF switch needs to consider all of the following: current handling capability, DC resistance, inductance and pulse handling capability. Of particular advantage to high-voltage applications is a design principle regarding a slow responding RF switch. Specifically, when an RF switch is slow to respond (greater than 1 millisecond) to a fast risetime pulse, such as during an ICD pulse, then the rate of MLCC capacitor charging should also be slow so that the amount of peak current that the RF switch has to handle is reduced.

As defined herein, "complete or full capacitor disconnection" is an embodiment wherein all (or both) of the high-voltage filter capacitors (typically RV and SVC) are disconnected during ICD pulse delivery by the RF switch(es) from both system ground 210.103 and also from any common ground plane, common ground electrode 273 or common circuit board ground plate 396 (this eliminates any pin to pin series capacitance). Complete or full disconnection enables use of common low-voltage capacitors that do not need to be pulse-rated at all.

As defined herein, "partial filter capacitor disconnection" is an embodiment wherein the high-voltage filter capacitors (typically RV and SVC) are disconnected during ICD pulse delivery from only the system ground 210, 103 but are still electrically connected to a common ground electrode 273, a common ground plane or a circuit board ground plate 396. A partial filter capacitor disconnection results in an RV to SVC pin series capacitance. This series capacitance between the exemplary RV and SVC pins means that the capacitances become a voltage divider. In addition, for capacitors in series, the total capacitance is halved. When an ICD HV shock is reference between the RV and SVC electrodes, this means that each capacitor receives one-half the ICD shock ring up voltage and the capacitor inrush current $i_c$ is halved. As a result, filter capacitor selection is simplified, however, the selected filter capacitors still need to be HV rated (½ the voltage) and also pulse-rated (½ the inrush current, $i_c$).

As previously disclosed, it is an advantage to completely disconnect from ground and also isolate (from each other) the high-voltage SVC and RV filter capacitors during delivery of an ICD pulse. This is because there is no filter capacitor inrush current $i_c$ and the filter capacitor(s) is not exposed to the high-voltage ICD pulse. In other words, if the high-voltage filter capacitors are completely disconnected by a high-voltage RF switch during delivery of an ICD pulse, then there is no concern of an inrush current (as defined by the equation of FIG. 12) into the filter capacitor. When the high-voltage filter capacitors are completely disconnected, since there is no inrush current, this allows the filter capacitor(s) to be commercial off the shelf (COTS) low-voltage filter capacitors (288, 270, 284, 600, 800). Elimination of high-voltage pulse and inrush current rated filter capacitors is very important as such pulse rated capacitors are custom, expensive and much larger physically. This also means that, with the RF switch(es) disconnected (OPEN) from the filter capacitor(s), the RF switch itself also does not have to conduct any capacitor inrush current $i_c$, which greatly simplifies RF switch selection (it does need to be capable of high voltage to stand off the ICD pulse). But elimination of the filter capacitor inrush current does allow the RF switches to be smaller and less expensive.

Another factor relevant to proper selection of an RF switch for an AIMD (such as an ICD) is that when the RF switch is in its N.C. or normal operating position, the RF switch must be rated to bypass or divert a significant amount of high frequency MRI-pulsed RF energy while the patient is undergoing an MRI scan. In an MR scanner, a patient having an AIMD implant is subjected to a powerful RF-pulsed field. For example, a 1.5 Tesla MRI scanner uses a 64 MHz RF-pulsed field and a 3 Tesla MRI scanner uses a 128 MHz RF-pulsed field. This intense RF-pulsed field is generated by what is termed a birdcage coil, which is circular in shape. The MRI RF-pulsed energy is picked up by implanted leads through antenna action where it can be conducted to sensitive circuits inside the device side of the AIMD. Desirably, the EMI feedthrough capacitor filters 270, 284, the two-terminal MLCC chip capacitors 288, the flat-thru capacitors 614 and the X2Y attenuators 800 of the present invention are all designed to divert (attenuate) such dangerous MRI RF energy from the active implanted leads to the ferrule 210 of the hermetic feedthrough and, in turn, to the AIMD housing 103 which acts as an enclosed shield, where the dangerous MRI RF energy is harmlessly dissipated as a few milliwatts (and even peak watts) of harmless heat energy, which is how the filter capacitors of the present inventions work (they divert dangerous EMI RF energy from the active circuits at or near the point of implanted leadwire entry into the AIMD housing 103 while, at the same time, they allow low frequency therapeutic pulses, biologic sense signals, and even ICD HV pulses to freely pass with little to no attenuation. The filter capacitors of the present inventions divert unwanted EMI signals to the AIMD housing, which acts as an overall Faraday shield or cage.

Figure 13:
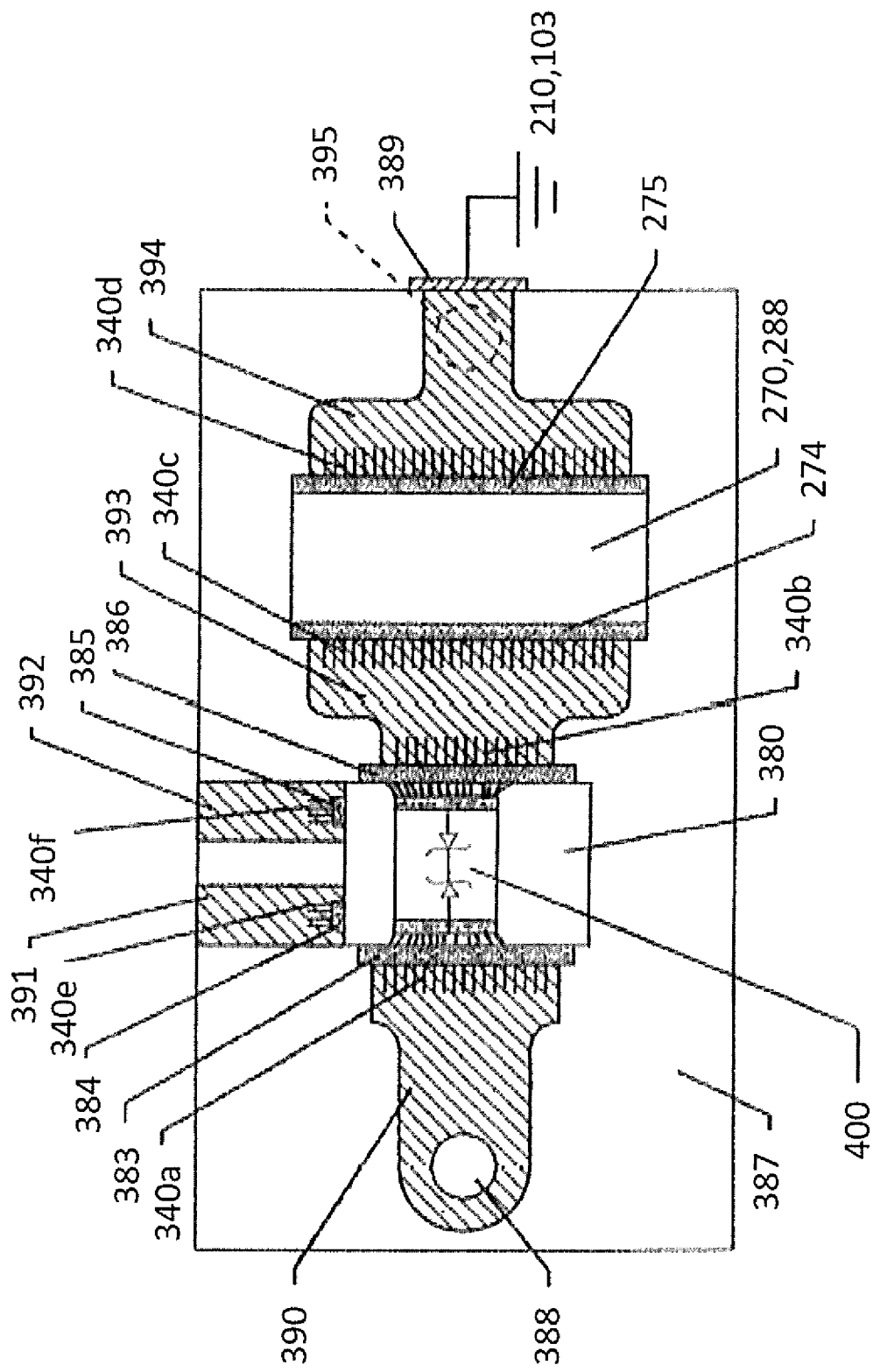
FIG. 13 illustrates a back-to-back diode transient voltage suppressor (TVS), also known as surge voltage protector or a current suppression device, installed electrically in parallel with the normally closed (N.C.) position of the RF switch for the purpose of bypassing the RF switch of at least a portion of the EMI filter capacitor peak inrush current $i_c$ during a monophasic or a biphasic ICD pulse.

FIG. 13 is similar to FIG. 4B, except that instead of just an RF switch 380, a back-to-back transient voltage suppressor 400 is shown stacked atop the RF switch 380 and is electrically wired in parallel with said RF switch 380. Transient voltage suppressor (TVS) devices are also often known as electrostatic discharge (ESD) devices (or in some cases, pulse current bypass devices). The TVS (or clamping) can include Zener diodes, Schottky diodes, and metal-oxide varistors (MOV). TVS devices can respond very quickly to over-voltages. During an ICD pulse, a voltage develops across the RF switch 380 due to its internal inductance and resistance. A properly selected TVS clamps at about 5 volts, thereby diverting around the RF switch a significant amount of the ICD inrush current $i_c$ charging the filter capacitor 270, 288. This clamping current is bypassed in parallel around the RF switch through the TVS or ESD device. This allows the use of an RF switch that has a lower current rating and pulse handling capability (and, as previously disclosed, a relatively slow switching speed). Importantly, the use of such RF switches having lower current ratings, pulse handling capabilities and relatively slow switching speeds enable the use of a physically smaller and less expensive RF switch 380 then say an electro-mechanical switch. Hence, RF switches having lower current ratings, pulse handling capabilities and relatively slow switching speeds can accordingly be useful and effective solution for particularly small footprint applications or for inclusion in tightly-toleranced spaces.

Figure 14:
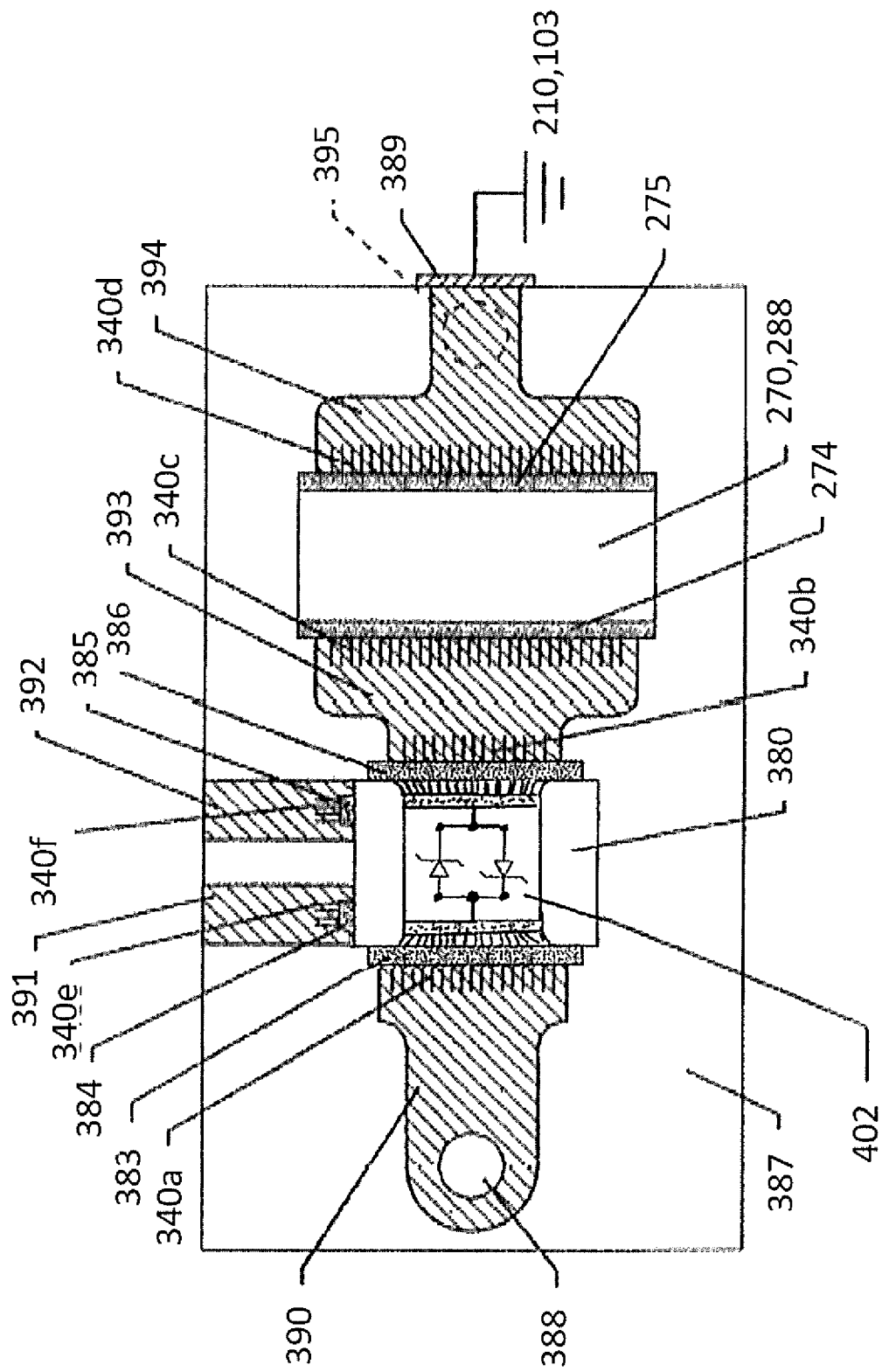
FIG. 14 illustrates two diodes of reverse polarity installed electrically in parallel with the N.C. position of the RF switch for the purpose of bypassing the RF switch of at least a portion of the capacitor peak inrush current $i_c$ during a monophasic or biphasic ICD pulse.
Figure 30:
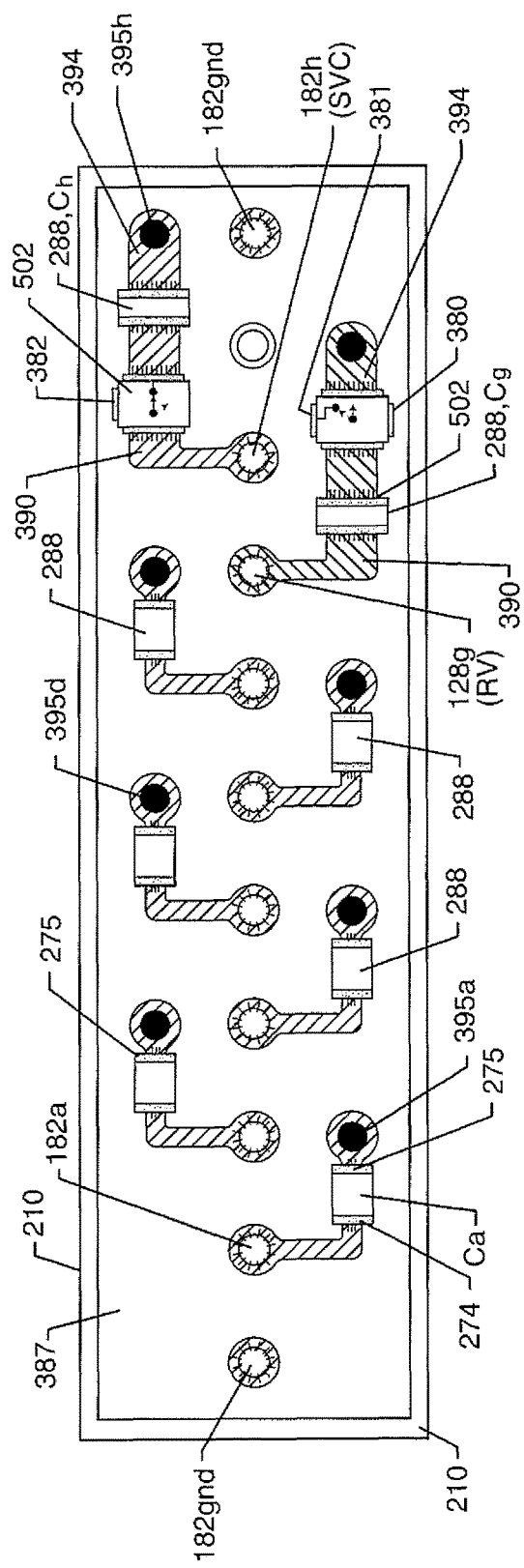
FIG. 30 is the top view of an MLCC filter capacitor circuit board disposed on the device side of the hermetic feedthrough. Illustrated are two RF switches, either SPST, SPDT, or combinations thereof, which completely disconnect the right ventricle (RV) and SVC HV shocking filter MLCC chip capacitors from system ground and also disconnects the series common ground circuit between the two MLCC chip capacitors.

FIG. 14 illustrates an alternative TVS device embodiment comprising a parallel reverse polarity diode arrangement 402. The parallel reverse polarity diode arrangement 402 may comprise Zener diodes (curved schematic lines as shown) or other types of diodes (straight schematic lines, not shown). The TVS devices of FIG. 13 (400) and FIG. 14 (402) are selected from the groups consisting of TVS-diodes, metal-oxide varistors (MOVs), avalanche diodes, Zener diodes and gas-discharged tubes. In summary, the purpose of transient voltage suppressors (or diodes) of FIGS. 13 and 14, are primarily for embodiments herein where the RF switch does not completely disconnect the filter capacitor (in other words, for embodiments such as shown in FIGS. 22, 25, 27, 36, 37 and 40 where the filter capacitor is only partially disconnected when the RF switch is opened and there is still a series common ground to adjacent filter capacitors). Using a TVS to bypass a significant amount of the ICD peak pulse current (such as the exemplary 26 amp peak current previously disclosed) so that all the peak current amperage does not flow through the RF switch 380 is especially important in the case that the RF switches are not opened up (these are the embodiments where the switch was only designed to disconnect the filter capacitors during RF signal 381 injection). In certain embodiments herein, such as shown in FIGS. 6 and 30, when the RF switch is programmed to be open throughout an ICD pulse, then the need for a TVS device 400,402 in parallel with the switch is minimized (it can still be used to protect the RF switch 380,502, but it would not have to handle any filter capacitor inrush current at all. This TVS device embodiment allows alternative cost effective RF switch 380 (or 502) selection options, such as, smaller and less expensive package sizes. It is noted that TVS devices, particularly those sold in tape and reel packages, are suitable for robotic dispensing, widely available in very small package sizes and very inexpensive.

Referring once again to TVS device embodiments 400 and 402 of FIGS. 13 and 14 respectively, modern TVS devices are now manufactured as a single element, hence the TVS devices do not even need to have discrete diode elements as illustrated. It is important for ICD biphasic pulses that TVS devices be able to suppress pulses of both positive and negative polarity. Referring once again to the diode packages (TVS devices) 400 and 402, such TVS packages comprise a metallization (not labelled) on each of the opposite ends of the TVS device. A conductive connection material (not labelled) electrically connects the TVS package in parallel with the N.C. or normally operating position of the RF switch 380 (or 502).

Figure 15:
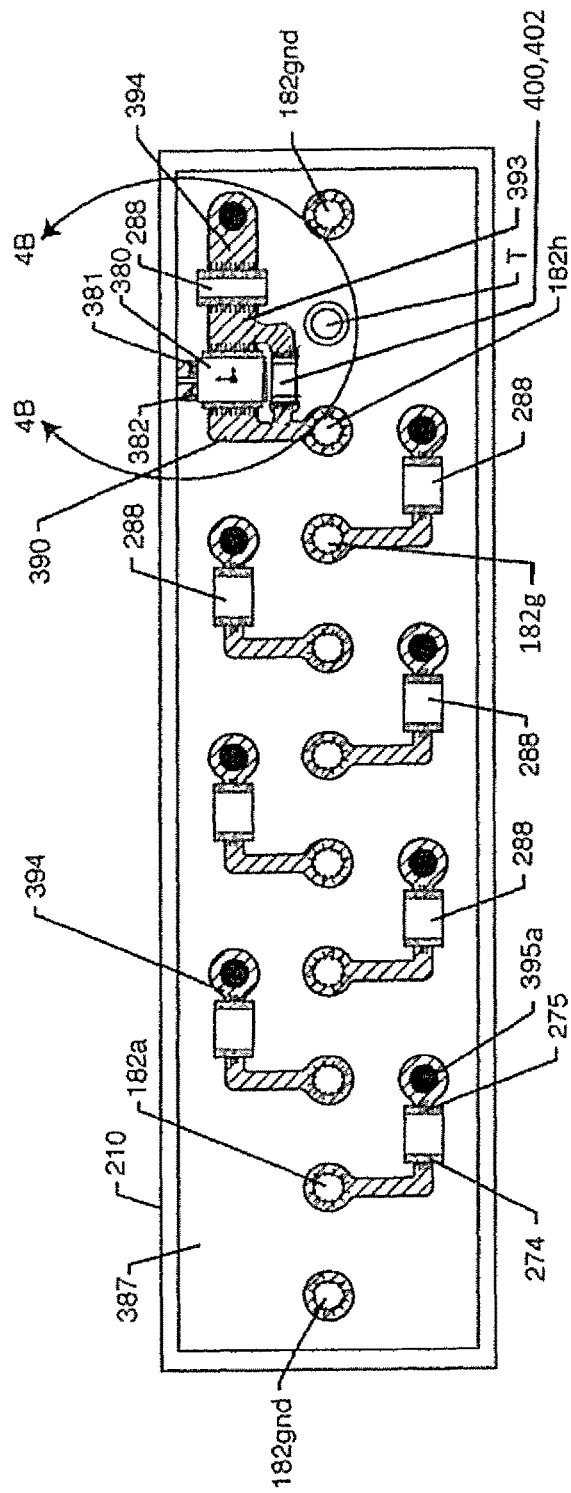
FIG. 15 illustrates a modification of the circuit board trace of FIG. 8 that provides a surface mounting location for the TVS device of either FIG. 13 or 14 such that the TVS device is electrically connected in parallel with the N.C. position of the RF switch.

FIG. 15 is very similar to FIG. 8, except that in the high-voltage circuit comprising the high-voltage active terminal pin 182h a parallel circuit board trace/pathway has been added.

The TVS device 400 of FIG. 13 or the back to back TVS diode package of FIG. 14 is attached to circuit trace lands of the circuit board disposed in parallel with the RF switch 380. As shown, the circuit traces 390 and 393 of FIG. 8 are modified to provide the parallel circuit mounting of the TVS device. It is noted that the embodiment of FIG. 15 is an alternative to having the TVS devices 400 or 402 stacked atop the RF switch 380 as shown in FIGS. 13 and 14. When selecting a diode TVS device 400, 402, it is important to apply the design principles previously disclosed, meaning that the breakdown voltage, the clamping time, the clamping voltage, the parasitic capacitance and the inductance must be analyzed so that the filter capacitors 288, 270, 28, 614, 800 can handle the ICD pulse inrush current $i_c$ without the RF switch 380,502 or the filter capacitors themselves failing. Importantly, the amount of energy that the TVS device 400,402 can absorb must also be analyzed. Because the ICD transients are so brief, the energy in the TVS device is initially stored as heat. The heat sink (which comprises the TVS package case and the adjacent structures) offers significant time for TVS device 400,402 to cool down after the pulse rise time has occurred and, if the arrhythmia is still present, subsequent and even higher energy ICD pulses if needed to cardiovert the patient. Fortunately, ICD shocks do not occur in a rapid pulse chain one right after the other. ICD pulses are separated by at least a few seconds (it takes several seconds to as much as ten seconds for the ICD internal battery to re-charge the ICD's internal high energy storage capacitor). Accordingly, since the TVS device only has to handle one large shock at a time, selection of the TVS device 400,402 is less challenging. When an ICD delivers a high-voltage shock to cardiovert an arrhythmic heart of a patient (that is, after the therapy pulse is delivered), the ICD re-interrogates the heart by "listening" to (monitoring) biological signals. During this time, the high-voltage energy capacitor of the ICD slowly charges so, if needed, another cardioverting shock can be delivered to the patient. This can, however, take several seconds, which gives the diode TVS device 400,402 sufficient time to cool back down.

As previously disclosed, if the AIMD is programmed to toggle (switch) the RF switch to completely disconnect the RV and SVC filter capacitors during delivery of an ICD pulse, then neither the RF switch nor the TVS device have to be pulse-rated. In most cases, the TVS device is not needed when the capacitors are disconnected both from system ground 210, 130 and from each other (i.e., are also disconnected from any common ground plane which would create series capacitance between adjacent filters 288, 270, 284, 614, 800). The RF switch 380 or 502 does, however, need to be high-voltage rated to stand off the ICD pulse. In an embodiment, by disconnecting the high-voltage filter capacitors, one does not even need the TVS devices since there would be an open circuit and therefore no capacitor inrush current $i_c$ to bypass (ref. FIG. 12).

Figure 16:
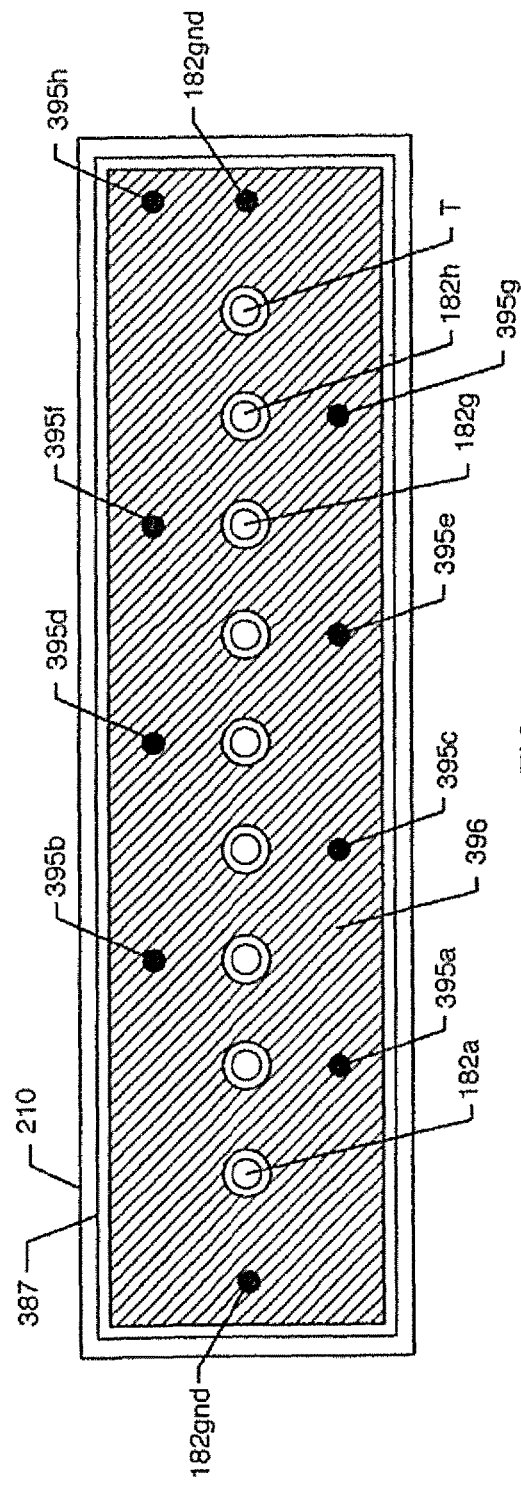
FIG. 16 is the same as FIG. 8A illustrating the ground shield plate of the circuit board.

FIG. 16 is similar to FIG. 8A, illustrating an internal ground plate 396 of the circuit board 387 of FIG. 16. It is understood that at least one ground plate 396 is disposed within (internal ground plate) or on (external ground plate) the circuit board 387. The ground plate 396 is important in that it acts as an RF shield thereby reflecting and absorbing incident radiated RF EMI energy while preventing direct penetration of radiated EMI through the insulator 240 of the hermetic feedthrough from the body fluid side to the device side (inside the AIMD housing). Such circuit board shield ground plate(s) 396 are more thoroughly disclosed in U.S. Pat. Nos. 8,095,224; 8,195,295; 8,321,032; 8,437,865; 8,433,410; 8,483,840; 8,670,841; 8,712,544; 8,716,895; 8,868,189; 8,918,189; 8,996,126; 9,031,670; 9,071,221; 9,463,329; 9,895,534; 10,016,595; 10,016,596; 10,080,889; 10,099,051; and 10,124,164; U.S. patent application Ser. Nos. 16/364,953; 16/385,338; 16/435,600; and 16/452,785; the contents of which are fully incorporated herein by these references.

Figure 17:
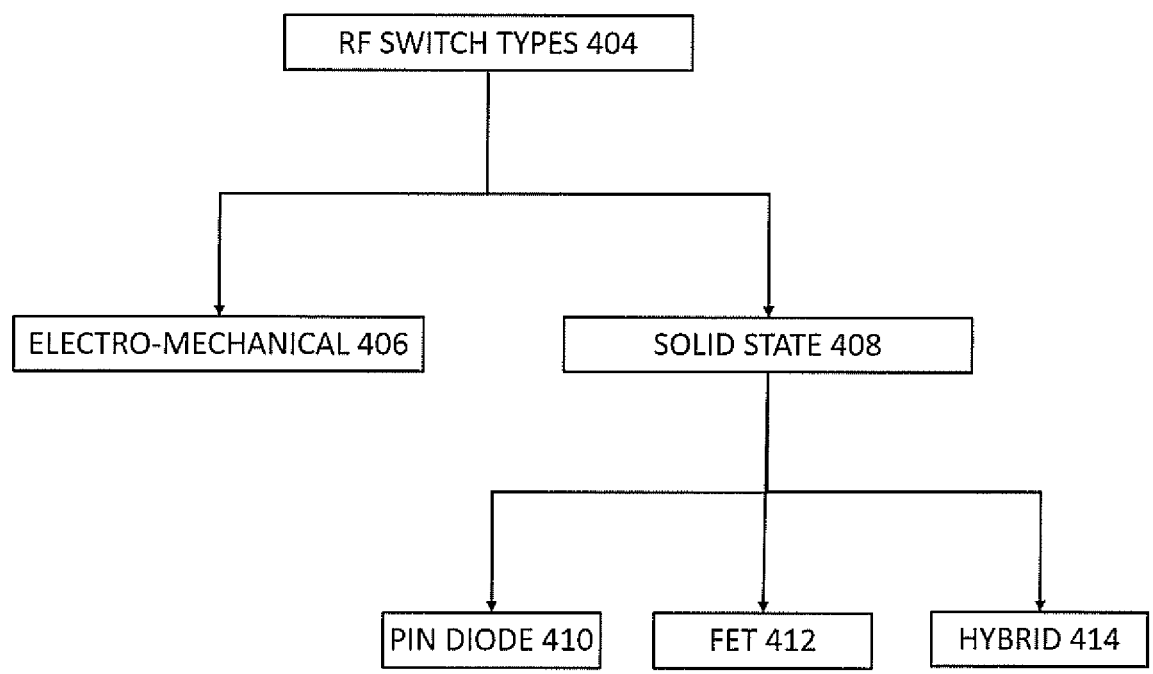
FIG. 17 is a block diagram showing various types of RF switches suitable for use in the present invention.

FIG. 17 is a block diagram showing various types of RF switches 380,502 that can be used in the present invention. The first level of the chart indicates RF Switch Types 404. As illustrated, there are two main types of RF switches: electro-mechanical switches 406 and solid-state switches 408. Solid-state switches 408 can comprise pin diodes 410; field effect transistor switches (FETs) 412; or hybrid solid-state switches 414. Other types of solid-state switches (not shown) include silicon diodes and gallium arsenide field-effect transistor (GaAs FET) among others. it is noted that FETs include the entire family of metal-oxide semiconductor field effect transistors (MOSFETs). In general, electro-mechanical RF switches 406 tend to have very poor ohmic loss at DC and at low frequency biologic signals; however, this is not important. What is important is that the RF switch pass high-frequency signals from 10 MHz and above with very little attenuation so that the filter capacitors 270, 284, 288, 600, 800 can work effectively as EMI filters. Solid state RF switches 408 generally provide superior performance with high isolation and fast switching speed across a broad operating frequency range and usually operate in the MHz range; however, some solid-state RF switches operate in the kHz range. Solid state RF switches have no moving parts and typically rely on semiconductors to control current flow. Solid state RF switches operating in the MHz range include, for example, Pin diodes and solid state RF switches operating in the kHz range include, for example, hybrid-combined Pin diodes and FETs. In the present invention, it is not important that the RF switch have very low loss at DC or low frequency biological frequencies, as it is not desirable to filter these low frequencies anyway. Furthermore, the characteristics of the two-terminal MLCC chip capacitor desirably present a very high impedance (capacitive reactance) at such low frequencies. Thus, solid-state RF switches 408 are ideal for use in the present invention, as it is really only important that the RF switch have low loss starting at 10 MHz up through frequencies, for example, of 1 GHz to 3 GHz. At these high frequencies, where, for example, certain cellular telephones operate, diverting (filtering) these high frequency EMI signals is very important because, as previously disclosed, such EMI signals can be dangerous if they cause AIMDs to malfunction (in particular, prolonged EMI malfunction that would result in a Hayes Class I or II response). In the present invention, the switching speed of the RF switch is relatively unimportant. In the electrical engineering world of microseconds, there is plenty of time (milliseconds or even seconds) to switch the RF switch 380,502 from its normal operating (N.C.) mode to either an RF signal 381 interrogation mode or to one of the ICD pulse (complete or partial filter capacitor disconnection) modes. Solid-state RF switches can be absorptive RF switches or reflective RF switches or combinations of the two. A primary consideration is the voltage standing wave issue VSWR. In general, absorptive RF switches have good (low) VSWR whereas, reflective RF switches have poor (relatively high) VSWR. Absorptive RF switches can be used in the present application as it is not important that the switching POLES offer an exact 50-ohm impedance.

Accordingly, the design principles are important in the selection of the RF switch 380 because the RF switch must handle the inrush current $i_c$ of the ICD pulse, of which there are various RF switch types 404 (unless, a different embodiment is used, wherein the filter capacitor has been completely disconnected by the RF switch during delivery of the ICD pulse such that there is no inrush current $i_c$, greatly simplifying switch selection). Additionally, either a TVS device 400,402 or an equivalent pulse current bypass device may be connected in parallel with the RF switch 380 such that the entire capacitor inrush current $i_c$ (for example, the 26 amp peak current) does not entirely pass through the RF switch 380. It is desirable that at least one-half of the peak inrush current be diverted (bypassed) through the parallel TVS device around the switch 380 such that the switch 380 not be overloaded.

Figure 18:
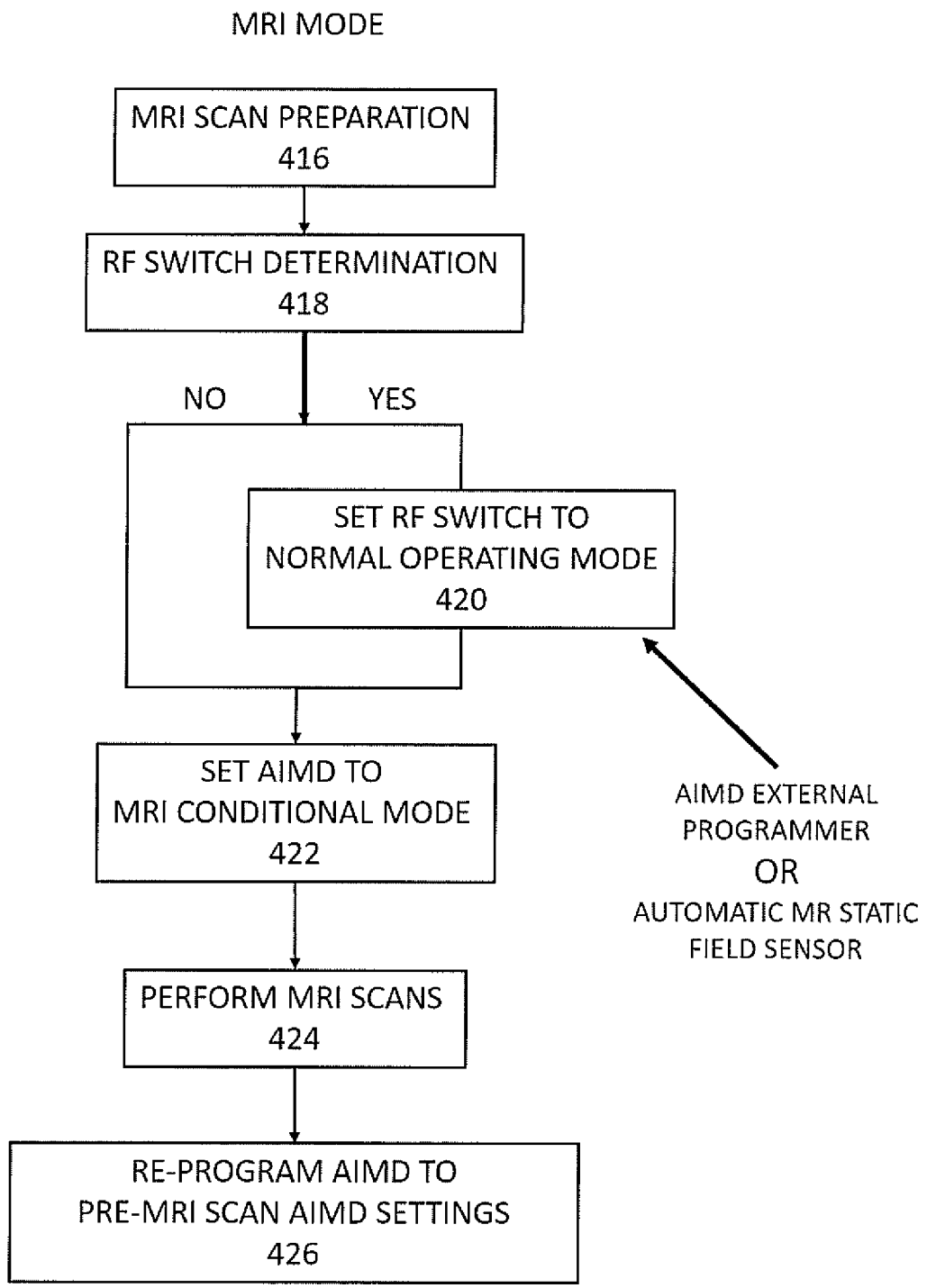
FIG. 18 is a process flowchart of an MRI operating mode. The RF switch of the present invention is in a normal operating mode (N.C. position) throughout the MRI scanning of an AIMD patient.

Referring once again to FIG. 3A and the process flowchart of FIG. 18, another novel aspect of the present invention is to have the ICD electronic control circuitry provide the AIMD control signal 382 to switch the RF switch 380 from THROW 1 (also called the N.C. or normal operating mode) to the THROW 2 (the RF test position or OFF position during ICD pulse delivery) immediately prior to and during the application of an ICD 1008 pulse or repeat pulses. This disconnects the filter capacitor 270, 284, 288, 600, 800 during the entire ICD pulse and thereby eliminates concerns about rating the MLCC and the RF switch 380 to handle the filter capacitor ICD pulse inrush current $i_c$. A monophasic or biphasic ICD pulse width is only on the order of 20 to a maximum of 100 milliseconds. Disconnection of the filter capacitor 270, 284, 288, 600, 800 means that for the brief period of time during the ICD pulse, EMI filtering will not be present on the high voltage shock lead (SVC or RV for example). Importantly, loss of EMI filtering for the brief time of an ICD pulse delivery is not important. This is because, for EMI to become dangerous, it must generally involve prolonged exposure of the AIMD and its leads for generally longer than two to three seconds. One is referred to a paper in the New England Journal of Medicine, entitled INTERFERENCE WITH CARDIAC PACEMAKERS BY CELLULAR TELEPHONES, VOL. 336, May 22, 1997 #21. This paper has, somewhat famously, become known as "The Hayes Criteria". The Hayes Criteria establishes the clinically significant interference with pacemaker functions, which also extend to ICD functions. Clinically relevant classes of interference response are Class 1 and Class 2, generally take exposure to the electromagnetic interference for a period of time greater than 3 seconds. (Ref. Hayes Table 1.)

Figure 19:
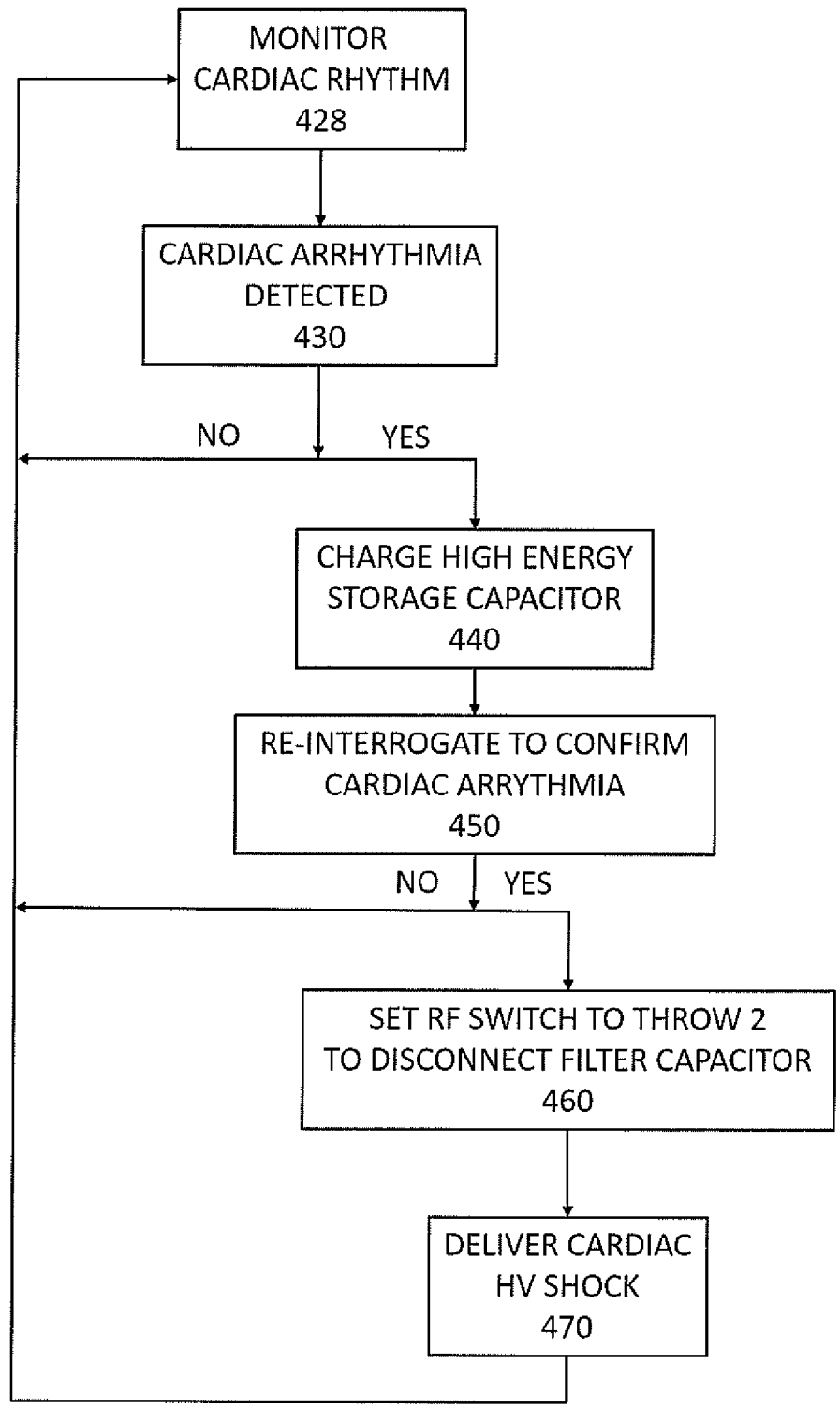
FIG. 19 is a process flowchart for disconnecting a filter capacitor during delivery of ICD high-voltage shock therapy. Dis-connection of a filter capacitor enables use of lower voltage-rated filter capacitors.

Hayes Table 1 as illustrated in FIG. 19 has been cited extensively by the International Cardiovascular Implantable Electronic Device (CIED) Committee, which is responsible for writing and revising the International Standard ISO 14117. The title of ISO 14117 is ACTIVE IMPLANTABLE MEDICAL DEVICES—ELECTROMAGNETIC COMPATIBILITY—EMC TEST PROTOCOLS FOR IMPLANTABLE CARDIAC PACEMAKERS, IMPLANTABLE CARDIO DEFIBRILLATORS AND CARDIAC RESYNCHRONIZATION DEVICES. The Hayes paper and ISO 14117 are incorporated fully herein by these references. ISO 14117 relies on The Hayes Criteria to determine whether electromagnetic interference is a pass or fail (in other words, is prolonged enough to be of clinical significance). In summary, this dis-connection of only the filter capacitor 270, 284, 288, 600, 800 by the RF switch 380,502 during an ICD pulse disconnects the filter capacitor for less than 100 milliseconds (at most ½ second or 500 milliseconds). Interference duration of 500 milliseconds maximum meets the Hayes clinically insignificant Class III criteria. Hayes class I and class II are deemed clinically significant but require prolonged pacemaker AIMD circuit interference/disruption for longer than 2 to 3 seconds. An ICD inappropriate discharge also is deemed clinically significant, but this also takes prolonged EMI exposure of a least 3 seconds which also is far shorter than the RF switch disconnects the filter capacitor (500 milliseconds maximum) for RF signal 381 testing.

For example, cardiac pacemaker implantable cardioverter defibrillator (ICD) patients are advised to "don't lean and don't linger" when exiting a retail store that has electronic articles surveillance (EAS) security gates. As long as the patient walks slowly out of the store through these EAS gates, their pacemaker only drops a few beats (a time period less than the Hayes Class I and II clinically significant criteria 3-second limit). In addition, their ICD does not have time to charge up and deliver an inappropriate high-voltage shock (this takes 5 to 10 seconds). In other words, as long as the patient doesn't lean and doesn't linger, interference does occur, but the interferences is not of clinical significance per the Hayes Class I and II criteria. Unfortunately, these EAS gates are often camouflaged by retail advertising or goods displays and there have been a number of documented cases where a patient has lingered in the presence of these EAS gates, and either pacemaker inhibition or an inappropriate high-voltage shock was delivered.

Referring once again to FIG. 3A in view of the process flowchart of FIG. 18, disconnecting the filter capacitor during an ICD pulse would desirably NOT be used concurrently with an RF interrogation signal 381 or independently of (without) an RF interrogation signal 381, because the ICD high-voltage pulse could burn out (overload) the relatively sensitive RF signal generator and reflection return analysis receiver. This can be accomplished by adding a third THROW (not shown) to the RF switch 380 of FIG. 3A. The third THROW would be an open position (not connected). This third THROW position would be used during delivery of an HV ICD shock pulse so that the low-voltage RF interrogation signal electronic circuits 381 are isolated from the high voltage. In summary, disconnecting the filter capacitor 270, 284, 288, 600, 800 immediately prior to and during the ICD pulse allows one to select a much smaller and less expensive filter capacitor. This is because the inrush current $i_c$ no longer flows to the capacitor during the initial rise-time and ring up of the ICD pulse. During the ICD pulse, it is also necessary to isolate the RF signal 381 circuits (this can be done by a SINGLE or DOUBLE POLE 3-THROW RF switch 380 (not shown) or, more easily, as a function of the AIMD electronics, such as an ASIC logic.

It will be appreciated that if the filter capacitor 270, 284, 288, 600, 800 is disconnected during an ICD pulse delivery, an RF interrogation signal 381 is used at the same time because the high-voltage pulse would tend to burn out the relatively sensitive RF pulse source in the AIMD electronic circuits (ASIC). Referring once again to Step 460 of FIG. 18, when the RF switch is set to THROW 2 to disconnect the filter capacitor before an ICD pulse, the AIMD electronics would also disconnect to make sure there is no attempt by the AIMD electronics to pass an RF interrogation signal on top of the ICD high-voltage shock pulse of Step 470. Dis-connection and isolation of the RF signal 381 circuits is important because the RF test signal 381 low-voltage circuits are not designed to handle such high voltages as produced by an ICD shock voltage.

Figure 21:
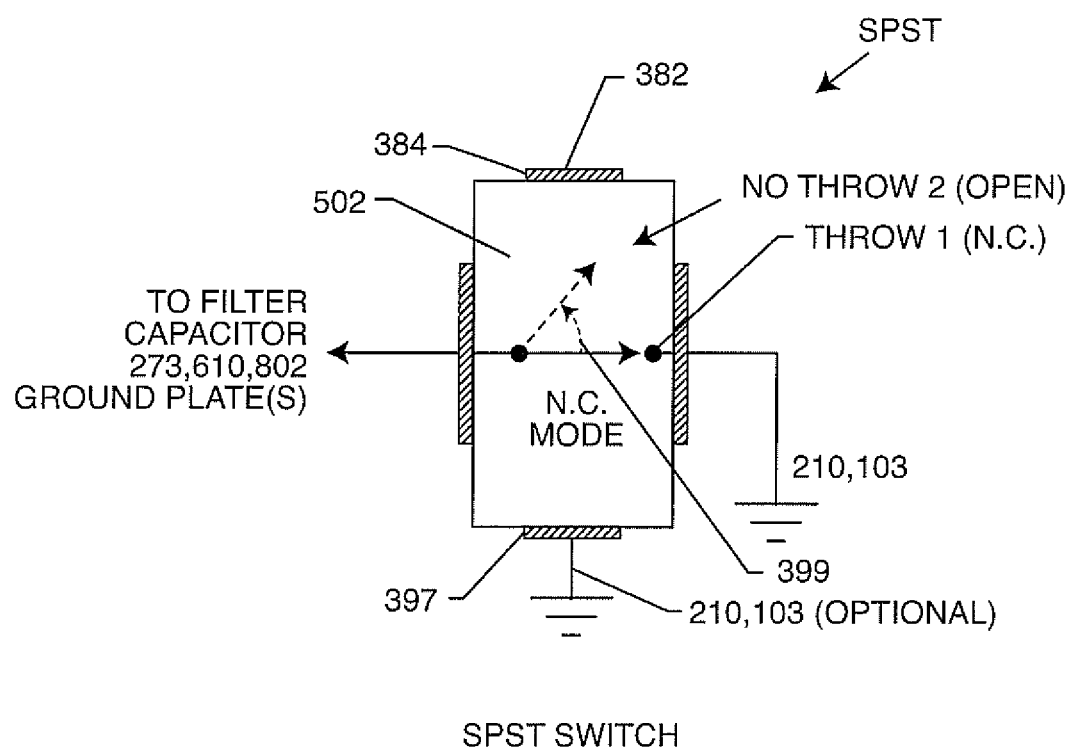
FIG. 21 shows an alternative SINGLE-POLE SINGLE-THROW RF switch in contrast to the SINGLE-POLE DOUBLE-THROW RF switch of FIG. 3A.

FIG. 20 provides a process flowchart for placing an AIMD in an MRI mode. It is essential that the RF switch 380 remains in its N.C. position (also known as the FIRST THROW or normal operating mode) when a patient is undergoing an MRI scan such that the EMI filter capacitor 270, 284, 288, 600, 800 is operational (will divert dangerous RF energy). It is known that the intense RF-pulsed fields of the MRI scanner can dangerously interfere with proper AIMD operation. Moreover, when a patient is having an MRI scan, the filter capacitor 270, 284, 288, 600, 800 is extremely important, as the filter capacitor diverts (filters) any dangerous and undesirable EMI energy that is picked up by implanted leads and redirects said dangerous and undesirable EMI energy to the AIMD ferrule and housing such that said EMI does not disrupt or damage sensitive electronics residing inside the housing of the AIMD, for example, the ASIC chips of the AIMD among others. Referring to FIGS. 3A and 21, it is highly undesirable for the AIMD internal electronics (such as the ASIC electronics) to send a routine control signal 382 to the RF switch 380 to switch from the normal operating mode (THROW 1) to an RF test mode or OPEN mode (THROW 2) when the patient is within an MRI scanner. Doing so would temporarily disconnect the EMI filter capacitor 270, 284, 288, 600, 800 from the AIMD circuit 182h, which causes the AIMD electronics to be unprotected. Disconnecting EMI filtering during a patient MRI scan for even less than 3 seconds in accordance with the Hayes criteria is dangerous. This is dangerous because, in the presence of such extremely high amplitude fields inside the MRI scanner bore, AIMD/ICD damage or what is known as power on resets (PORs) can occur, which has been documented by clinicians. Damage or PORs can happen instantly in an MRI environment (in far less time than the 3 seconds specified by the Hayes criteria). It has also been documented that the AIMD, which is programmed to a non-sensing mode prior to the MRI scan, may undesirably return (reset) to a sensing mode after a POR. Returning to a sensing mode in the MRI scanner could be very dangerous as the AIMD, such as a cardiac pacemaker, may then incorrectly sense the MRI RF noise (EMI) and interrupt such MRI RF noise as a normal heartbeat, which could then cause the exemplary cardiac pacemaker to inhibit. As an example, a POR was reported at Europace by Dr. J. Rod Gimbel in 2009 (Ref. Europace Volume 11 Number 9 September 2009 entitled: UNEXPECTED ASYSTOLE DURING 3T MAGNETIC RESONANCE IMAGING OF A PACEMAKER-DEPENDENT PATIENT WITH A 'MODERN PACEMAKER'. Asystole is immediately life-threatening for a pacemaker dependent patient. In this example, Dr. Gimbel was carefully monitoring the patient during an MRI scan in real time and immediately noticed that the patient's pulse-ox had dangerously dropped. Dr. Gimbel instantly terminated the MRI scan which caused the pacemaker to start delivering beating pulses again which save this patient's life. In summary, dis-connection of AIMD filtering (even for a brief moment of time) during an MRI scan is contraindicated. Accordingly, the MRI mode is an important feature of an AIMD that has an RF switch of the present invention, as the MRI mode keeps the RF switches 380 and 502 in their normal operating mode (THROW 1—N.C.), which keeps the EMI filters operational and enables patients with active implantable medical devices, such as an ICD, a pacemaker, a neurostimulator and the like, to safely undergo MRI. The first step of the MRI mode process is MRI scan preparation 416, which prepares the patient for the MRI. The next step is RF switch determination 418, which assesses whether or not an RF switch 380 of the present invention is present in the patient's implanted device. RF switch determination 418 can be established in various ways, such as through the Information for Use (IFU) paperwork each patient has regarding his/her implanted device, by X-Ray identification tag, through a patient ID card that provides device model numbers and serial numbers, or an RFID identification tag or the like. If Step 418 determines that the AIMD of the patient does not have an RF switch, then a "no" decision path is followed, wherein the AIMD may be set to an MRI conditional operating mode 422 as approved by the FDA. If Step 418 determines that the AIMD of the patient does have an RF switch, then a "yes" decision path is followed, wherein the RF switch of the AIMD is set (switched) to the normal operating mode (in other words, to keep the RF switch connected to the filter capacitor 270, 284, 288, 600, 800 throughout the MRI scan). It is contemplated that setting the RF switch to remain in the N.C. position could alternatively be included in Step 422 which integrates Step 420 and Step 422 together. An AIMD comprising an RF switch of the present invention is programmed to the MRI conditional operating modes, which includes programming for setting the RF switch to its N.C. position, otherwise called its "normal operating mode" for the full time that a patient is undergoing an MRI scan(s). This MR setting disables the control signal 382 until Step 426 when the AIMD is re-programmed to its pre-MRI scan settings. It is very common for modern pacemakers and cardioverter defibrillators, including cardiac resynchronization therapy (CRT) devices, to have an MRI conditional mode. Oftentimes, the MRI conditional mode places the AIMD into a fixed rate therapy and disables sensing to make the AIMD less sensitive to disruption due to EMI during MRI scans. The RF switch 380 or 502 must remain in the N.C. position (the normal operating mode, THROW 1 in FIGS. 3A and 21) throughout the MRI scan. In Step 424, the MRI scans are safely performed. Step 426 re-programs the MRI after the MRI scanning is completed, and the patient is removed from the MRI scanner. The re-programming of Step 426 resets the patient's AIMD device to the pre-MRI scan AIMD settings, which once again enables the control signal 382. Referring to FIG. 3A, for the RF switch 380 of the present invention, this means that the RF switch again functions such that, at predetermined intervals, the RF switch 380 receives control signal 382, which toggles (switches) to the RF test mode (THROW 2 in FIG. 3A). Switch 502 of FIG. 21 can again switch to the THROW 2 (OPEN position) to disconnect the filter capacitors during delivery of an ICD pulse.

FIG. 21 illustrates the package outline and schematic for a SINGLE-POLE SINGLE-THROW RF switch (FIG. 17), which is similar to the SINGLE-POLE DOUBLE-THROW switch of FIG. 3A. As can be seen, in the normally closed (N.C.) position, the RF switch 502 connects the capacitor ground electrode plates 273,610,802 to the system ground 210, 103. The POLE or THROW of the RF switch is designed to be connected to filter capacitor ground electrode plates 273, 610 or 802 (in other words, the switch 502 can be reversed as it is SPST). The switch of FIG. 21 is controlled by an AIMD circuit board control signal 382. This control signal could be referenced to ground 397 or it could embody two separate electrical terminals 384 and 384' (not shown). Referring again to the RF switch of FIG. 21, in its N.C mode or THROW 1 POSITION, the RF switch is in its normal operating mode, which connects the ground electrode plates of the filter capacitor 270, 284, 288, 600, 800 to the system ground 210, 103. In an embodiment of the present invention, just prior to and during delivery of an ICD pulse, the AIMD electronics opens the RF switch 502 of FIG. 21 such that, in its THROW 2 POSITION, the RF switch is opened (not connected to the high-voltage circuit of the ICD). This effectively (meaning completely or at least partially) disconnects the filter capacitor so that it is not exposed to the ICD high-voltage pulse. As disclosed previously, this eliminates concerns over filter capacitor inrush current $i_c$, especially during the leading edge (rise time) of an ICD high-voltage pulse. The use of the SINGLE-POLE SINGLE-THROW RF switch 502 of FIG. 21 to disconnect the associated EMI filters during an ICD pulse is further illustrated in following and explained in the following figures.

Figure 22:
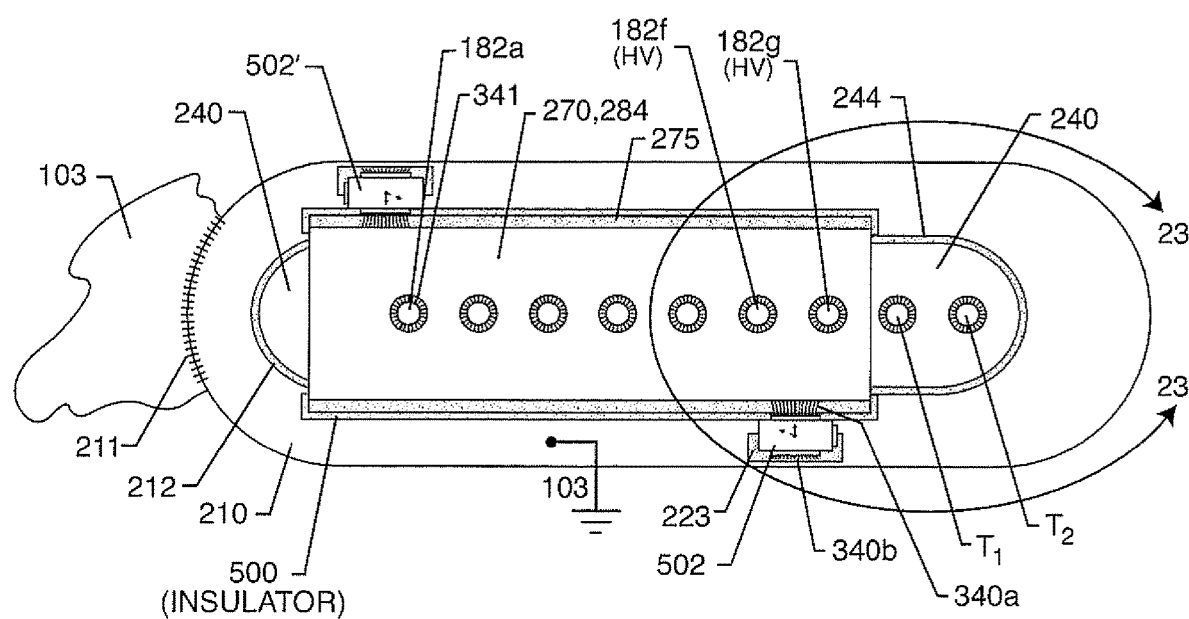
FIG. 22 illustrates two SINGLE-POLE SINGLE-THROW RF switches of FIG. 21 for disconnecting ground electrode plates of a filter capacitor during RF interrogation of an implanted AIMD lead(s).

FIG. 22 is similar to FIG. 3, except that there are two RF switches 502 and 502' which, in an embodiment, disconnect the ground electrode plates 273 of the filter capacitor 270, 284 from system ground 103 during either delivery of an ICD pulse; or, which, in another embodiment, disconnect the EMI filter 270, 284 in order to apply an RF test signal 382 to evaluate lead integrity in accordance with the present invention. In this embodiment, the RF switches 502, 502' are connected to the ground capacitor termination 275 of the filter capacitor 270, 284, as illustrated. The RF switch POLE is grounded, in this case, to a gold bond pad 223, which has been previously disclosed. Since RF switch 502 is a SPST ON-OFF switch, it will be appreciated that its THROW and its POLE can be reversed. There are a number of alternatives to gold pocket-pads 223, which provide an oxide-resistant electrical ground connection to the ferrule 210. Oxide-resistant electrical ground connections include electrical connections to metal additions, a hermetic seal gold braze, ground terminal pins laser welded or gold brazed to the ferrule 210, or oxide-resistant pocket-pads, an oxide-resistant metal layer or area, or an ECA stripe overlaid atop an oxide-resistant metal layer or area. Referring once again to FIG. 22, there are two unfiltered telemetry pins $T_1$ and $T_2$, as shown. All of the conductive pathways, such as the terminal pins or leadwires of FIG. 22, which include active conductors 182a to 182g, and the telemetry pin circuits $T_1$ and $T_2$, pass through the insulator 240 in non-conductive relationship with the ferrule 210.

FIG. 22A illustrates the active electrode plates 272 and the ground electrode plates 273 of the filter capacitor 270, 284 of FIG. 22. As known in the prior art and as disclose in the referenced patents, the active electrode plates and the ground electrode plates of FIG. 22 are interleaved in a capacitive relationship (sandwiched construction) such that the active electrode plates overlay the ground electrode plates forming an effective capacitance area (ECA). Depending on the voltage rating of the capacitance value desired, there could be a plurality of these interleaved active electrode plates 272 and ground electrode plates 273 stacked up and then pressed into a bar, which is then fired to form a monolithic structure (for ceramic filter capacitors). Referring once again to FIG. 22A, one can see that there is a ground capacitor metallization 275, which provides an electrical connection to the internal ground electrode plates 273. The RF switches 502 of FIG. 22 can selectively connect this ground 275 to system ground 103 or disconnect it.

FIG. 22B illustrates an alternative embodiment of the feedthrough capacitor 270, 284 of FIG. 22. In this case, the filter capacitor 270, 284 is elongated such that it overlays both telemetry pins $T_1$ and $T_2$. Referring to the ground electrode plate 273 of FIG. 22B, one can see that the capacitor ground metallizations (ground terminations) 275 are no longer on the long side of the rectangular filter capacitor but are disposed on the short ends of the filter capacitor. The ground electrode plate 273 has been configured to make electrical connection to capacitor ground metallizations 275, as shown. The RF switches 502 and 502' have been moved so that they are in line with the filter capacitor of FIG. 22. It is appreciated that the RF switches connect from the capacitor ground metallizations 275 to the system ground 103 as schematically illustrated in FIG. 22B. RF switches 502 and 502', as illustrated in FIGS. 22 and 22B, switch (toggle) ON and OFF together almost simultaneously. The RF switches are switched by the control signal 382 out of the normal operating mode and opened up during both delivery of an ICD pulse or, in another embodiment, during application of an RF test signal 382 to any of the active terminal pins of the hermetic feedthrough of FIG. 22, where in this embodiment the active terminal pins are 182a through 182g. In particular, for an ICD, the RF test signal 382 would be injected into (sent down) the implanted high-voltage shocking leads of an AIMD to interrogate the integrity of said implanted leads, which are associated with terminal pins 182f and 182g. For example, conductive pathways such as terminal pin 182f and 182g can be associated with an implanted lead shocking electrode in the superior vena cava (SVC) and a right ventricle high-voltage shocking electrode in the right ventricle (RV). Referring once again to FIG. 22B, there is a downside to selectively disconnecting the entire set of ground electrode plates 273. Opening the switches does not completely remove the capacitances from the pulse circuit because a series capacitance is formed between terminal pins 182f and 182g by the overlay of their associated active electrode plates 272 and the common ground electrode plates 273. In the embodiment of FIG. 22, it is noted that the series capacitances are associated with each of the active conductive pathways. For a differential HV ICD pulse that is applied between terminals 182f and 182g this results in a series line-to-line capacitance, which divides the capacitance in half, and in accordance with the equation of FIG. 12 for $i_c$, means that the capacitance is subject to one half of the pulse inrush current $i_c$. RF switch embodiments that eliminate this series capacitance and therefore eliminate filter capacitor pulse inrush current $i_c$ are shown in FIG. 6 and will be further shown and explained in subsequent figures herein.

Referring once again to FIG. 22B, one can see that each active electrode plate or set of the active electrode plates 272 associated with active terminal pins 182f, 182g overlap with a ground electrode plate or set of ground electrode plates 273, thereby creating capacitance. This means that a capacitance forms in series between conductive pathways 182f and 182g. Certain biphasic ICD shocks can be programmed to create defibrillation vectors in the heart between the RV 182f and the SVC 182g leadwires. This means that a high-voltage pulse would appear across the two series capacitances associated with conductive pathways 182f and 182g. Series capacitors divide voltage between them, so the capacitors do not need to be rated quite as high in voltage as a capacitor directly exposed to the high-voltage pulse between terminal pins 182f and 182g and the system ground 103. Also, the current surge $i_c$ in these series capacitances are reduced by half because the total capacitance value for the capacitors in series is reduced by half (this is assuming that the filter capacitors are of equal value, which is generally true). This is best appreciated by referring to the equation of FIG. 12, which shows that the capacitor inrush current $i_c$ is proportional to the capacitance value C times dV/dT. So, halving the capacitance value (for two equal capacitors in series) halves the capacitor inrush current $i_c$. In summary, for the switching arrangement illustrated in FIGS. 22, 22A and 22B, one still has to consider that a high-voltage ICD pulse may appear across terminal pins 182f and 182g, where the series capacitance is present. Accordingly, one has to design the filter series capacitances/capacitors associated with terminal pins 182f and 182g for one half of the ICD high-voltage pulse and one-half of the inrush current $i_c$.

Figure 23:
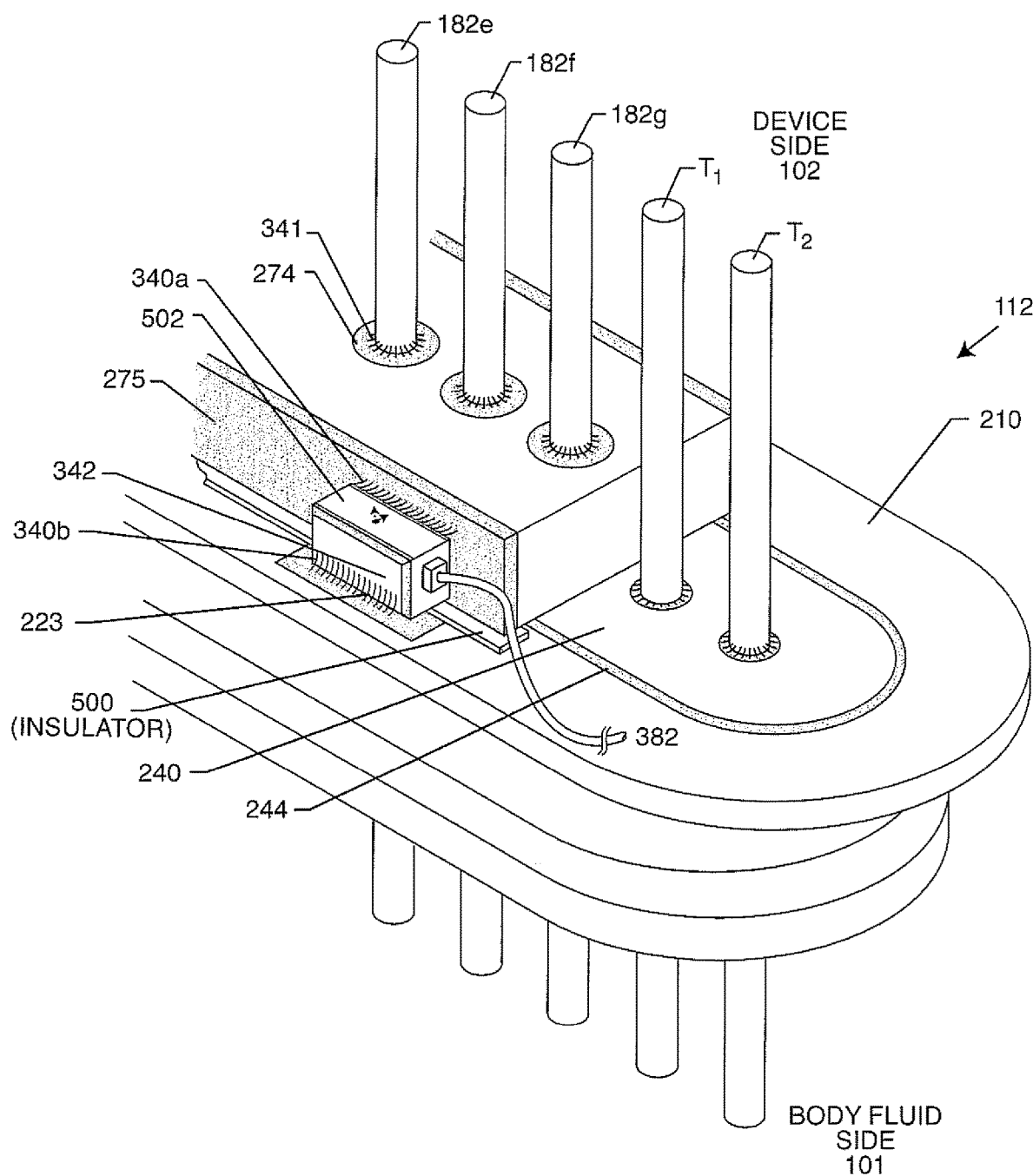
FIG. 23 is taken from section 23-23 of FIG. 22 showing an isometric view of the RF switch attachment.
Figure 24:
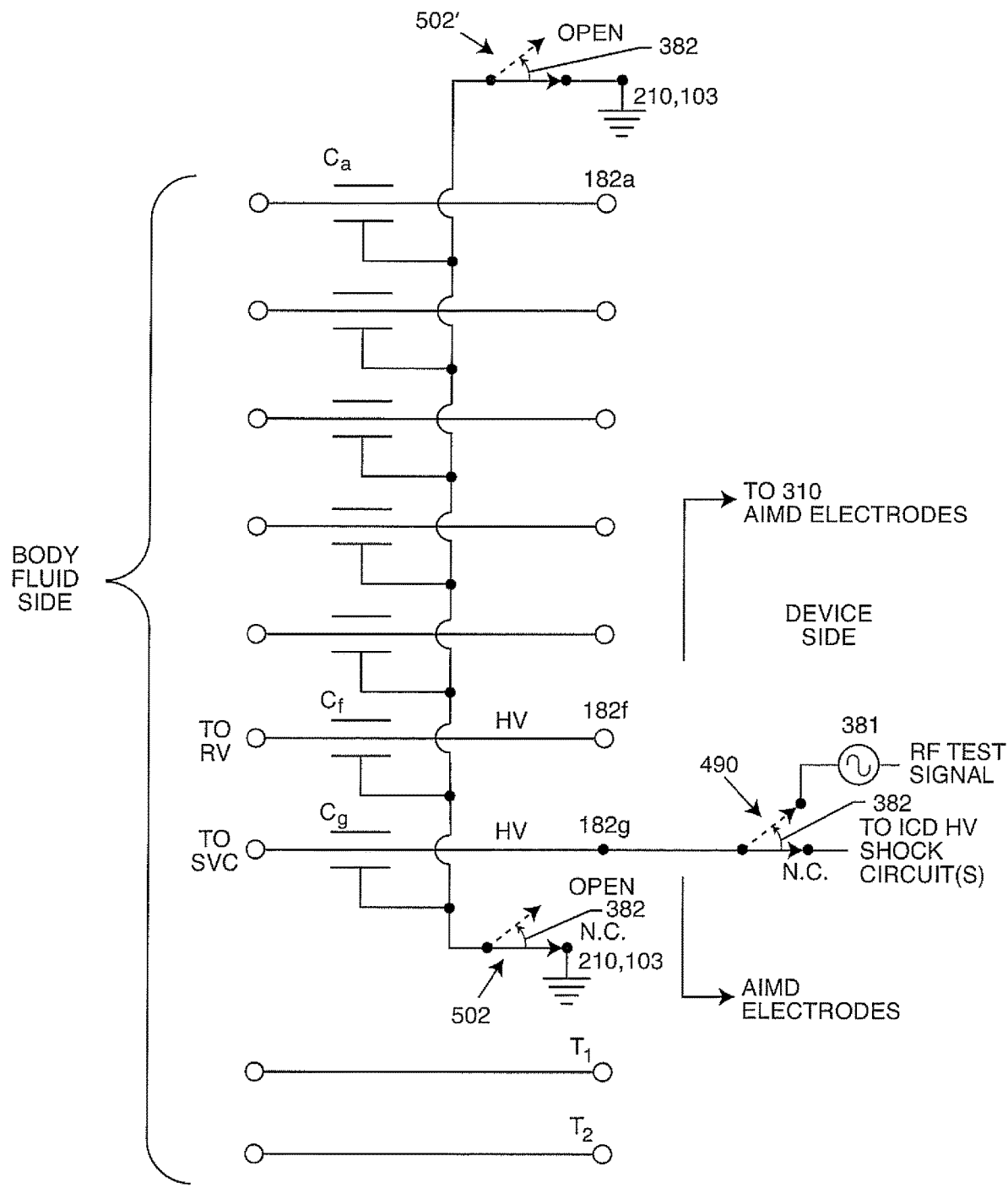
FIG. 24 is the electrical schematic diagram of the filter capacitor and RF switches of FIG. 22.

FIG. 23 is a blown-up isometric view taken from section 23-23 of FIG. 22. Illustrated is an RF switch 502 connected to the ground capacitor termination 275 at THROW 1 and at the RF switch-POLE to a gold pocket-pad 223, which is also a system ground 210, 103. As previously disclosed, when the RF switch is disconnected, it will switch (toggle) to an OPEN POSITION (THROW 2). Referring once again to FIG. 23, the RF switch orientation does not matter. In other words, the THROW could be towards the ground capacitor termination 275 or towards the gold pocket-pad 223, and then to the system ground 103. Referring once again to FIG. 23, one can see the AIMD control signal 382, which is routed from the AIMD electronic circuit board (not shown), such as an ASIC circuit board. In a normal operating mode, the RF switch 502 remains in the THROW 1 POSITION as shown. Upon application of a control signal 382, the RF switch 502 opens in accordance with the present invention.

FIG. 24 is a detailed electrical schematic diagram of the RF switch circuits of FIGS. 22 and 23. The schematic shows a feedthrough capacitance Ca through Cg associated with each active terminal pin 182a through 182g. The schematic also indicates that the high-frequency telemetry pins $T_1$ and $T_2$ are not associated (in other words, are insulated from) the EMI filter capacitors Ca and Cg. When the RF switches 502 and 490 are in their normal operating modes or N.C. position, the EMI filter capacitors Ca through Cg are properly grounded to a system ground 210, 103 as indicated. Therefore, EMI RF filtering is enabled. Switch 490 is physically located on an AIMD electronic circuit board (not shown) and can be embedded within the logic of an ASIC chip. There are many functions possible with the schematic of FIG. 24. The first function is for all the RF switches 502, 502' and 490 to remain in their normal operating mode (N.C.) positions. In the first function, EMI filtering is enabled, and the ICD can operate normally delivering therapeutic pulses or ICD pulses if necessary to the patient. In a test mode, wherein an RF test signal 382 is injected into (sent down) an implanted lead, the RF switches 502, 502' and 490 are all switched from their normal operating positions. RF switches 502 and 502' are switched to their OPEN position, which disconnects the EMI filters Ca through Cg from system ground 210, 103. At the same time, RF switch 490 is switched from its normal operating position (N.C.) position to the RF test signal 381. With RF switches 502 and 502' opened, the EMI filter capacitors are disconnected, which allows the RF test signal 381 to be applied to the high-voltage implanted shocking lead 182g to the SVC as indicated. As previously disclosed, an RF test signal 381 is applied to evaluate the integrity of an implanted AIMD lead, including lead body anomalies, lead body insulation issues, lead body conductor-to-conductor insulation issues, lead body fractures, lead body dislodgements and the like.

Referring once again to FIG. 24, only one switch 490 is illustrated in the schematic, however, it is appreciated that another (or as many as needed) RF switch(es) 490 could also be associated with the other high-voltage shocking lead 182f, which is directed to a right ventricle (RV) electrode. It is further appreciated that RF switches 490 and RF test signals 381 can be associated with any of the other implanted leads as well in order to access their integrity (the other implanted leads are also known as low-voltage therapy delivery and low voltage biologic sensing signal implanted leads).

Referring again to FIG. 24, in another mode, that is for delivery of an ICD pulse, RF switches 502 and 502' are OPEN and the RF switch 490 control signal 382 is disabled such that RF switch 490 has to remain in its normal operating mode. Opening RF switches 502 and 502' while disabling RF switch 490 allows delivery of a high-voltage ICD shock to terminal pins or conductive pathways 182g and 182f (not shown). Referring once again to the schematic of FIG. 24, one can trace the circuit and see that there is a series capacitance formed between Cf and Cg (the RV filter capacitance and the SVC filter capacitance are in series through their common ground electrode plate). This means if a biphasic pulse is applied between terminals 182f and 182g, then a high-voltage polarity will occur between terminals 182f and 182g, and with the two capacitors Cf and Cg in series. This means that there will still be a significant capacitor inrush current $i_c$, however, in accordance with the equation of FIG. 12, the inrush current $i_c$ is reduced by half. A preferred embodiment is illustrated in FIG. 6 and further illustrations of subsequent figures follow in which capacitors Cf and Cg are no longer in series so that one does not have to worry about capacitor inrush current $i_c$ at all during application of an ICD pulse.

Figure 25:
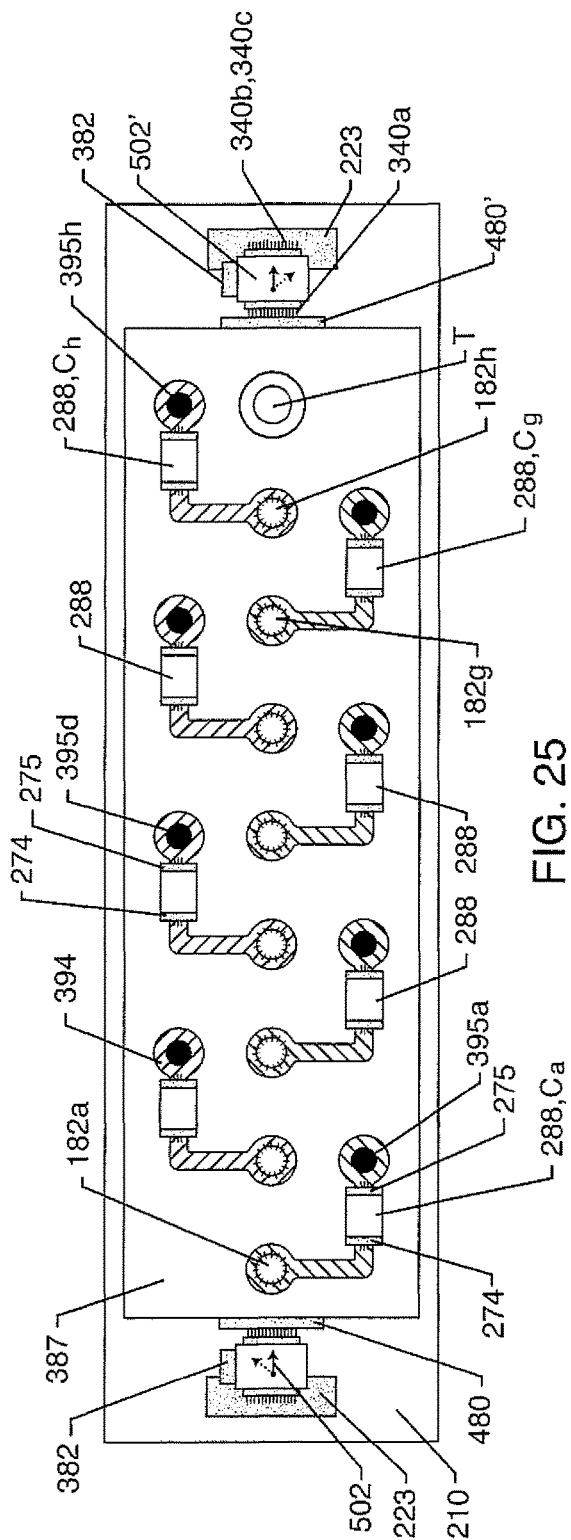
FIG. 25 illustrates the top view of a circuit board populated with two-terminal MLCC chip capacitors, wherein the ground electrode plane or ground electrode plate of the circuit board is connected to system ground through two SINGLE-POLE SINGLE-THROW RF switches of FIG. 21.
Figure 26:
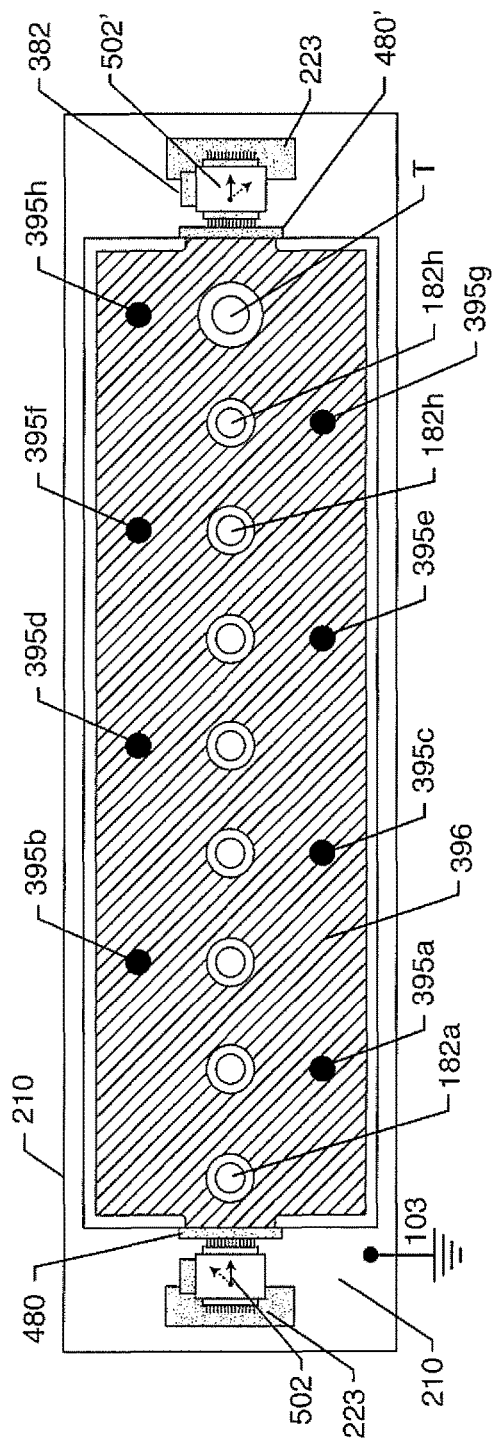
FIG. 26 is similar to FIG. 8 except in this embodiment the two RF switches are disposed on the device side of the ferrule of the hermetic feedthrough adjacent to the circuit board in order to disconnect the circuit board ground electrode plane or ground electrode plate and to isolate the filter capacitors from system ground during high-voltage shock therapy and/or RF signal interrogation.

FIG. 25 is a view of the top side of the device side of a circuit board 387 on which MLCC chip capacitors 288 are disposed. Circuit boards have been thoroughly disclosed in U.S. Pat. No. 8,195,295 and its family previously incorporated herein by reference. The circuit board 387 can comprise various rigid or flexible materials, including, but not limited to, FR4 board, alumina boards, fiberglass boards and the like. Each one of the active terminal pins 182a through 182h is associated with a filter capacitor 288 as shown. As previously disclosed, these filter capacitors 288 perform better at higher frequencies if they are reverse geometry filter capacitors, which is preferred to reduce parasitic inductance and increase high frequency filter performance. As shown in FIG. 25, the filter capacitors in this embodiment comprise a regular geometry, meaning that the filter capacitors are terminated along the short sides of the rectangle (this undesirably increases parasitic inductance). The circuit board 387 of FIG. 25 has at least one internal ground electrode plate 396, which is illustrated in FIG. 26. This internal ground electrode plate is also a shield plate, as is disclosed in the '295 patent. The shield plate performs the same function as the ground electrode plates of a feedthrough capacitor when it is installed over a hermetic seal insulator 240 (not shown). It is known by electromagnetic interference engineers that closely held electromagnetic interference emitters, such as cellular telephones, can produce radiated interference that would pass right through an insulator 240. Accordingly, the ground electrode plate or shield plate 396 of FIG. 26 absorbs and reflects such radiated EMI thereby preventing EMI from getting inside of the AIMD housing, where it could dangerously cross-couple to sensitive circuits and disrupt their function. It is marginally permissible to have small areas of the insulator 240 unshielded as shown around the telemetry pins $T_1$ and $T_2$ of FIG. 22. One has to perform complex waveguide analysis to be certain of the waveguide beyond cutoff frequency. The filter capacitor of FIG. 22B is superior as the insulator openings around $T_1$ and $T_2$ are much smaller. To understand waveguide principles, all one has to do is look carefully through the glass door of a microwave oven. There is a metal plate with carefully sized holes drilled in it that one can see through. These hole diameters are designed to be waveguides beyond cutoff meaning that the very high amplitude (and potentially dangerous to human tissue) 2.45 MHz microwave energy that cooks food cannot escape the microwave oven. If one were to drill out the holes by even only a few millimeters in this microwave oven waveguide shield, then the microwave oven would emit extremely dangerous (to human tissues) levels of RF microwave energy into the room.

Referring once again to FIG. 25, one can see that there are two RF switches 502 and 502' of the present invention. These RF switches are SINGLE-POLE SINGLE-THROW RF switches, as previously disclosed in FIG. 21. These SPST RF switches 502 and 502', when in the normal operating mode, connect the circuit board ground plates 396 to system ground 210, 103, which in this embodiment, is a gold pocket-pad 223. A gold pocket-pad 223 provides an oxide-resistant attachment surface to what is generally a titanium ferrule 210 (bare titanium is prone to oxidation). RF switches 502 and 502' are controlled by an RF switching control signal 382 coming from an AIMD circuit board (such as an ASIC). When the RF switch control signal 382 is sent to RF switches 502, 502', the RF switches toggle (switch) from a normal operating position (N.C. also known as THROW 1) to an OPEN position. In the OPEN position, the circuit board ground plates 396 are disconnected from system ground 210, 103. This means that the ground electrode plates 396 are electrically floating (insulated) with reference to the ferrule 210 and the AIMD housing 103. As previously disclosed, this means that the filter capacitors 288 cannot decouple RF signals from their associated conductive paths or terminal pins 182a through 182h. Accordingly, an RF test signal 381 of the present invention can be applied to any one or even all of these conductive pathways or terminal pins 182a through 182h. One application of the RF switch, as illustrated in FIGS. 25 and 26, is to disconnect the filter capacitor from system grounds 210, 103 when an RF test signal 381 is injected to interrogate and evaluate the integrity of an implanted AIMD lead. Another application of the RF switches of FIGS. 25 and 26 is to OPEN them up in the event that a cardioverter defibrillator is about to deliver a high-voltage pulse, for example, to deliver a high-voltage pulse to conductive pathways 182g and 182h. This configuration, however, has the same limitations as previously disclosed, in that, capacitors Cg and Ch that are associated with conductive pathways or terminal pins 182g and 182h are in series with each other such that a differential voltage between these terminal pins still cause a capacitor inrush current $i_c$. Again, having these two filters capacitors in series means the inrush current $i_c$ is halved, nonetheless, one still needs to consider this inrush current $i_c$ in the design and selection of the filter capacitors 288, as the filter capacitor 288 still need to be pulse-rated.

Figure 27:
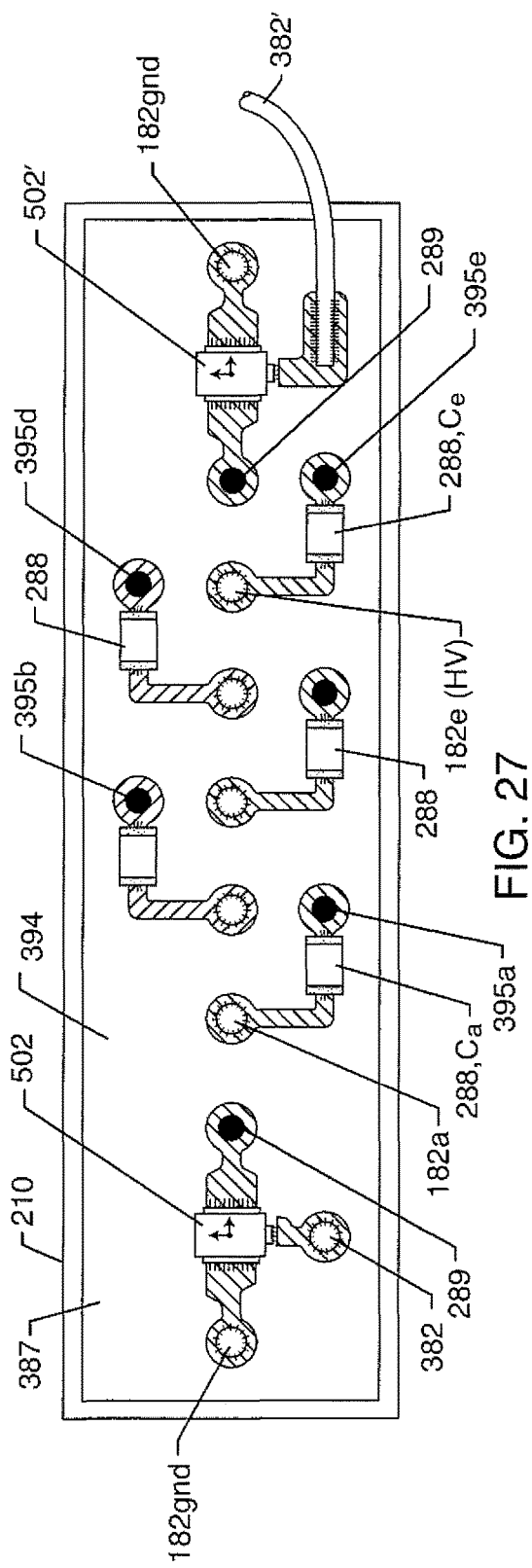
FIG. 27 illustrates the top view of an alternative embodiment of a circuit board. In this embodiment, the switches of FIG. 21 are surface-mounted onto the circuit board in order to connect or disconnect the circuit board ground electrode plate such that the filter capacitors are isolated from system ground.
Figure 28:
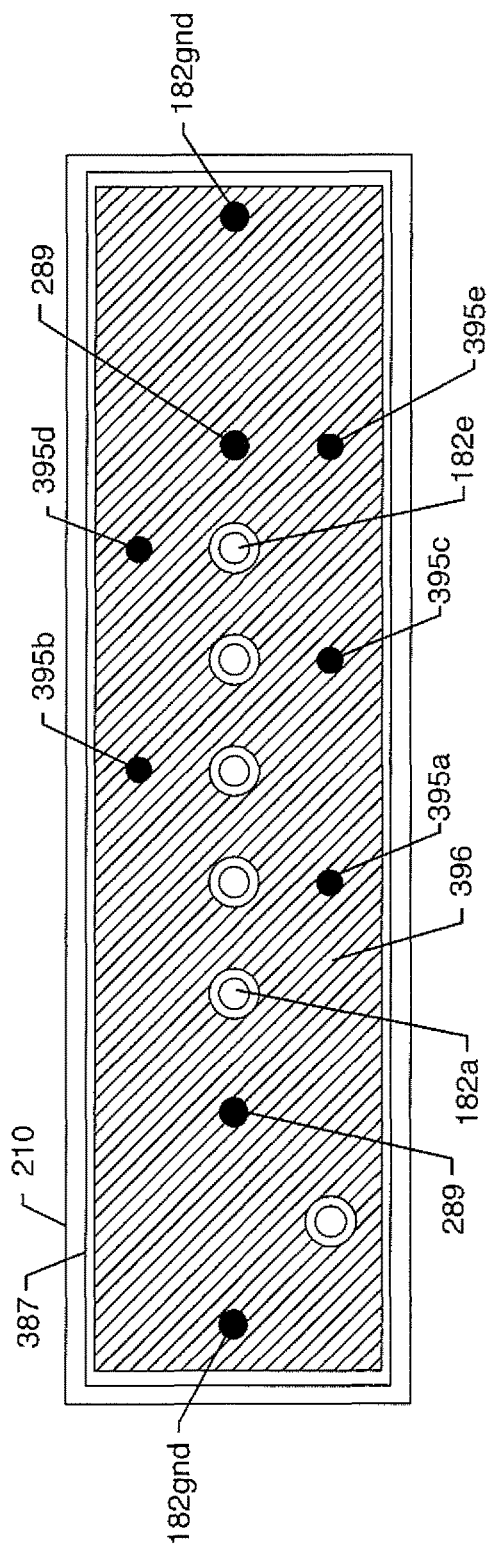
FIG. 28 is the ground electrode plane or ground electrode plate of the circuit board of FIG. 27.

FIG. 27 is very similar to FIG. 25, except that the RF switches 502 and 502' are surface mounted directly to the circuit board 394. For simplicity, the number of active conductive pathways are reduced to five (182a through 182e). There are also two ground terminal pins 182gnd, which can be electrically and mechanically attached to the ferrule 210 by laser welding or gold brazing. The ground terminal pins 182gnd comprise an oxide-resistant material as taught in FIGS. 95, 96 and 97 of U.S. Pat. No. 8,295,195. The oxide-resistant material of the ground terminal pins 182gnd may be selected from the group consisting of platinum, gold, tungsten, iridium, palladium, niobium, tantalum, ruthenium, rhodium, silver, osmium, and alloys or combinations thereof. The oxide-resistant material of the ground terminal pins 182gnd may further be selected from the group consisting of platinum based materials including platinum-rhodium, platinum-iridium, platinum-palladium, or platinum-gold and naturally occurring alloys such as platiniridium (platinum-iridium), iridiosmium and osmiridium (iridium-osmium). It is important to note that the oxide-resistant ground terminal pins 182gnd provide strong mechanical, low resistance and low impedance filter-system electrical ground connection to the ferrule 210 and the housing 103 (not shown). In the normal operating position (N.C.), the RF switches 502 and 502' provide a connection between the ground terminal pins 182gnd and the circuit board ground vias 289. Circuit board ground vias 289 connect the ground circuit traces associated with the ground side of each RF switch 502 and 502' and the circuit board internal ground plate 396 of FIG. 28. The operation of the RF switches 502 and 502' is the same as disclosed for FIGS. 25 and 26. Again, there is a downside to the circuit board layout of FIG. 27, in that, if a differential high-voltage signals is applied, for example, between terminal pins 182d and 182e, the associated filter capacitors 288 appear in series, hence consideration must be given to designing said filter capacitors for half of the capacitor inrush current $i_c$.

Figure 29:
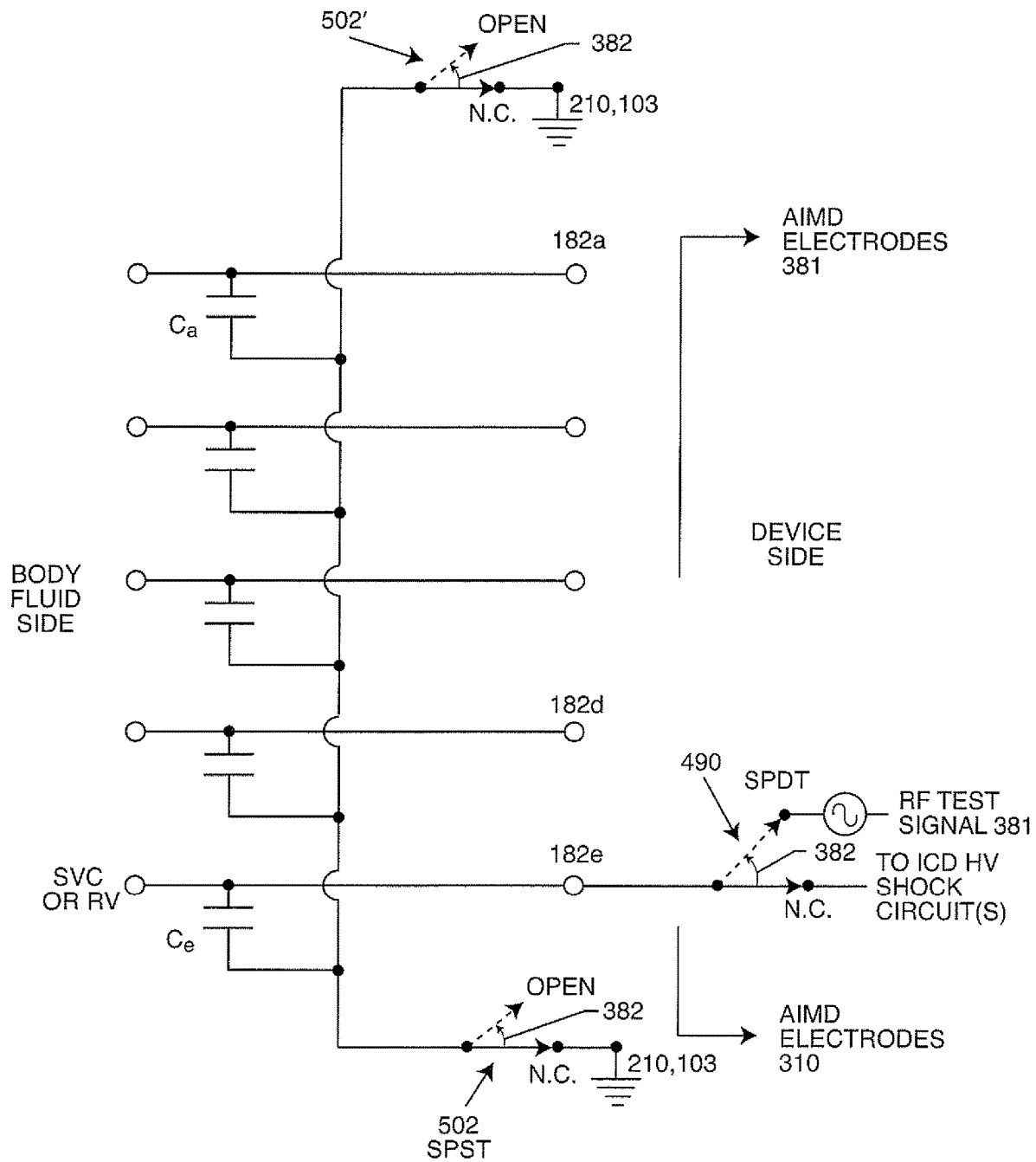
FIG. 29 is the electrical schematic diagram of the circuit board of FIG. 26.

FIG. 29 is an electrical schematic of the circuit board of FIG. 27, illustrating 5 active conductive pathways, the active conductive pathways being terminal pins 182a through 182e. The active terminal pins 182a through 182e are associated with capacitances Ca through Cf. In this embodiment, there is only one high-voltage shocking pathway 182e illustrated (typically there would be two high-voltage shocking pathways). It is noted that conductive pathway or terminal pin 182f can be converted into an SCV or RV HV shocking channel. It is appreciated that both an SVC and an RV HV conductive pathway can be made by converting terminal pins 182d and 182e respectively. As previously disclosed, for application of a high-voltage shock, RF switches 502 and 502' are OPEN, thereby disconnecting the circuit board ground 396 from the system ground 210, 103. Opening RF switches 502 and 502' disconnects capacitors Ca through Cf from the system ground 210, 103. This enables the RF test signal 381, but as one can see by reviewing the electrical schematic of FIG. 29, the problem previously disclosed regarding capacitors being in series still exists during a differential high-voltage pulse between 182d and 182e. Another application of the circuit of FIG. 29 is to OPEN the RF switches 502 and 502' so that the AIMD electronics are disconnected from the high-voltage shock circuitry and instead are connected to an RF test signal 381 to evaluate the integrity of the implanted AIMD lead. It is appreciated that the RF switch 490 that is associated with the RF test signal 381 can comprise multiple RF switches 490, wherein the RF test signal 381 can be applied to any or even all of the conductive pathways 182a through 182f.

FIG. 30 is another embodiment of the circuit boards previously disclosed in FIGS. 25 and 27. In this embodiment, there are still two RF switches 502 and 502', however, the RF switches in this embodiment have been relocated. The RF switches 502 and 502' are surface mounted with the filter capacitors 288 on the circuit board 387. The circuit board internal ground plate 396 is grounded through oxide-resistant ground terminal pins 182gnd that are electrically and mechanically attached to the ferrule 210 by a laser weld or a gold braze (not shown). Referring to the filter capacitors 288 of FIG. 30, the filter capacitors associated with conductive pathways or terminal pins 182a through 182f are grounded to ground plane 396 and, in turn, to the system ground 210, 103. These filter capacitors are, therefore, operational at all times to provide EMI filtering. On the other hand, the filter capacitors 288 that are associated with the conductive pathways or terminal pins 182g and 182h are high-voltage ICD shock pathways and are only connected from the active pathway to ground when the switches 502 and 502' are in their normal operating (N.C) 1st THROW positions. Referring once again to FIG. 30, it is appreciated that it does not matter on which side of the MLCC capacitor 288 that the RF switches 502, 502' are disposed since these RF switches are in series. When the RF switches are OPEN, the MLCC chip capacitors will either be disconnected from ground or will be disconnected from the active terminal pin, which in a series circuit, opens the circuit and thereby eliminates any series capacitance and thus prevents (reduces to zero) any capacitor surge current $i_c$ during application of an ICD pulse. Accordingly, when the RF switches 502 and 502' of FIG. 30 are both in the OPEN position, and a high-voltage pulse or even a differential pulse is applied to terminal pins 182g and 182h, then the capacitors 288 will not be subjected to the ICD high voltage pulse or any capacitive surge current $i_c$. In other words, in this embodiment, the pulse inrush current $i_c$ equals zero. This is very important as this means that commercial off the shelf low-voltage capacitors can be used at all points on the embodiment of this circuit board, both for the low-voltage circuits 182a through 182f and also the high-voltage pulse circuits 182g and 182h. Again, in this embodiment, commercial off the shelf low-voltage capacitors can be used at all points the circuit board because, during application of a high-voltage pulse, the filter capacitors associated with terminal pins 182g and 182h are disconnected both from system ground 210, 103 and from each other by the RF switches 502 and 502'. In accordance with the present invention, RF switches 502 and 502' of the circuit board 387 of FIG. 30, can also be directed to OPEN by a control signal 382 to apply an RF interrogation test signal 381 to one or both of the lead terminal pins 182g and 182h for the purpose of evaluating the integrity of an implanted AIMD lead, in particular, an implanted high-voltage RV or SVC lead associated with a high-voltage shock electrode.

Figure 31:
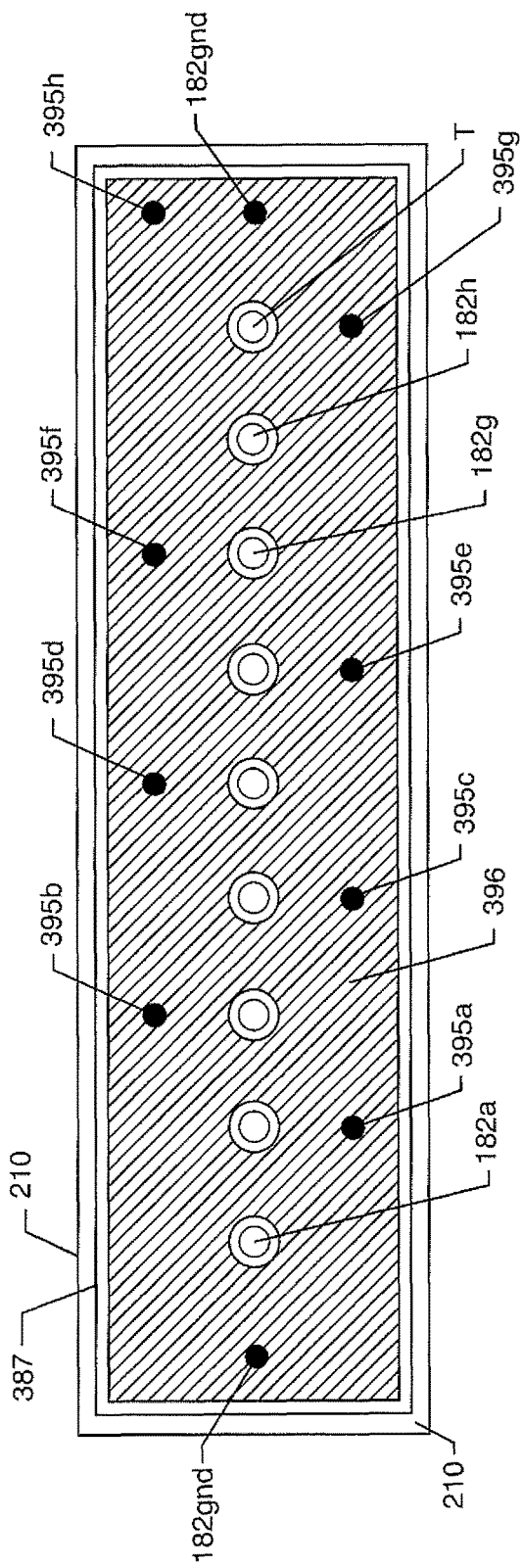
FIG. 31 illustrates the at least one internal or external ground plate of the circuit board of FIG. 30.

FIG. 31 illustrates the ground electrode plate of the circuit board of FIG. 30. As previously disclosed, a circuit board can have a single ground electrode plate or a plurality of ground electrode plates either embedded inside of a multi-layer circuit board 396 or disposed between the bottom of the circuit board and the insulator, as taught in U.S. Pat. No. 8,195,295. One can see that the circuit board ground electrode plate 396, as illustrated in FIG. 31, is grounded at both of its ends to the ferrule of the hermetic feedthrough using oxide-resistant ground terminal pins 182gnd. These oxide-resistant ground terminal pins 182gnd are mechanically and electrically connected to the ferrule of the hermetic feedthrough by a laser weld or gold braze 225. FIG. 4E previously disclosed, illustrates such a ground terminal pin 182gnd. The circuit board ground electrode plate or plates 396 also provide a grounding point (circuit board ground vias 395) for each one of the filter capacitors 288 (grounding points 395a through 395h, as shown). The ground electrode plate 396 is relatively wide, which reduces its parasitic inductance, thereby providing a low impedance ground point at points 395a through 395h. In circuit board art, these low impedance ground points are typically closed conductive vias or eyelet vias or filled vias, which provide an inner electrical connection to the ground circuit traces of FIG. 30 and to the internal ground electrode plate(s) 396 of the circuit board. Referring once again to FIG. 31, one will appreciate that the two ground terminal pins 182gnd shown connected to ground electrode plate 396 can be a plurality of ground terminal pins up to and including "n" ground terminal pins as required to effect a low impedance, multi-point grounding system.

Figure 32A:
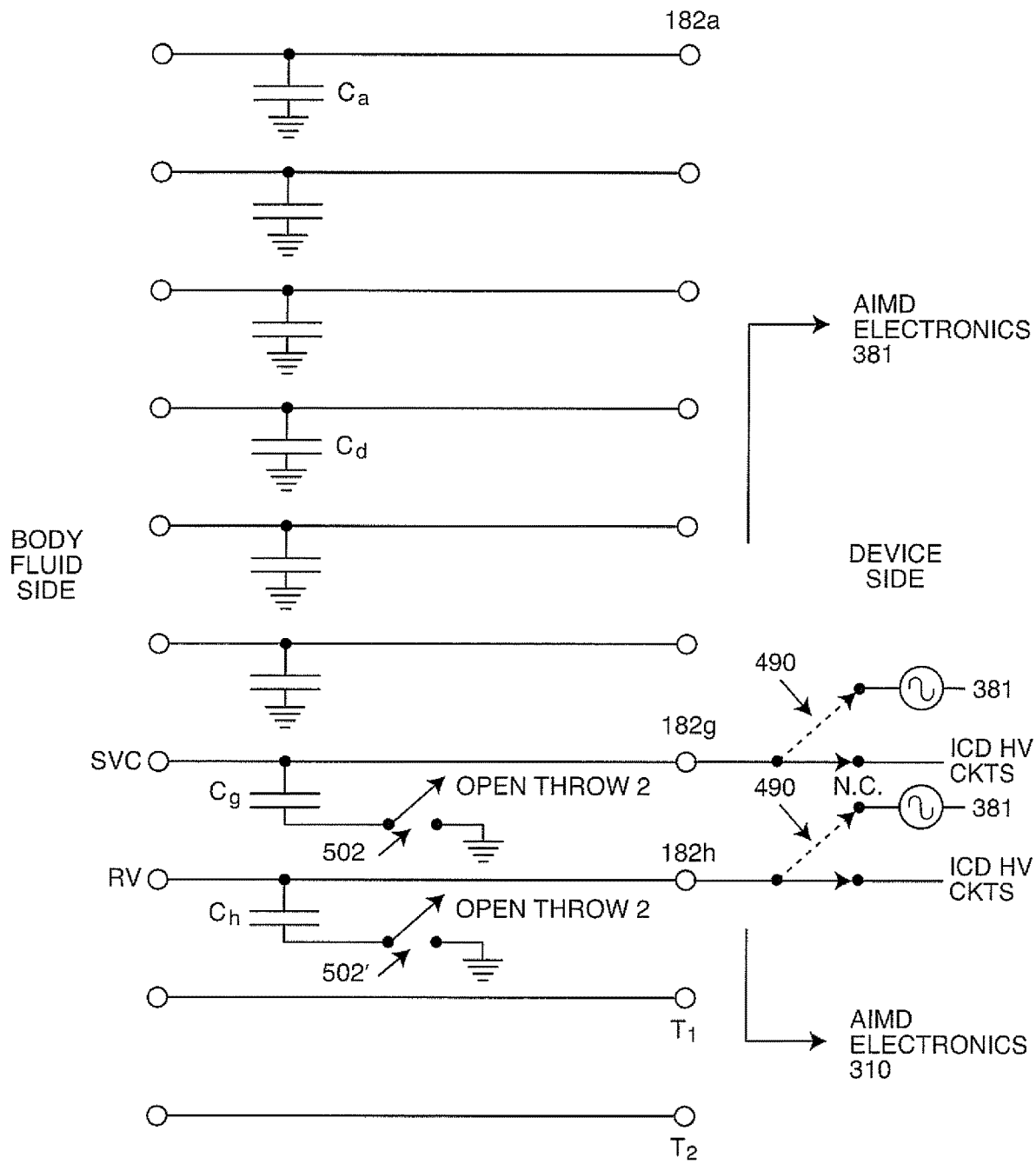
FIG. 32A is one possible electrical schematic of the circuit board of FIG. 31

FIG. 32A is an electrical schematic diagram of the circuit board of FIG. 30, illustrating a filter capacitor 288 associated with each one of the terminal pins 182a through 182f at all times. However, when RF switches 502 and 502' are OPEN, capacitors Cg and Ch are completely disconnected from ground and, therefore, are disconnected from each other in series. This is a significant advantage during application of an ICD pulse with RF switches 490 in their normal operating (N.C.) positions. As such, by completely disconnecting the filter capacitors Cg and Ch, said filter connectors Cg and Ch need not be high-voltage or even surge pulse-rated filter capacitors. This means that commercial off the shelf (COTS) filter capacitors 288 can be used, in particular, the reverse geometry filter capacitors of FIG. 4C. The filter capacitors can also be physically much smaller (which further reduces parasitic inductance) and are also much less expensive than are high-voltage (HV) pulse-rated custom filter capacitors. As previously disclosed, complete disconnection of the HV filter capacitors enables all of the filter capacitors 288 of FIG. 30 to be a low-voltage design including a reverse geometry filter capacitor. Reverse geometry filter capacitors significantly improve high frequency filter performance but reduces high-voltage standoff (potential to arc over). Filter capacitors 288 and RF switches 502,490 can all be robotically placed on circuit board 387, electrically attached and even electrically tested by tape and reel robotic/automated manufacturing processes.

The MRI mode of the RF switches 380 of FIG. 20 is equally important to the RF switches 502, 502' and 490 of FIG. 32A, meaning that said RF switches must remain in their normal operating mode (N.C. position) throughout any patient MRI scans. This means that EMI filtering is enabled throughout MRI scans at which time it would not be possible to inject an RF test signal 381 because the filter capacitors 288 would attenuate said RF test signal.

Referring once again to the electrical schematic of FIG. 32A, RF switches 502 and 502' are shown in their OPEN position and the AIMD electronic RF switches 490 are shown in their CLOSED or N.C position. So, this is the set up for application of a high-voltage ICD shock to the SVC and the RV. Again, one can see with the RF switches 502 and 502' opened, it is not possible for any pulse inrush current $i_c$ to flow through filter capacitors Cg or Ch, as these filter capacitors are completely disconnected and are no longer in series. In addition, because these filter capacitors are completely disconnected, the filter capacitors Cg and Ch are also not exposed to the high-voltage shock voltage itself (this enables the use of the reverse geometry MLCC chip capacitors 288 of FIG. 4C). In another embodiment, when the RF switches 502 and 502' are in the OPEN position as shown, by direction of a control signal 382, the RF switch 490 is switched to the SECOND THROW position, which means that the switch POLE would be connected to the RF test lead interrogation source 381. In this way, EMI filtering is disabled and the RF test signal 381 can be injected into the SVC and RV implanted leads so that detection circuits can interrogate the reflected test signal S1,1 for any lead anomalies.

It is important that, during the RF test signal test 381, the filter capacitors Cg and/or Ch are disconnected, or these filter capacitors would undesirably attenuate the RF test signal to the point wherein both the incident and the reflected signal would be so weak that it could not be detected (i.e., couldn't work). Referring once again to FIGS. 30 and 32A, it is appreciated that the circuit board 387 and the RF switches 502 are greatly simplified, in that, the RF switches are SINGLE-POLE SINGLE-THROW (SPST) compared to SPDT switches 380. These RF test switches 380,502 themselves do not need to be connected to the RF source 381 (this function could easily be accomplished on the AIMD electronic circuit board or ASIC). Therefore, manufacturing of the filter circuit board is simplified and RF switches 502 and 502' are also simplified, in that, these RF switches do not need to be multi-POLE switches, as previously disclosed for RF switches 380. The circuit board layout of FIG. 30 lends itself to high volume, robotic manufacturing operations where pick-and-place robots would place BGA bumps or solder dots or thermal-setting conductive adhesive dots and then place the various components to achieve the various electrical connections as indicated. For simplicity, the electrical connections do not have element numbers, but it is appreciated that all of the MLCC chip capacitors have terminations electrically connected to their associated circuit trace or via hole and that the RF switches 502 and 502' also have electrical connections or capacitor metallizations or terminations that are electrically connected to their respective circuit traces as indicated. The control wiring circuits 382 are not shown, but it is appreciated that the control wiring circuits are also be associated with their respective circuit traces and via holes to facilitate connection to an AIMD circuit board (ASIC electronics not shown).

Figure 32B:
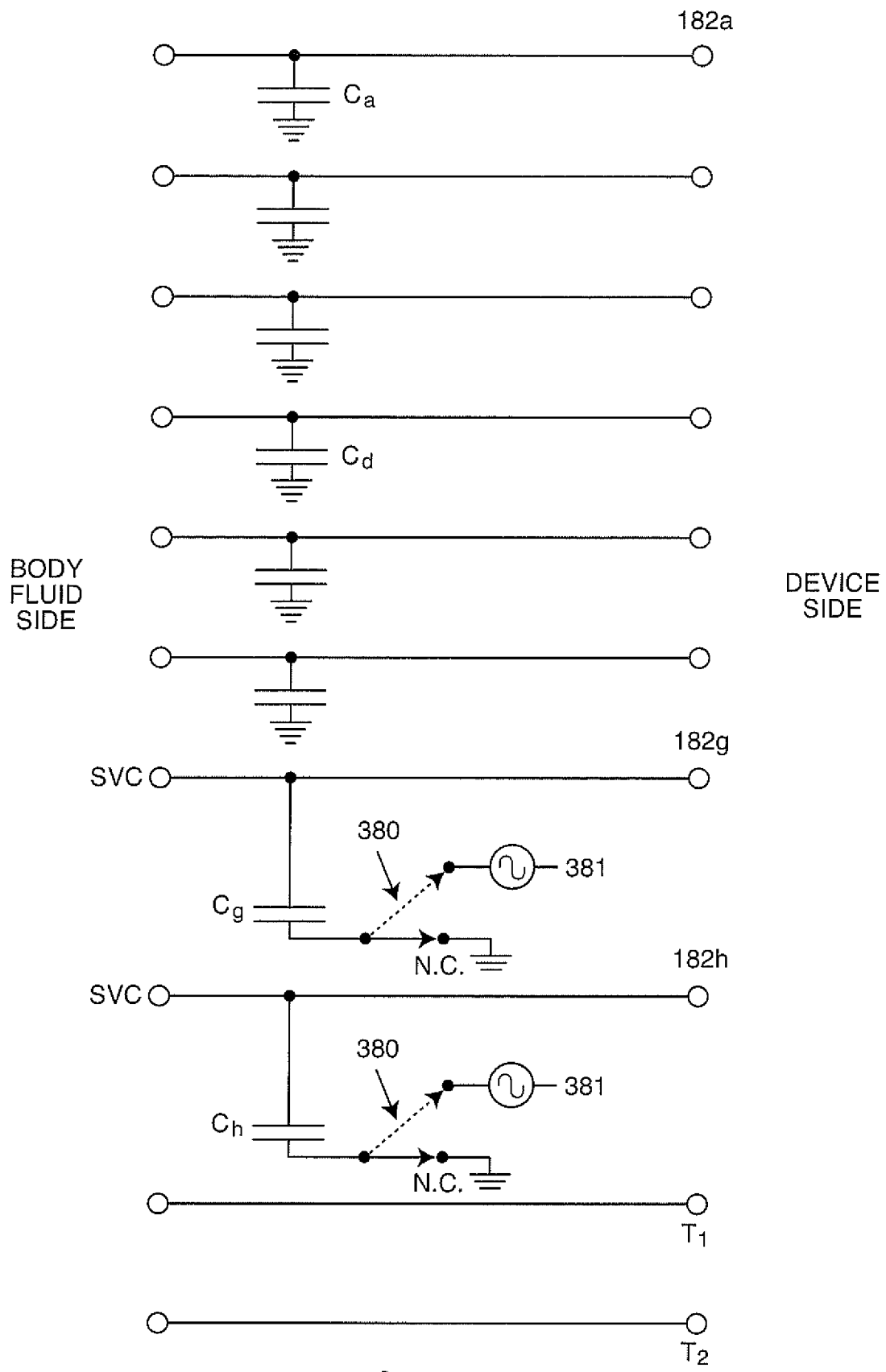
FIG. 32B is an alternative electrical schematic of the circuit board of FIG. 31

FIG. 32B is similar to FIG. 32A except that RF switches 490 are eliminated and replaced by DOUBLE-POLE RF switches 380. In this simplified electrical schematic, the RF switch function 490 and the control logic to apply test signal 381 are part of the AIMD main circuit board active (ASIC) electronic programming.

FIG. 33 is an isometric view of a prior art flat-thru capacitor. Flat-thru capacitors were previously disclosed in U.S. Pat. No. 8,195,295 and offer three-terminal filter performance similar to a feedthrough filter capacitor. The flat-thru capacitor of FIG. 33 is a quad polar device meaning that there are four active electrode plates 610 as illustrated in FIG. 34. These active electrode plates are interleaved with ground electrode plate 612 as shown. The active electrode plates are overlaid in a capacitive relationship with the ground electrode plate 612. There are ground capacitor metallizations or terminations 602 and 604 as illustrated. Flat-thru capacitors 614 are well known in the prior art and are sold in various manufacturers online catalogs.

Figure 35:
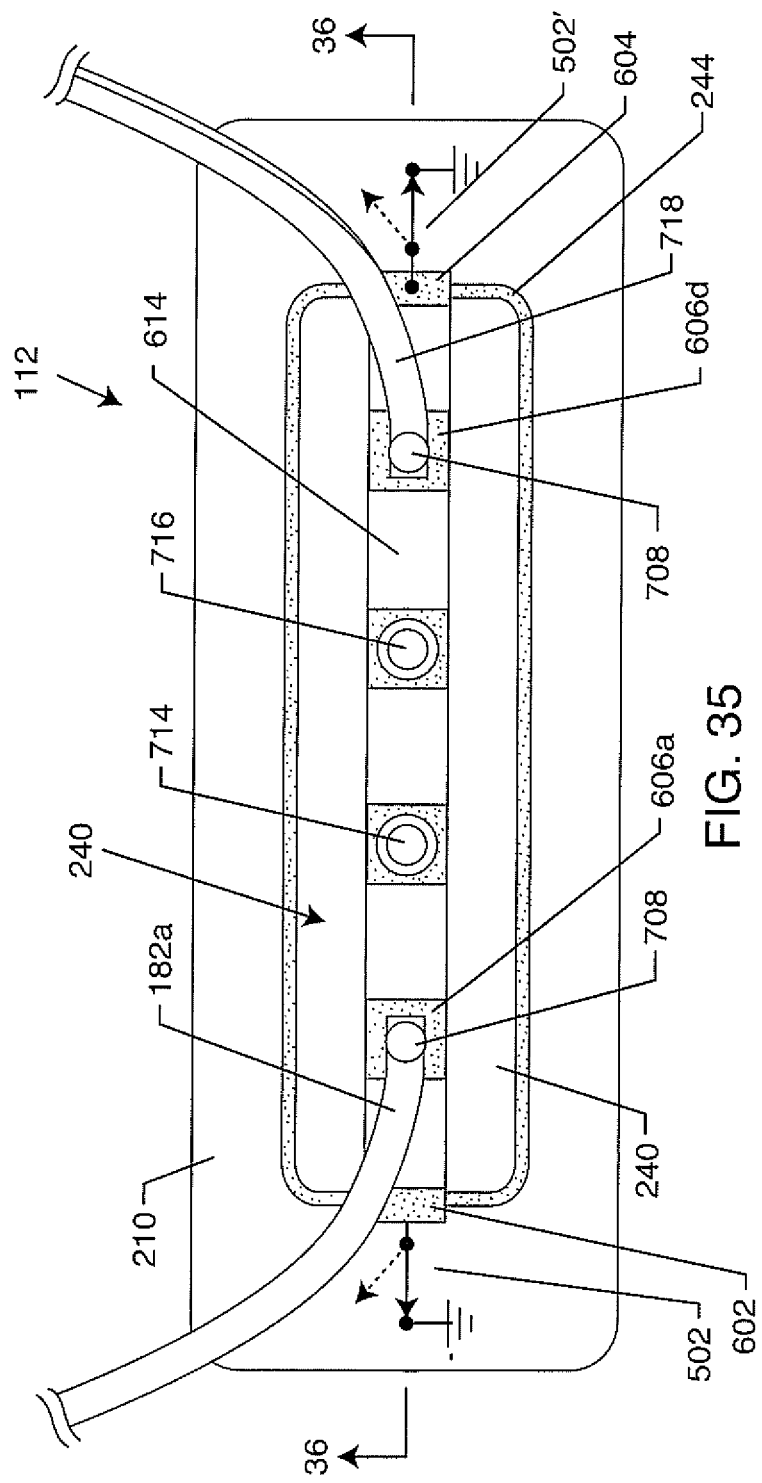
FIG. 35 is a top view of the device side of the flat-thru capacitor of FIG. 33 mounted in a tombstone position onto the insulator and ferrule of a hermetic feedthrough.

FIG. 35 illustrates a method of installing the quad polar flat-thru capacitor of FIG. 33 in a tombstone position on the device side of an AIMD ferrule 210 and/or insulator 240. Shown schematically are two electrical RF switches 502 and 502' of the present invention. The purpose of these RF switches is to disconnect the ground capacitor metallizations 602 and 604 of the flat-thru capacitor, thereby disconnecting the ground electrode plates 612 of the flat-thru capacitor so that the flat-thru capacitor will be freely floating from the system ground 210, 103. When the RF switches 502 and 502' are in their OPEN position, this floats the quad polar filter capacitances above system ground 210, 103. It is also desirable that RF switches 502 and 502' be OPEN during delivery of an ICD shock. As previously disclosed, the quad polar capacitors will still be commonly connected to each other in series through the common ground electrodes 612, but at least for an SVC and an RV situation, the amount of capacitance is half and the inrush current $i_c$ is also halved. As previously disclosed, the ICD pulse voltage is be halved.

Figure 36:
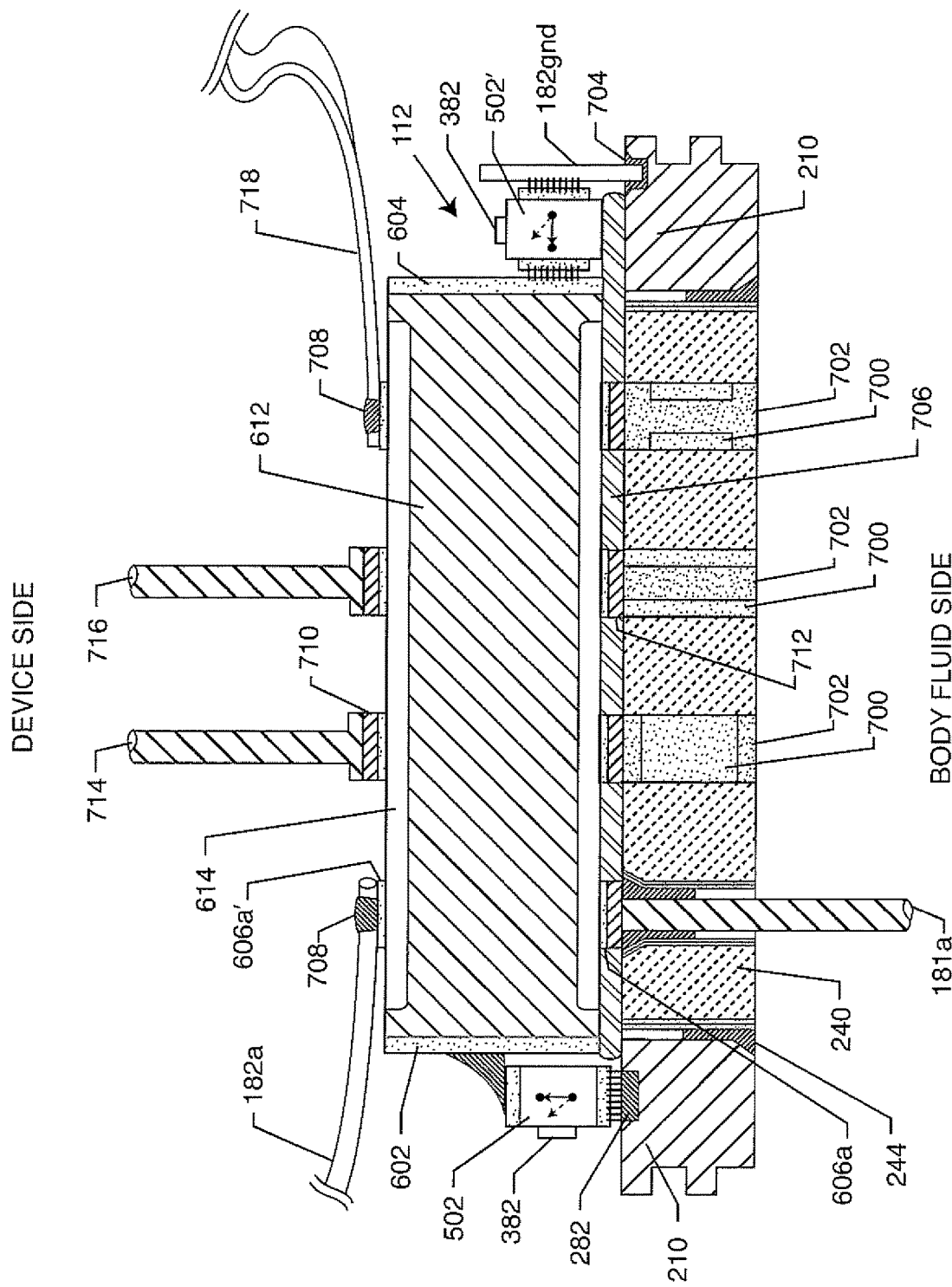
FIG. 36 is a sectional view taken from section 36-36 of FIG. 35 illustrating the flat-thru capacitor ground electrode plate(s). This isometric view illustrates two attachment embodiments of the RF SPST switches of FIG. 21.

FIG. 36 is a sectional view taken from section 36-36 of FIG. 35. In this sectional view, the two RF switches 502 and 502' are physically shown (instead of schematically as illustrated in FIG. 35). Referring to FIG. 36, one can see that the left-hand side RF switch 502 is connected to an oxide-resistant gold pocket pad 282 of the ferrule 210. Alternatively, gold braze 244 hermetically sealing the ferrule 210 and the insulator 240 of the hermetic feedthrough, can be moved out and spatially located underneath the RF switch 502. The gold braze 244 can also be used to accomplish an oxide-resistant ground connection. On the right-hand side of FIG. 36 is an alternative embodiment, wherein RF switch 502 is rotated such that the RF switch is grounded to an oxide-resistant ground terminal pin 182gnd, which has been laser welded 704 or gold brazed 225 (not shown) directly to the ferrule 210 of the hermetic feedthrough. The ground terminal pin 182gnd can be short, as illustrated, or may extend to the AIMD electronics for convenient grounding of an AIMD circuit board or circuit traces as needed. Also, by making the ferrule wider, the ground terminal pin 182gnd can extend all the way through the thickness of the ferrule so that the ground terminal pin 182gnd extends through the thickness of the ferrule to the device side and to the body fluid side of the hermetic feedthrough.

Referring again to FIG. 36, one can see on the device side that there are a number of ways to make electrical connection from the flat-thru capacitor to the AIMD electronics. For example, one can use flat ribbon cables 718, which can be thermal-sonically or ultrasonically welded, soldered or attached by thermal-setting conductive adhesive dots 708 to the capacitor metallizations. Alternatively, nail headed leadwires 714 and 716 can be used along with electrical connection material 710. Also, a flex cable can be attached using BGA or otherwise connected to the filter capacitor metallization 606. The flex cable can also be a rigid board, such as a circuit board, which can also be co-bonded.

Referring once again to FIG. 36, importantly, the conductive pathways that are passing through the insulator 240 to the body fluid side of the hermetic feedthrough on the left-hand side embody a leadwire 181a. This leadwire could nail headed (not shown) such that a BGA connection 712 can be made to the capacitor active metallization 606. Also shown are three-types of co-sintered conductive vias. The left-hand side co-sintered conductive via has a ceramic reinforced metal composite (CRMC) core 700 with a pure platinum cap 702 to enhance conductivity. An alternative form of a co-sintered via is shown to the right of the previous disclosed co-sintered vias with a CRMC forming an outer layer 700 and a substantially pure platinum center core 702. To the right of that co-sintered via is another embodiment of a co-sintered via having a CRMC fill comprising a counterbore at each end that is back-filled such that the pure platinum fill 702 of the CRMC 700 forms a dumbbell shape. It is noted that any of the co-sintered via embodiments disclosed in the U.S. patents incorporated by reference for FIG. 8 may also be used as conductive pathways for the embodiments of FIG. 36 and may also be used instead of terminal pins in any of the embodiments disclosed herein. There are also a number of other alternatives to co-sintered conductive vias, which also may comprise substantially pure platinum, in particular, U.S. Pat. Nos. 8,653,384; 8,938,309; 9,233,253; 9,492,657; 9,511,220; 9,511,220; 9,889,306; 9,993,650; 9,931,514; 9,993,650 and 10,249,415, the contents of which are fully incorporated herein by these references.

Referring once again to FIG. 36, one can see that there is an insulating washer 706, which prevents the flat-thru capacitor ground metallization 604 from undesirably electrically contacting the surface of the ferrule 210. It is appreciated that an insulating washer 706 can be used selectively with any of the capacitor or circuit board embodiments disclosed throughout this entire patent. For simplicity, these optional insulating washers 706 are not shown in many of the figures herein.

Figure 37:
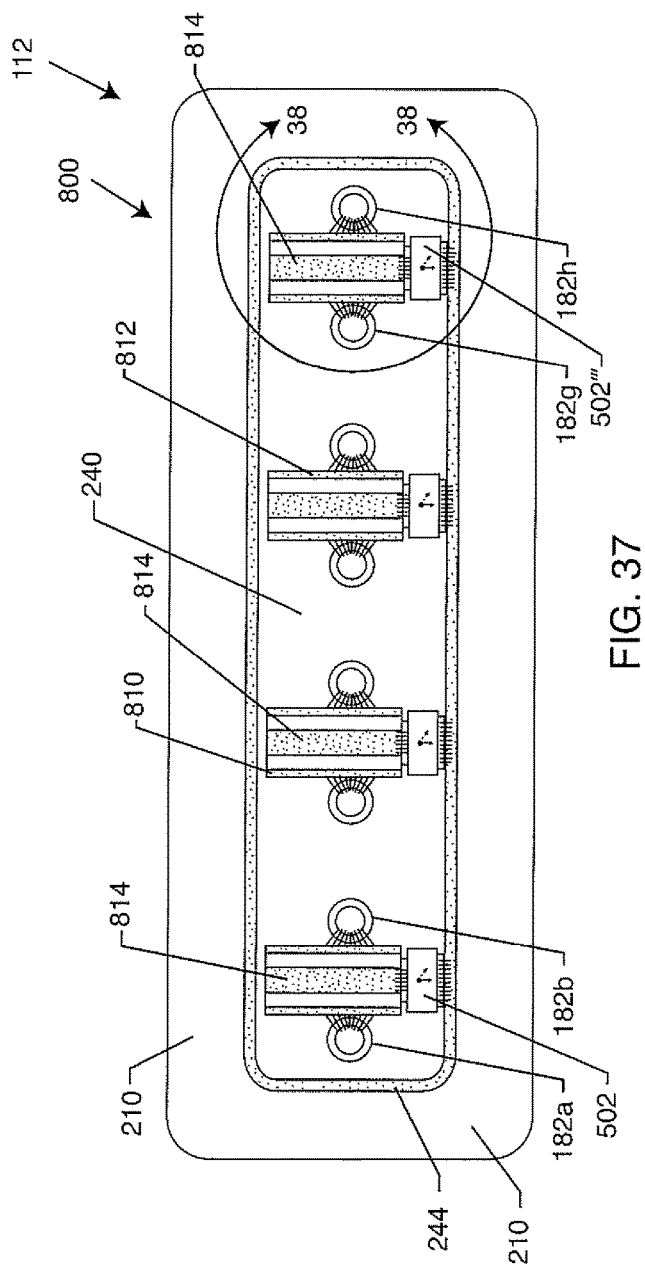
FIG. 37 illustrates the top view of the device side of the ferrule and the insulator of a hermetic feedthrough with four bipolar X2Y attenuators and four RF switches.

FIG. 37 is a device side view of a ferrule 210 with an insulator 240 as shown. In this case, the insulator is hermetically sealed by a braze 244 to ferrule 210. Prior art X2Y attenuators 800 are shown disposed directly on the insulator. It is appreciated that the X2Y attenuators can be disposed on a circuit board first, followed by the installation of the RF switches 502. Referring once again to FIG. 37, one can see that there are four RF switches 502, each one associated with an X2Y attenuator.

Figure 38:
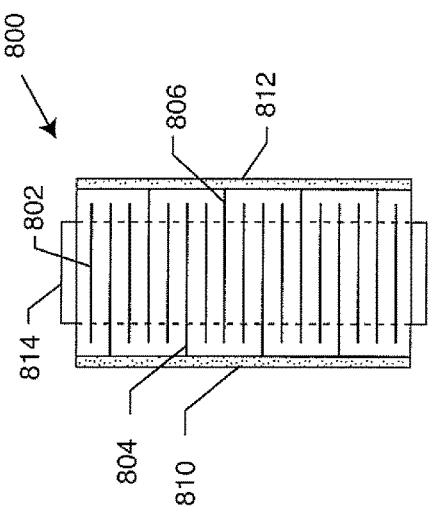
FIG. 38 is a sectional view taken from section 38-38 of FIG. 37 illustrating the internal electrode plates of the X2Y attenuator.

FIG. 38 is taken from section 38-38 of FIG. 37, illustrating a cross-sectional view of the internal electrodes of the X2Y attenuator. Shown are ground electrode plates 802, which are connected to a ground capacitor metallization stripe 814. The ground capacitor metallization stripe(s) 814 is best viewed in FIG. 37. There are pairs of active electrode plates connecting right and left. The right-hand side active electrode plates are labelled 806, which connect to the right-hand active capacitor metallization or termination 812 and the left-hand side active electrode plates are labelled 804, which connect to the left-hand side active capacitor metallization or termination 810. These X2Y attenuators are designed to be bipolar so they are associated with pairs of active terminal pins, for example, active terminal pins 182a and 182b. Active terminal pins 182g and 182h can be high-voltage active terminal pins, for example, associated with an ICD RV and SVC shocking electrodes. In this case, the right-hand side X2Y attenuator would need to be designed for high-voltage and also for high pulse inrush current $i_c$. Again, as previously disclosed, when the high-voltage switch 502''' is disconnected from ground, then the line-to-line capacitance between 182g and 182h is in series and the pulse inrush current $i_c$ (and the applied voltage) drop by half. Accordingly, as disclosed in previous embodiments, the capacitor inrush current $i_c$ during an ICD pulse is halved during a differential pulse between terminal pins 182g and 182h. Desirably, when the RF switches 502 through 502''' are in the open position, then, in accordance with the present invention, an RF test pulse 381 can be selectively provided to any of the active leadwires 182a through 182h.

Figure 39:
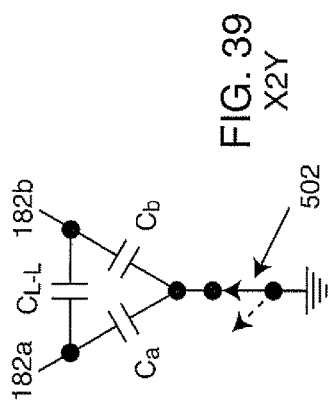
FIG. 39 is a schematic diagram illustrating the mounting layout of the X2Y capacitor on the left-hand side of the of FIG. 37.

FIG. 39 is the electrical schematic diagram of the X2Y attenuator 800 that is associated, in a bipolar manner, between terminal pins 182a and 182b. One can see a capacitance $C_{L-L}$, which is the line-to-line capacitance and also a Ca and a Cb, which is the line-to-system ground 210, 103 capacitance. This line-to-ground 210, 103 capacitance is disconnected when the RF switch 502 is in the OPEN position, but there still remains the series capacitance formed by the parallel combination of $C_{L-L}$ and Ca and CB in series with each other (which results in some significant pulse inrush current $i_c$).

Figure 40:
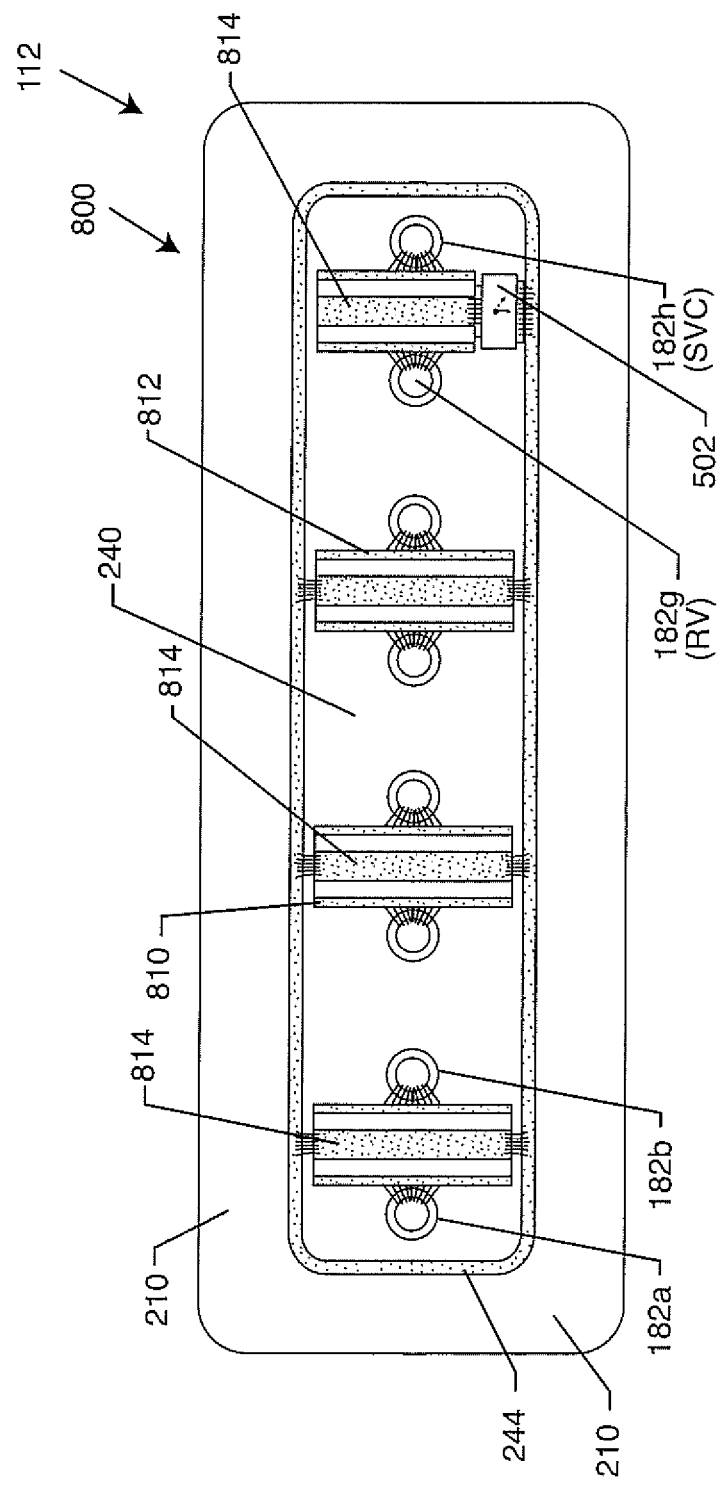
FIG. 40 is similar to FIG. 37 but with four bipolar X2Y attenuators and only a single RF switch associated with just the RV and SVC high-voltage shocking electrodes.

FIG. 40 is similar to FIG. 37, except in this embodiment, there is only one RF switch 502 and the other X2Y attenuators associated with the other active pathways are grounded at all times to the gold braze 244 of the hermetic seal so that a robust, low impedance, oxide-resistant, ground electrical connection is made to system ground 210, 103. In this embodiment, it is only the right-hand bipolar pair 182g and 182h terminal pins that are associated with an RF switch 502 of the present invention. For an implantable cardioverter defibrillator, terminal pins 182a and 182b are the high-voltage shock terminals associated with RV and SVC. In this embodiment, it would only be possible to perform an RF test 381 of the active leadwires 182g and 182h. It would not be possible to test active leadwires 182a through 182f because the filter capacitors in this embodiment are permanently connected to the system ground 210, 103, which thereby do not allow the RF interrogation signal to pass without substantial attenuation. Referring once again to FIG. 40, one can see that when the RF switch 502 is in the OPEN position, then the right-hand X2Y attenuator is disconnected from ground. When RF switch 502 is in the OPEN position, easy RF interrogation 381 of implanted lead conductors 182g and 182h is allowed. But as previously disclosed, one still has to deal with the series-parallel connections of $C_{L-L}$ and Ca and Cb in series (see representative schematic of FIG. 39). Accordingly, the right-hand X2Y attenuator needs to be rated for half of the ICD shock voltage and one-half of the filter capacitor ICD pulse inrush currents $i_c$. In other words, the right hand X2Y capacitor would have to be rated for any differential voltage or surge current that results from application of an ICD pulse that is polarized between terminals 182g and 182h.

Figure 41:
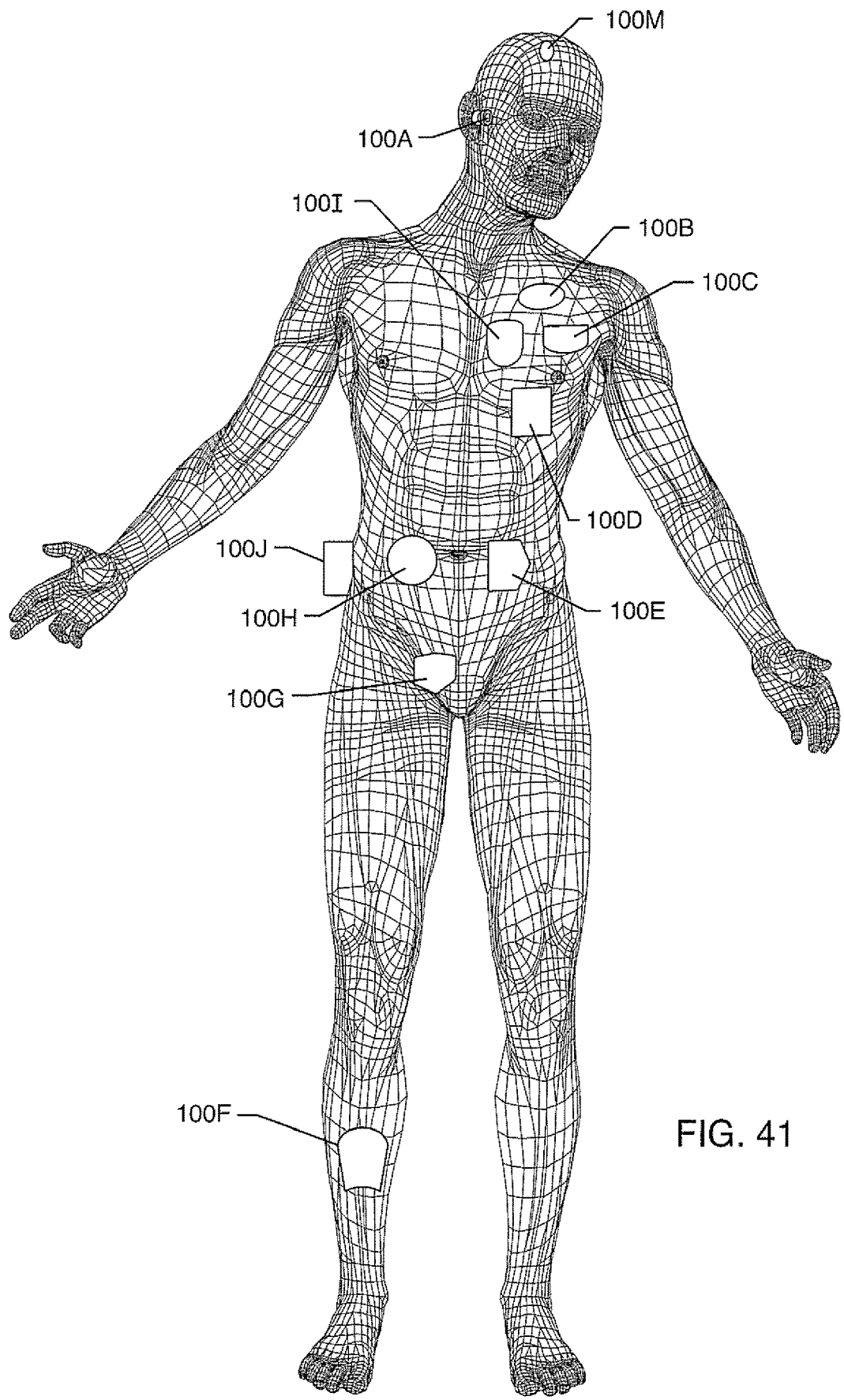
FIG. 41 is a wireform model of the human body showing various types of AIMDs to which the present invention is applicable

FIG. 41 is a wire formed diagram of a generic human body showing a number of implanted medical devices. The embodiments of the present invention are applicable to all the devices illustrated in FIG. 41. Furthermore, the embodiments of the present invention are particularly useful for ICDs 100I. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of a seizure and also providing electrical stimulation to brain tissue to prevent the seizure from actually happening. The lead wires that come from a deep brain stimulator are often placed using real time imaging. Most commonly such lead wires are placed during real time MRI. 100C shows a cardiac pacemaker, which is well-known in the art, may have endocardial or epicardial leads. Implantable pacemakers may also be leadless. The family of cardiac pacemakers 100C includes the cardiac resynchronization therapy devices (CRT-D pacemakers) and leadless pacemakers. CRT-D pacemakers are unique in that, they pace both the right and left sides of the heart. The family also includes all types of implantable loop recorders or biologic monitors, such as cardiac monitors. 100D includes the family of left ventricular assist devices (LVAD's) and artificial hearts. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack. Referring once again to element 100C, the cardiac pacemaker could also be any type of biologic monitoring and/or data recording device. This would include loop recorders or the like. Referring once again to FIG. 41, 100I is disclosed as an implantable defibrillator. It should be noted that these could be defibrillators with either endocardial or epicardial leads. This also includes a new family of subcutaneous defibrillators. ICDs, as used herein, include subcutaneous defibrillators and also CRT-D devices. CRT devices are cardiac resynchronization therapy devices that could also provide high-voltage defibrillation. In summary, as used herein, the term AIMD includes any device implanted in the human body that has at least one electronic component.

Although several embodiments have been disclosed in detail for purposes of illustration, various modifications may be made to each without departing from the scope and spirit of the invention. Accordingly, the invention is not to be limited, except as by the appended claims.

What is claimed is:
1. An RF switchable filter feedthrough for an active implantable medical device (AIMD), the RF switchable filter feedthrough comprising:
 a) an electrically conductive ferrule comprising a ferrule opening extending to a ferrule body fluid side opposite a ferrule device side;
 b) an insulator hermetically sealing the ferrule opening, the insulator comprising an insulator body fluid side opposite an insulator device side, wherein, with the insulator sealing the ferrule opening installed in a housing for the AIMD, the ferrule and insulator body fluid sides reside outside the housing, and the ferrule and insulator device sides reside inside the AIMD housing;
 c) a first active conductive pathway extending through the insulator to the insulator body fluid and device sides, the first active conductive pathway being in non-electrically conductive relation with the ferrule;
 d) a first filter capacitor disposed on the ferrule and insulator device sides, the first filter capacitor comprising a first capacitor dielectric supporting at least one first capacitor first electrode plate interleaved in a capacitive relationship with at least one first capacitor second, opposite polarity electrode plate;
 e) a first capacitor first metallization electrically connected to the at least one first capacitor first electrode plate and to the first active conductive pathway, and a first capacitor second metallization electrically connected to the at least one first capacitor second electrode plate;
 f) a first RF switch disposed on the ferrule and insulator device sides, the first RF switch comprising:
  i) a first electrical connection that electrically connects a first RF switch pole to the first capacitor second metallization electrically connected to the at least one first capacitor second electrode plate;
  ii) a second electrical connection that is electrically connectable from a first RF switch first, normally-closed throw position to the ferrule;
  iii) a third electrical connection that is electrically connectable from a first RF switch second throw position to a first AIMD RF source; and iv) a fourth electrical connection that is electrically connectable to an AIMD first throw control signal,
v) wherein, with the second electrical connection electrically connecting the first RF switch first, normally-closed throw position to the ferrule, with the third electrical connection electrically connecting the first RF switch second throw position to the first AIMD RF source, and with the fourth electrical connection electrically connected to the AIMD first throw control signal, and wherein, with the first RF switch in the first RF switch first, normally-closed position and in response to the AIMD first throw control signal, the first RF switch pole switches from the first RF switch first, normally-closed throw position to the first RE switch second throw position electrically connecting the first RE switch pole to the first AIMD RF source.

2. The RF switchable filter feedthrough of claim 1, wherein a first gold braze hermetically seals the insulator to the ferrule.

3. The RF switchable filter feedthrough of claim 2, wherein the first RF switch first, normally-closed throw position is at least partially electrically connected to at least one of the group of the first gold braze, a gold bond pad disposed in a ferrule pocket, and a ferrule ground pin mechanically and electrically connected to the ferrule.

4. The RF switchable filter feedthrough of claim 1, wherein the first active conductive pathway is configured to be connectable to a first high-voltage shocking lead of an implantable cardioverter defibrillator as the AIMD.

5. The RF switchable filter feedthrough of claim 1, further including a plurality of active conductive pathways and corresponding RE switches and filter capacitors.

6. The RE switchable filter feedthrough of claim 1, wherein the first filter capacitor is selected from the group of a two-terminal MLCC chip capacitor, a three-terminal feedthrough capacitor, a flat-thru capacitor, and an X2Y attenuator.

7. The RF switchable filter feedthrough of claim 6, wherein the two-terminal MLCC chip capacitor is a reverse geometry two-terminal MLCC chip capacitor.

8. The RF switchable filter of claim 1, wherein the first RF switch is selected from the group of a single-pole double-throw switch, a double-pole double-throw switch, and an n-pole n-throw switch.

9. The RF switchable filter feedthrough of claim 1, wherein the first filter capacitor and the first RF switch are disposed on a circuit board that is configured to be disposed on the ferrule and insulator device sides.

10. The RF switchable filter feedthrough of claim 1, wherein the first RF switch further comprises:
a) a fifth electrical connection that is electrically connectable to the AIMD first throw control signal to thereby provide a second electrical connection to the AIMD first throw control signal;
b) a sixth electrical connection that is electrically connectable to the first AIMD RF source to thereby provide a second electrical connection to the first AIMD RF source; and
c) a seventh electrical connection that is electrically connectable to the ferrule to thereby provide a first RF switch ground.

11. The RF switchable filter feedthrough of claim 1, wherein the first filter capacitor has a dielectric constant greater than zero, but less than 1,000.

12. The RF switchable filter feedthrough of claim 1, further comprising:
a) a second active conductive pathway extending through the insulator to the insulator body fluid and device sides, the second active conductive pathway being in non-electrically conductive relation with the ferrule;
b) a second filter capacitor disposed on the ferrule and insulator device sides, the second filter capacitor comprising a second capacitor dielectric supporting at least one second capacitor first electrode plate interleaved in a capacitive relationship with at least one second capacitor second, opposite polarity electrode plate, wherein the second capacitor first electrode plate is electrically connected to the second conductive pathway;
c) a second RF switch disposed on the ferrule and insulator device sides, the second RF switch comprising:
i) an eighth electrical connection that electrically connects a second RE switch pole to the second capacitor second electrode plate;
ii) a ninth electrical connection that is electrically connectable from a second RF switch first, normally-closed throw position to the ferrule;
iii) a tenth electrical connection that is electrically connectable from a second RF switch second throw position to a second AIMD RF source; and
iv) an eleventh electrical connection that is electrically connectable to an AIMD second throw control signal,
v) wherein, with the ninth electrical connection electrically connecting the second RF switch first, normally-closed throw position to the ferrule, with the tenth electrical connection electrically connecting the second RF switch second throw position to the second AIMD RF source, and with the eleventh electrical connection electrically connected to the AIMD second throw control signal, and wherein, with the second RF switch in the second RF switch first, normally-closed position and in response to the AIMD second throw control signal, the second RF switch pole is configured to switch from the second RF switch first, normally-closed throw position to the second RF switch second throw position electrically connecting the second RF switch pole to the second AIMD RF source.

13. The RF switchable filter feedthrough of claim 12, wherein, in response to the AIMD second throw control signal, the second RF switch switches from the second RF switch second throw position back to the second RF switch first, normally-closed throw position.

14. The RF switchable filter feedthrough of claim 1, wherein, in response to the AIMD first throw control signal, the first RF switch switches from the first RF switch second throw position back to the first RF switch first, normally-closed throw position.

15. The RF switchable filter feedthrough of claim 1, wherein, upon removal of the AIMD first throw control signal, the first RF switch automatically switches from the first RF switch second throw position back to the first RF switch first, normally closed first throw position.

16. An RF switchable filter feedthrough for an active implantable medical device (AIMD), the RF switchable filter feedthrough comprising:
a) an electrically conductive ferrule comprising a ferrule opening extending to a ferrule body fluid side opposite a ferrule device side;

b) an insulator hermetically sealed in the ferrule opening by a gold braze, the insulator comprising an insulator body fluid side opposite an insulator device side, wherein, with the insulator sealing the ferrule opening installed in a housing for the AIMD, the ferrule and insulator body fluid sides reside outside the housing, and the ferrule and insulator device sides reside inside the AIMD housing;

c) a first active leadwire extending through the insulator to the insulator body fluid and device sides, the first active leadwire being in non-electrically conductive relation with the ferrule;

d) a first two-terminal MLCC chip capacitor disposed on the ferrule and insulator device sides, the first MLCC chip capacitor comprising a first MLCC chip capacitor dielectric supporting at least one first MLCC chip capacitor first electrode plate interleaved in a capacitive relationship with at least one first MLCC chip capacitor second, opposite polarity electrode plate, wherein the at least one first MLCC chip capacitor first electrode plate is electrically connected to the first active leadwire;

e) a first RF switch disposed on the ferrule and insulator device sides, the first RF switch comprising:
  i) a first electrical connection that electrically connects a first RF switch pole to the at least one first MLCC chip capacitor second electrode plate;
  ii) a second electrical connection that is electrically connectable from a first RF switch first, normally-closed throw position to the ferrule;
  iii) a third electrical connection that is electrically connectable from a first RE switch second throw position to a first AIMD RF source; and
  iv) a fourth electrical connection that is electrically connectable to an AIMD first throw control signal,
  v) wherein, with the second electrical connection electrically connecting the first RF switch first, normally-closed throw position to the ferrule, with the third electrical connection electrically connecting the first RF switch second throw position to the first AIMD RF source, and with the fourth electrical connection electrically connected to AIMD first throw control signal, and wherein, with the first RF switch in the first RF switch first, normally-closed position and in response to the AIMD first throw control signal, the first RF switch pole switches from the first RF switch first, normally-closed throw position to the first RF switch second throw position electrically connecting the first RF switch pole to the first AIMD RF source.

17. The RF switchable filter feedthrough of claim 16, further comprising:
  a) a second active leadwire extending through the insulator to the insulator body fluid and device sides, the second active leadwire being in non-electrically conductive relation with the ferrule;
  b) a second two-terminal MLCC chip capacitor disposed on the ferrule and insulator device sides, the second MLCC chip capacitor comprising a second MLCC chip capacitor dielectric supporting at least one second MLCC chip capacitor first electrode plate interleaved in a capacitive relationship with at least one second MLCC chip capacitor second, opposite polarity electrode plate, wherein the second MLCC chip capacitor first electrode plate is electrically connected to the second active leadwire;
  c) a second RF switch disposed on the ferrule and insulator device sides, the second RF switch comprising:
    i) a fifth electrical connection that electrically connects a second RF switch pole to the second MLCC chip capacitor second electrode plate;
    ii) a sixth electrical connection that is electrically connectable a second RF switch first, normally-closed throw position to the ferrule;
    iii) a seventh electrical connection that is electrically connectable from a second RF switch second throw position to a second AIMD RF source; and
    iv) an eighth electrical connection that is electrically connectable to an AIMD second throw control signal,
    v) wherein, with the sixth electrical connection electrically connecting the first RF switch first, normally-closed throw position to the ferrule, with the seventh electrical connection electrically connecting the first RF switch second throw position to the first AIMD RF source, and with the eighth electrical connection electrically connected to the AIMD second throw control signal, and wherein, with the second RF switch in the second RF switch first, normally-closed position and in response to a first throw position signal of the AIMD second throw control signal, the second RF switch pole switches from the second RF switch first, normally-closed throw position to the second RF switch second throw position electrically connecting the second RF switch pole to the second AIMD RF source.

18. The RF switchable filter feedthrough of claim 17, wherein, in response to the AIMD second throw control signal, the second RF switch switches from the second RF switch second throw position back to the second RF switch first, normally-closed throw position.

19. The RF switchable filter feedthrough of claim 16, wherein the first active leadwire is configured to be connectable to a first high-voltage shocking lead of an implantable cardioverter defibrillator as the AIMD.

20. The RF switchable filter feedthrough of claim 19, wherein during delivery of an ICD high-voltage cardioversion shock to the first active leadwire, the AIMD first throw control signal is configured to command the first RF switch to switch to an open position, thereby disconnecting the first MLCC filter capacitor from the ferrule.

21. The RF switchable filter feedthrough of claim 16, wherein, in response to the AIMD first throw control signal, the first RF switch switches from the first RF switch second throw position back to the first RF switch first, normally-closed throw position.

22. The RF switchable filter feedthrough of claim 16, wherein, upon removal of the AIMD first throw control signal, the first RF switch automatically switches from the first RF switch second throw position back to the first RF switch first, normally closed first throw position.

23. An active implantable medical device (AIMD) comprising an RF switchable filter feedthrough, the AIMD comprising:
  a) a housing for the AIMD, the housing serving as a system ground, wherein a housing body fluid side and a housing device side reside outside and inside the AIMD housing, respectively;
  b) a first active conductive pathway extending through the housing to the housing body fluid and device sides in a non-electrically conductive relation with the AIMD housing;
  c) a first filter capacitor disposed on the housing device side, the first filter capacitor comprising a first capacitor dielectric supporting at least one first capacitor first electrode plate interleaved in a capacitive relationship with at least one first capacitor second, opposite polarity electrode plate, wherein the at least one first capacitor first electrode plate is electrically connected to the first conductive pathway;

d) a first RF switch disposed on the housing device side, the first RF switch comprising:
   i) a first electrical connection that electrically connects a first RF switch pole to the at least one first capacitor second electrode plate;
   ii) a second electrical connection that electrically connects a first RF switch first, normally-closed throw position to the housing as the system ground;
   iii) a third electrical connection that electrically connects a first RF switch second throw position to a first AIMD RF source disposed on the housing device side; and
   iv) a fourth electrical connection that is electrically connected to an AIMD first throw control signal disposed on the housing device side,
   v) wherein, with the first RF switch in the first RF switch first, normally-closed position and in response to a first throw position signal of the AIMD first throw control signal, the first RF switch pole switches from the first RF switch first, normally-closed throw position to the first RF switch second throw position electrically connecting the RF switch pole to the first AIMD RF source.

24. The AIMD of claim 23, wherein the first active conductive pathway is configured to be connectable to a first high-voltage shocking lead of an implantable cardioverter defibrillator as the AIMD.

25. The RF switchable filter feedthrough of claim 24, wherein during delivery of an ICD high-voltage cardioversion shock to the first active conductive pathway, the AIMD first throw control signal commands the RF switch to switch to an open position thereby disconnecting the MLCC filter capacitor second electrode plate from ferrule.

26. The RF switchable filter feedthrough of claim 24, wherein during an RF signal interrogation, the AIMD first throw control signal commands the first RF switch to switch to an open position thereby disconnecting the MLCC filter capacitor second electrode plate from ferrule, and the AIMD first throw control signal is also sent to the first RF switch pole connected to the first active conductive pathway, and wherein the AIMD first throw control signal commands the first RF switch to switch to the first RF switch second throw position connected to the AIMD first throw control signal.

27. The AIMD of claim 23, wherein the first RF switch further comprises:
   a) a fifth electrical connection that is electrically connected to the AIMD first throw control signal to thereby provide a second electrical connection to the AIMD first throw control signal;
   b) a sixth electrical connection that is electrically connected to the first AIMD RF source to thereby provide a second electrical connection to the first AIMD RF source; and
   c) a seventh electrical connection that is electrically connected to the housing ground plane to thereby provide a first RF switch ground.

28. The AIMD of claim 23, wherein the first filter capacitor has a dielectric constant greater than zero, but less than 1,000.

29. The AIMD of claim 23, wherein, in response to the AIMD first throw control signal, the first RF switch switches from the first RF switch second throw position back to the first RF switch first, normally-closed throw position.

30. The AIMD of claim 23, wherein, upon removal of the AIMD first throw control signal, the first RF switch automatically switches from the first RF switch second throw position back to the first RF switch first, normally closed first throw position.

31. An RF switchable filter feedthrough for an active implantable medical device (AIMD), the RE switchable filter feedthrough comprising:
   a) a circuit board;
   b) a two-terminal MLCC chip capacitor comprising an MLCC chip capacitor dielectric supporting at least one MLCC chip capacitor first electrode plate interleaved in a capacitive relationship with at least one MLCC chip capacitor second, opposite polarity electrode plate, wherein the at least one MLCC chip capacitor first electrode plate is electrically connectable to an active conductive pathway of a feedthrough, the feedthrough comprising an electrically conductive ferrule having a ferrule opening, an insulator hermetically sealing the ferrule opening, and the active conductive pathway extending through the insulator in a non-electrically conductive relation with the ferrule;
   c) a first RF switch disposed on the circuit board, the first RF switch comprising:
      i) a first electrical connection that electrically connects the MLCC chip capacitor first electrode plate to the active conductive pathway;
      ii) a second electrical connection that electrically connects a first RF switch pole to the MLCC chip capacitor second electrode plate;
      iii) a third electrical connection that is electrically connectable from a first RF switch first, normally-closed throw position to the ferrule of the feedthrough;
      iv) a fourth electrical connection that electrically connectable from a first RF switch second throw position to a first AIMD RF source; and
      v) a fifth electrical connection that is electrically connectable to an AIMD control signal,
      vi) wherein, with the third electrical connection electrically connecting the first RF switch first, normally-closed throw position to the ferrule of the feedthrough, with the fourth electrical connection electrically connecting the first RF switch second throw position to the first AIMD RF source, and with the fifth electrical connection electrically connected to the AIMD control signal, and wherein, with the first RF switch in the first RF switch first, normally-closed position and in response to the AIMD control signal, the first RF switch pole is configured to switch from the first RF switch first, normally-closed throw position to the first RF switch second throw position electrically connecting the first RF switch pole to the first AIMD RF source.

32. The RF switchable filter feedthrough of claim 31, wherein, in response to the AIMD control signal, the first RF switch switches from the first RF switch second throw position back to the first RF switch first, normally-closed throw position.

33. The RF switchable filter feedthrough of claim 32, wherein, upon removal of the AIMD control signal, the first RF switch automatically switches from the first RF switch second throw position back to the first RF switch first, normally closed first throw position.

* * * * *